United States Patent
Wanunu et al.

(10) Patent No.: US 12,320,796 B2
(45) Date of Patent: Jun. 3, 2025

(54) LIPID-FREE ANCHORING OF THERMOPHILIC BACTERIOPHAGE G20c PORTAL ADAPTER INTO SOLID-STATE NANOPORES

(71) Applicants: Northeastern University, Boston, MA (US); University of York, York (GB)

(72) Inventors: Meni Wanunu, Sharon, MA (US); Alfred Antson, York (GB); Sandra Greive, York (GB); Benjamin Cressiot, Montlignon (FR)

(73) Assignees: Northeastern University, Boston, MA (US); University of York, York (GB)

( * ) Notice: Subject to any disclaimer, the term of this patent is extended or adjusted under 35 U.S.C. 154(b) by 0 days.

(21) Appl. No.: 18/429,862

(22) Filed: Feb. 1, 2024

(65) Prior Publication Data
US 2024/0361296 A1    Oct. 31, 2024

Related U.S. Application Data

(63) Continuation of application No. 17/809,705, filed on Jun. 29, 2022, now Pat. No. 11,933,778, which is a
(Continued)

(51) Int. Cl.
*G01N 33/487* (2006.01)
*B81B 1/00* (2006.01)
(Continued)

(52) U.S. Cl.
CPC ....... *G01N 33/48721* (2013.01); *B81B 1/002* (2013.01); *C07K 14/005* (2013.01);
(Continued)

(58) Field of Classification Search
None
See application file for complete search history.

(56) References Cited

U.S. PATENT DOCUMENTS

| 11,313,857 B2 | 4/2022 | Wanunu et al. |
| 11,408,880 B2 | 8/2022 | Wanunu et al. |

(Continued)

FOREIGN PATENT DOCUMENTS

| WO | 2009/020682 A2 | 2/2009 |
| WO | 2019/222717 A2 | 11/2019 |

(Continued)

OTHER PUBLICATIONS

Adam R Hall et al: "Hybrid pore formation by directed insertion of [alpha]-haemolysin into solid-state nanopores", Nature Nanotechnology, Nature Publishing Group, GB, vol. 5, No. 12, Nov. 28, 2010 (Nov. 28, 2010), pp. 874-877.

(Continued)

*Primary Examiner* — J. Christopher Ball
(74) *Attorney, Agent, or Firm* — Hamilton, Brook, Smith & Reynolds, P.C.

(57) ABSTRACT

Hybrid nanopores, comprising a protein pore supported within a solid-state membrane, which combine the robust nature of solid-state membranes with the easily tunable and precise engineering of protein nanopores. In an embodiment, a lipid-free hybrid nanopore comprises a water soluble and stable, modified portal protein of the *Thermus thermophilus* bacteriophage G20c, electrokinetically inserted into a larger nanopore in a solid-state membrane. The hybrid pore is stable and easy to fabricate, and exhibits low peripheral leakage, allowing sensing and discrimination among different types of biomolecules.

18 Claims, 14 Drawing Sheets
(14 of 14 Drawing Sheet(s) Filed in Color)
Specification includes a Sequence Listing.

Related U.S. Application Data continuation of application No. 16/416,139, filed on May 17, 2019, now Pat. No. 11,408,880.

(60) Provisional application No. 62/673,118, filed on May 17, 2018.

(51) Int. Cl.
  *B82Y 15/00* (2011.01)
  *C07K 14/005* (2006.01)
  *C12Q 1/6869* (2018.01)

(52) U.S. Cl.
  CPC .......... *C12Q 1/6869* (2013.01); *B82Y 15/00* (2013.01); *C12N 2795/00022* (2013.01); *Y10S 930/22* (2013.01)

(56) References Cited

U.S. PATENT DOCUMENTS

| | | |
|---|---|---|
| 11,703,476 B2 | 7/2023 | Wanunu et al. |
| 11,933,778 B2 | 3/2024 | Wanunu et al. |
| 11,994,508 B2 | 5/2024 | Wanunu et al. |
| 2016/0076091 A1 | 3/2016 | Huber et al. |
| 2019/0360998 A1 | 11/2019 | Wanunu et al. |
| 2021/0123884 A1 | 4/2021 | Wanunu et al. |
| 2022/0334097 A1 | 10/2022 | Wanunu et al. |
| 2022/0373533 A1 | 11/2022 | Wanunu et al. |
| 2023/0017101 A1 | 1/2023 | Alibakhshi et al. |

FOREIGN PATENT DOCUMENTS

| | | |
|---|---|---|
| WO | 2021/062307 A1 | 4/2021 |
| WO | 2021/108780 A1 | 6/2021 |
| WO | 2022/159908 A1 | 7/2022 |
| WO | 2023/230516 A1 | 11/2023 |

OTHER PUBLICATIONS

Akeson, M., Branton, D., Kasianowicz, J. J., Brandin, E. & Deamer, D. W. Microsecond time-scale discrimination among polycytidylic acid, polyadenylic acid, and polyuridylic acid as homopolymers or as segments within single RNA molecules. Biophysj 77, 3227-3233 (1999).

Baaken, G. et al. High-Resolution Size-Discrimination of Single Nonionic Synthetic Polymers with a Highly Charged Biological Nanopore. ACS Nano 9, 6443-6449 (2015).

Butler, T. Z., Pavlenok, M., Derrington, I. M., Niederweis, M. & Gundiach, J. H. Single-molecule DNA detection with an engineered MspA protein nanopore. Proc. Natl. Acad. Sci. U.S.A. 105, 20647-20652 (2008).

Casjens, S. R. & Gilcrease, E. B. Determining DNA packaging strategy by analysis of the termini of the chromosomes in tailed-bacteriophage virions. Methods Mol Biol 502, 91-111 (2009).

Castell, O. K., Berridge, J_ & Wallace, M. I. Quantification of membrane protein inhibition by optical ion flux in a droplet nterface bilayer array. Angewandte Chemie International Edition 51, 3134-3138 (2012).

Cressiot et al., "Porphyrin-Assisled Docking of a Thermophage Portal Protein into Lipid Bilayers: Nanopore Engineering and Characterization," Biophysical Journal, vol. 114, No. 3, 2018.

Cressiot, B. et al. Dynamics and Energy Contributions for Transport of Unfolded Pertactin through a Protein Nanopore. ACS Nano 9, 9050-9061 (2015).

Cressiot, B., et al., "Porphyrin-Assisted Docking of a Thermophage Portal Protein into Lipid Bilayers: Nanopore Engineering and Characterization", ACS Nano, vol. 11, No. 12, Nov. 15, 2017, pp. 11931-11945.

Cressiot, B., et al., "Thermostable virus portal proteins as reprogrammable adapters for solid-state nanopore sensors", Nature communication, vol. 9, No. 1, Nov. 7, 2018, 1 page.

Derrington, I. M. et al. Nanopore DNA sequencing with MspA. Proc. Natl. Acad. Sci. U.S.A. 107, 16060-16065 (2010).

Eric Gouaux, "a-Hemolysin from *Staphylococcus aureus*: An Archetype of β-Barrel, Channel-Forming Toxins," Journal of Structural Biology 121, 110-122 (1998) Article No. SB983959.

Fennouri, A. A. et al. Single molecule detection of glycosaminoglycan hyaluronic acid oligosaccharides and depolymerization enzyme activity using a protein nanopore. ACS Nano 6, 9672-9678 (2012).

Garalde, D. R. et al. Highly parallel direct RNA sequencing on an array of nanopores. Nature Methods 15, 201-206 (2018).

Gu, L. Q., Braha, 0., Conlan, S., Cheley, S. & Bayley, H. Stochastic sensing of organic analytes by a pore-forming rolein containing a molecular adapter. Nature 398, 686-690 (1999).

Guo, "Atomic model for the dimeric FO region of mitochondrial ATP synthase," Science. Nov. 17, 2017; 358 (6365): 936-940.

Henrickson, S. E., Misakian, M., Robertson, B. & Kasianowicz, J. J. Driven DNA transport into an asymmetric nanometer-scale pore. Phys Rev Lett 85, 3057-3060 (2000).

Hoogerheide, D. P., Garaj, S. & Golovchenko, J. A. Probing Surface Charge Fluctuations with Solid-State Nanopores. Physical Review Letters 102, 256804 (2009).

Howorka, S. & Siwy, Z. Nanopore analytics: sensing of single molecules. Chem. Soc. Rev. 38, 2360 (2009).

Huang, G., Willems, K., Soskine, M., Wloka, C. & Maglia, G. Electro-Osmotic capture and ionic discrimination of eptide and protein biomarkers with FraC nanopores. Nature Communications 8, 935 (2017).

International Preliminary Search Report and Written Opinion for International Application No. PCT/US2019/033006, entitled "Lipid-Free Anchoring of Thermophilic Bacteriophage G20c Portal Adapter into Solid-State Nanopores," consisting of 11 pages, dated Nov. 17, 2020.

International Search Report and Written Opinion received for PCT Patent Application No. PCT/US2019/033006, mailed on Dec. 2, 2019, 18 pages (18 pages of Original Document).

International Search Report and Written Opinion received for PCT Patent Application No. PCT/US2023/067412, mailed on Sep. 18, 2023, 14 pages.

Invitation to Pay Additional Fees and Annex of Partial International Search Report for International Application No. PCT/US2019/033006, entitiled: "Lipid-Free Anchoring of Thermophilic Bacteriophage G20c Portal Adapter into Solid-State Nanopores," dated Oct. 9, 2019.

Jain, M. et al. Improved data analysis for the MinION nanopore sequencer. Nature Methods 12, 351-356 (2015).

Jain, M. et al. Nanopore sequencing and assembly of a human genome with ultra-long reads. Nature Biotechnology 36, 338-345 (2018).

Japrung, D., Henricus, M., Li, Q., Maglia, G. & Bayley, H. Urea Facilitates the Translocation of Single-Stranded DNA and RNA Through the a-Hemolysin Nanopore. Biophysical Journal 98, 1856-1863 (2010).

Kadima, W. et al. The influence of ionic strength and pH on the aggregation properties of zinc-free insulin studied by static and dynamic laser light scattering. Biopolymers 33, 1643-1657 (1993).

Kasianowicz, J. J. et al. Analytical applications for pore-forming proteins. Biochim Biophys Acta 1858, 593-606 (2016).

Kasianowicz, J. J., Brandin, E., Branton, D. & Deamer, D. W. Characterization of individual polynucleotide molecules using a membrane channel. Proc. Natl. Acad. Sci. U.S.A. 93, 13770-13773 (1996).

Khan Muhammad S et al: "Electrochemical impedance spectroscopy for black lipid membranes fused with channel protein supported on solid-state nanopore", European Biophysics Journal, Springer, DE, vol. 45, No. 8, Aug. 1, 2016 (Aug. 1, 2016), pp. 843-852.

Larkin, J. et al. Slow DNA transport through nanopores in hafnium oxide membranes. ACS Nano 7, 10121-10128 (2013).

Larkin, J., Henley, R. Y., Jadhav, V., Korlach, J. & Wanunu, M. Length-independent DNA packing into nanopore zero-mode waveguides for low-input DNA sequencing. Nat Nano 12, 1169-1175 (2017).

(56) References Cited

OTHER PUBLICATIONS

Lebedev, A. A. et al. Structural framework for DNA translocation via the viral portal protein. EMBO J 26, 1984-1994 (2007).
Lee, J. et al. Semisynthetic Nanoreactor for Reversible Single-Molecule Covalent Chemistry. ACS Nano 10, 8843-8850 (2016).
Lin, J., Fabian, M., Sonenberg, N. & Meller, A. Nanopore detachment kinetics of poly(A) binding proteins from RNA molecules reveals the critical role of C-terminus interactions. Biophysical Journal 102, 1427-1434 (2012).
Loman, N. J., Quick, J. & Simpson, J. T. A complete bacterial genome assembled de novo using only nanopore sequencing data. Nature Methods 12, 733-735 (2015).
Luchian, T., Shin, S.-H. & Bayley, H. Kinetics of a three-step reaction observed at the single-molecule level. Angew Chem Int Ed Engl 42, 1926-1929 (2003).
McNally, B. et al. Optical Recognition of Converted DNA Nucleotides for Single-Molecule DNA Sequencing Using Nanopore Arrays. Nano Lett 10, 2237-2244 (2010).
Meller, A. & Branton, D. Single molecule measurements of DNA transport through a nanopore. Electrophoresis 23, 2583-2591 (2002).
Meng, H. et al. Nanopore analysis of tethered peptides. J Pepi Sci 16, 701-708 (2010).
Mereuta, L. et al. Slowing down single-molecule trafficking through a protein nanopore reveals intermediates for eplide translocation. Sci Rep 4, 3885-3885 (2014).
Merstorf, C. et al. Wild type, mutant protein unfolding and phase transition detected by single-nanopore recording. AC Chem Biol 7, 652-658 (2012).
Mohammad, M. M. et al. Engineering a rigid protein tunnel for biomolecular detection. J Am Chem Soc 134, 9521-9531 (2012).
Nivala, J., Marks, D. B. & Akeson, M. Unfoldase-mediated protein translocation through an a-hemolysin nanopore. Nat Biotechnol 31, 247-250 (2013).
Oukhaled, A. et al. Dynamics of completely unfolded and native proteins through solid-state nanopores as a function o' electric driving force. ACS Nano 5, 3628-3638 (2011).
Oukhaled, A., Bacri, L., Pastoriza-Gallego, M., Betton, J.-M. & Pella, J. Sensing proteins through nanopores: fundamental to applications. ACS Chem Biol 7, 1935-1949 (2012).
Pastoriza-Gallego, M. et al. Dynamics of unfolded protein transport through an aerolysin pore. J Am Chem Soc 133, 2923-2931 (2011).
Pastoriza-Gallego, M. et al. Evidence of unfolded protein translocation through a protein nanopore. ACS Nano 8, 11350-11360 (2014).
Piguet, F. et al. Identification of single amino acid differences in uniformly charged homopolymeric peptides with aerolysin nanopore. Nature Communications 9, (2018).
Notice of Allowance and Fees Due (PTOL-85) Mailed on Nov. 2, 2023 for U.S. Appl. No. 17/809,705, 9 page(s).
Requirement for Restriction/Election Mailed on Sep. 20, 2023 for U.S. Appl. No. 17/809,705, 9 page(s).
Robertson, J. W. F. et al. Single-molecule mass spectrometry in solution using a solitary nanopore. Proc. Natl. Acad. Sci. U.S.A. 104, 8207-8211 (2007).
Rodriguez-Larrea, D. & Bayley, H. Multislep protein unfolding during nanopore translocation. Nature Nanotech 8, 288-295 (2013).
Rosen, C. B., Rodriguez-Larrea, D. & Bayley, H. Single-molecule site-specific detection of protein phosphorylation with a nanopore. Nat Biotechnol 32, 179-181 (2014).
Skinner, G. M., van den Hout, M., Broekmans, 0., Dekker, C. & Dekker, N. H. Distinguishing single- and double-stranded nucleic acid molecules using solid-state nanopores. Nano Lett 9, 2953-2960 (2009).
Song, L. et al. Structure of staphylococcal alpha-hemolysin, a heptameric transmembrane pore. Science 274, 1859-1866 (1996).
Stefureac, R., Long, Y.-T., Kraatz, H.-B., Howard, P. & Lee, J. S. Transport of alpha-helical peptides through alpha-hemolysin and aerolysin pores. Biochemistry 45, 9172-9179 (2006).
Sutherland, T. C. et al. Structure of peptides investigated by nanopore analysis. Nano Lett 4, 1273-1277 (2004).
Van Meervell, V. et al. Real-Time Conformational Changes and Controlled Orientation of Native Proteins Inside a Protein Nanoreactor. J Am Chem Soc 139, 18640-18646 (2017).
Verschueren, D. V., Jonsson, M. P. & Dekker, C. Temperature dependence of DNA translocations through solid-state nanopores. Nanotechnology 26, 234004 (2015).
Wang, H. et al. Determining the Physical Properties of Molecules with Nanometer-Scale Pores. ACS Sensors 3, 251-263 (2018).
Wang, H.-Y., Ying, Y.-L., Li, Y., Kraatz, H.-B. & Long, Y.-T. Nanopore Analysis of a-Amyloid Peptide Aggregation Transition Induced by Small Molecules. Anal Chem 83, 1746-1752 (2011).
Wanunu, M. et al. Rapid electronic detection of probe-specific microRNAs using thin nanopore sensors. Nature Nanotech 5, 807-814 (2010).
Wescoe, Z. L., Schreiber, J. & Akeson, M. Nanopores discriminate among five C5-cytosine variants in DNA. J Am Chem Soc 136, 16582-16587 (2014).
Whittingham, J. L., Edwards, D. J., Anlson, A. A., Clarkson, J. M. & Dodson, G. G. Interactions of phenol and m-cresol n the insulin hexamer, and their effect on the association properties of B28 pro-> Asp insulin analogues. Biochemistry 37, 11516-11523 (1998).
Willems, K., Van Meervelt, V., Wicka, C. & Maglia, G. Single-molecule nanopore enzymology. Philos. Trans. R. Soc. Lond., B, Biol. Sci. 372, (2017).
Williams, L. S., Levdikov, V. M., Minakhin, L., Severinov, K. & Antson, A. A. 12-Fold symmetry of the putative portal protein from the Thermus thermophilus bacteriophage G20C determined by X-ray analysis. Acta Crystallogr Sect F Struct Biol Cryst Commun 69, 1239-1241 (2013).
Yamazaki, H. et al. Label-Free Single-Molecule Thermoscopy Using a Laser-Heated Nanopore. Nano Lett 17, 7067-7074 (2017).
Zhang, M. et al. Thermophoresis-Controlled Size-Dependent DNA Translocation through an Array of Nanopores. ACS Nano acsnano.8b00961 (2018). doi:10.1021/acsnano.8b00961.
Protein Data Bank in Europe: "PDB 5ngd structure summary Protein Data Bank in Europe (PDBe) EMBL-EBI", , Mar. 29, 2017 (Mar. 29, 2017), XP093132292, Retrieved from the Internet: URL:https://www.ebi.ac.uk/pdbe/entry/pdb/5ngd [retrieved on Feb. 16, 2024].
Extended European Search Report, EP Application No. 23170859.5 dated Mar. 6, 2023.
Hall, A, et al,"Hybrid pore formation by directed insertion of [alpha]-haemolysin into solid-state nanopores", vol. 5, No. 12, pp. 874-877 (2010).
International Search Report and Written Opinion for Int'l Application No. PCT/US2023/067412, entitled "Covalent tethering of portal protein into solid-state nanopores," consisting of 13 pages. Date of Mailing: Sep. 18, 2023.

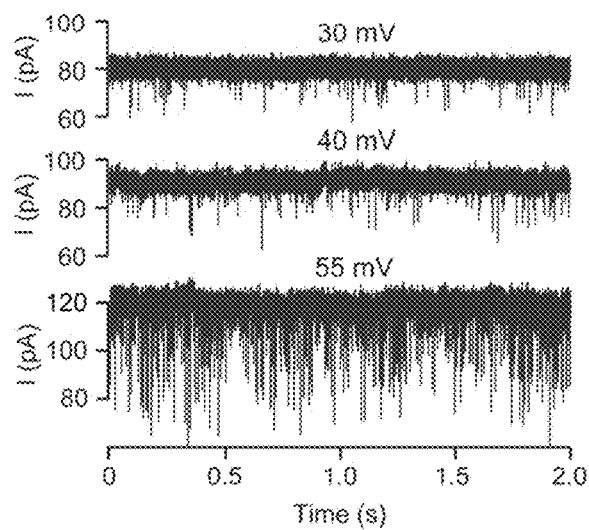
FIG. 11A
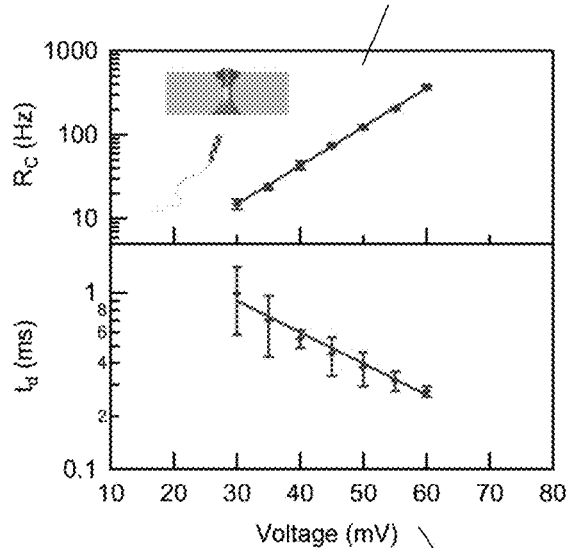
FIG. 11B
FIG. 11C

FIG. 12B (left)

FIG. 12C (left)

FIG. 12D (left)

LIPID-FREE ANCHORING OF THERMOPHILIC BACTERIOPHAGE G20c PORTAL ADAPTER INTO SOLID-STATE NANOPORES

RELATED APPLICATIONS

This application is a continuation of U.S. application Ser. No. 17/809,705, filed Jun. 29, 2022, which is a continuation of U.S. application Ser. No. 16/416,139, filed on May 17, 2019, which claims the benefit of U.S. Provisional Application No. 62/673,118, filed on May 17, 2018. The entire teachings of the above applications are incorporated herein by reference.

GOVERNMENT SUPPORT

This invention was made with government support under Grant No. 1645671 awarded by the National Science Foundation. The government has certain rights in the invention.

INCORPORATION BY REFERENCE OF MATERIAL IN XML

This application incorporates by reference the Sequence Listing contained in the following eXtensible Markup Language (XML) file being submitted concurrently herewith:
a) File name: 52002223-010_Corrected.xml; created Apr. 18, 2024, 86,957 Bytes in size.

BACKGROUND

Nanopore-based sensors are advancing the sensitivity and selectivity of single-molecule detection in molecular medicine and biotechnology. Conventional electrical and electro-optical sensing devices are based on either membrane protein pores supported in planar lipid bilayers or solid-state pores drilled into thin metallic membranes. While both types of nanosensors have been used in a variety of applications, each has inherent disadvantages that limit their use.

SUMMARY

Hybrid nanopores in accordance with an embodiment of the invention, comprising a protein pore supported within a solid-state membrane, combine the robust nature of solid-state membranes with the easily tunable and precise engineering of protein nanopores. A lipid-free hybrid nanopore comprises a water soluble and stable, modified portal protein of the *Thermus thermophilus* bacteriophage G20c, electrokinetically inserted into a larger nanopore in a solid-state membrane. The hybrid pore is stable and easy to fabricate, and exhibits low peripheral leakage, allowing sensing and discrimination among different types of biomolecules.

In one embodiment according to the invention, there is provided a sensor. The sensor comprises: a solid-state matrix comprising a solid-state pore opening; and a hydrophilic protein channel in a stable insertion fit within the solid-state pore opening, the hydrophilic protein channel comprising a protein nanopore channel.

In further, related embodiments, a protein forming at least part of the hydrophilic protein channel may comprise a modification of an amino acid sequence comprising SEQ ID NO: 1, the modification comprising one or more of: (i) a modification of an upper internal surface residue or a lower internal surface residue of the protein of the hydrophilic protein channel, the modification comprising an alteration of an electrostatic surface potential of an upper internal surface or a lower internal surface of SEQ ID NO: 1; (ii) a modification comprising an insertion of a cysteine residue into SEQ ID NO: 1 or a replacement of an amino acid residue of SEQ ID NO: 1 with a cysteine residue; (iii) a modification of a tunnel loop residue of the protein of the hydrophilic protein channel, the modification comprising an expansion of a narrowest constriction of a tunnel loop of SEQ ID NO: 1, a restriction of the narrowest constriction of the tunnel loop of SEQ ID NO: 1, or a removal of the narrowest constriction of the tunnel loop of SEQ ID NO: 1; (iv) a modification of a tunnel loop residue of the protein of the hydrophilic protein channel, the modification resulting in an alteration of an electrostatic charge property of a tunnel loop of SEQ ID NO: 1; (v) a modification which alters an external charge of the protein of the hydrophilic protein channel; (vi) a modification which promotes binding of the protein of the hydrophilic protein channel to the solid-state matrix; (vii) a modification which extends an N-terminus or a C-terminus of SEQ ID NO: 1 or an N-terminus or a C-terminus of a cleaved portion of SEQ ID NO: 1; and (viii) a deletion of an amino acid residue of at least one of a C-terminal region and an N-terminal region of SEQ ID NO: 1. The modification of SEQ ID NO: 1 may comprise a modification of a lower internal surface residue of the protein of the hydrophilic protein channel, the modification comprising the alteration of the electrostatic surface potential of the lower internal surface of SEQ ID NO: 1, and the protein of the hydrophilic protein channel may comprise SEQ ID NO: 27. The modification of SEQ ID NO: 1 may comprises a replacement of an amino acid residue of SEQ ID NO: 1 with a cysteine residue, and the protein of the hydrophilic protein channel may comprise SEQ ID NO: 11 or SEQ ID NO: 37. The modification of SEQ ID NO: 1 may comprise a modification of the tunnel loop residue of the protein of the hydrophilic protein channel, the modification comprising the expansion of the narrowest constriction of the tunnel loop of SEQ ID NO: 1, the restriction of the narrowest constriction of the tunnel loop of SEQ ID NO: 1, or the removal of the narrowest constriction of the tunnel loop of SEQ ID NO: 1, and the protein of the hydrophilic protein channel may comprise one of: SEQ ID NO: 15, SEQ ID NO: 17, SEQ ID NO: 21, SEQ ID NO: 23 and SEQ ID NO: 25. The modification of SEQ ID NO: 1 may comprise the modification in a tunnel loop residue of the protein of the hydrophilic protein channel, the modification resulting in the alteration of the electrostatic charge property of the tunnel loop of SEQ ID NO: 1, and the protein of the hydrophilic protein channel may comprise SEQ ID NO: 19. The modification of SEQ ID NO: 1 may comprise the modification which alters an external charge of the hydrophilic protein channel, and the protein of the hydrophilic protein channel may comprise one of: SEQ ID NO: 9 and SEQ ID NO: 13. The modification of SEQ ID NO: 1 may comprise the modification which promotes binding of the hydrophilic protein channel to the solid-state matrix, and the protein of the hydrophilic protein channel may comprise one of: SEQ ID NO: 29, SEQ ID NO: 31 and SEQ ID NO: 35. The modification of SEQ ID NO: 1 may comprise the modification which extends the N-terminus of the cleaved portion of SEQ ID NO: 1, and the protein of the hydrophilic protein channel may comprise SEQ ID NO: 33. The modification of SEQ ID NO: 1 may comprise the deletion of an amino acid residue of at least one of the C-terminal region and the N-terminal region of SEQ ID NO: 1, and the modification may comprise a modification of one of: SEQ ID NO: 3, SEQ ID NO: 5 and SEQ ID NO: 7. The protein of the hydrophilic protein channel may comprise a modification of SEQ ID NO: 1, the modification comprising a modification in one or more of: a wing loop residue, a tunnel loop residue, an upper internal surface residue, a lower internal surface residue, an external surface residue, a C-terminal residue, and an N-terminal residue.

In other related embodiments, the sensor may further comprise a voltage source configured to apply a voltage to an electrolyte solution on both sides of the solid-state matrix. The solid-state matrix may comprise at least one of: silicon, hafnium and nickel. The solid-state matrix may comprise at least one of: a silicon containing nitride, a silicon containing carbide and a silicon containing oxide. The solid-state matrix may comprise a thickness of less than about 30 nm. The solid-state pore opening may comprise a diameter of between about 5.4 nm and about 6 nm. The sensor may further comprise a coating on the solid-state matrix to promote binding of the solid-state matrix to a protein forming at least part of the hydrophilic protein channel. The coating may comprise a thiol-coupling compound; and may comprise a maleimide compound.

In other related embodiments, a protein forming at least part of the hydrophilic protein channel may comprise a modification of an amino acid sequence comprising SEQ ID NO: 1, the modification comprising one or more of: a modification of residue 328 of SEQ ID NO: 1, a modification of residue 189 of SEQ ID NO: 1, and a modification of residue 367 of SEQ ID NO: 1. A protein forming at least part of the hydrophilic protein channel may comprise a modification of SEQ ID NO: 1, the modification comprising one of: SEQ ID NO: 27; SEQ ID NO: 11; SEQ ID NO: 37; SEQ ID NO: 15, SEQ ID NO: 17, SEQ ID NO: 21, SEQ ID NO: 23, SEQ ID NO: 25, SEQ ID NO: 19, SEQ ID NO: 9, SEQ ID NO: 13, SEQ ID NO: 29, SEQ ID NO: 31, SEQ ID NO: 35, SEQ ID NO: 33, SEQ ID NO: 3, SEQ ID NO: 5, and SEQ ID NO: 7. A protein forming at least part of the hydrophilic protein channel may comprise a modification of SEQ ID NO: 1, the modification comprising one of: SEQ ID NO: 27; SEQ ID NO: 37; SEQ ID NO: 15, SEQ ID NO: 17, SEQ ID NO: 23, SEQ ID NO: 25, SEQ ID NO: 19, SEQ ID NO: 9, SEQ ID NO: 13, SEQ ID NO: 29, SEQ ID NO: 31, SEQ ID NO: 35, SEQ ID NO: 33, SEQ ID NO: 3, SEQ ID NO: 5, and SEQ ID NO: 7.

In some embodiments, where reference is made to modifications of SEQ ID NO: 1, it will be appreciated that a modification of a portal protein of the *Thermus thermophilus* bacteriophage G20c, can be used, or a modification of a portal protein from other bacteriophages (including other bacteriophages of *Thermus thermophilus*, and other bacteriophages) can be used. In one example, the portal protein of the *Thermus thermophilus* bacteriophage P23-45, or modifications of that portal protein, can be used. Likewise, in some embodiments, where reference is made to modification of SEQ ID NO: 2, it will be appreciated that other modifications of nucleic acids encoding for a portal protein of the *Thermus thermophilus* bacteriophage G20c, can be used, or those encoding for a modification of a portal protein from other bacteriophages (including other bacteriophages of *Thermus thermophilus*, and other bacteriophages) can be used. In one example, modifications of nucleic acids encoding for the portal protein of the *Thermus thermophilus* bacteriophage P23-45, or modifications of that portal protein, can be used.

In another embodiment according to the invention, there is provided a protein variant, the protein variant comprising a modification of an amino acid sequence comprising SEQ ID NO: 1, the modification comprising one or more of: (i) a modification of an upper internal surface residue or a lower internal surface residue of the protein variant, the modification comprising an alteration of an electrostatic surface potential of an upper internal surface or a lower internal surface of SEQ ID NO: 1; (ii) a modification comprising an insertion of a cysteine residue into SEQ ID NO: 1 or a replacement of an amino acid residue of SEQ ID NO: 1 with a cysteine residue; (iii) a modification of a tunnel loop residue of the protein variant, the modification comprising an expansion of a narrowest constriction of a tunnel loop of SEQ ID NO: 1, a restriction of the narrowest constriction of the tunnel loop of SEQ ID NO: 1, or a removal of the narrowest constriction of the tunnel loop of SEQ ID NO: 1; (iv) a modification of a tunnel loop residue of the protein variant, the modification resulting in an alteration of an electrostatic charge property of a tunnel loop of SEQ ID NO: 1; (v) a modification which alters an external charge of the protein variant; (vi) a modification which promotes binding of the protein variant to a solid-state matrix; (vii) a modification which extends an N-terminus or a C-terminus of SEQ ID NO: 1 or an N-terminus or a C-terminus of a cleaved portion of SEQ ID NO: 1; and (viii) a deletion of an amino acid residue of at least one of a C-terminal region and an N-terminal region of SEQ ID NO: 1.

In further, related embodiments, the modification of SEQ ID NO: 1 may comprise a modification of a lower internal surface residue of the protein variant, the modification comprising the alteration of the electrostatic surface potential of the lower internal surface of SEQ ID NO: 1, and the protein variant may comprise SEQ ID NO: 27. The modification of SEQ ID NO: 1 may comprise a replacement of an amino acid residue of SEQ ID NO: 1 with a cysteine residue, and the protein variant may comprise SEQ ID NO: 11 or SEQ ID NO: 37. The modification of SEQ ID NO: 1 may comprise a modification of the tunnel loop residue of the protein variant, the modification comprising the expansion of a narrowest constriction of a tunnel loop of SEQ ID NO: 1, the restriction of the narrowest constriction of the tunnel loop of SEQ ID NO: 1, or the removal of the narrowest constriction of the tunnel loop of SEQ ID NO: 1, and the protein variant may comprise one of: SEQ ID NO: 15, SEQ ID NO: 17, SEQ ID NO: 21, SEQ ID NO: 23, and SEQ ID NO: 25. The modification of SEQ ID NO: 1 may comprise the modification of a tunnel loop residue of the protein variant, the modification resulting in the alteration of the electrostatic charge property of the tunnel loop of SEQ ID NO: 1, and the protein variant may comprise SEQ ID NO: 19. The modification of SEQ ID NO: 1 may comprise the modification which alters the external charge of the protein variant, and the protein variant may comprise one of: SEQ ID NO: 9 and SEQ ID NO: 13. The modification of SEQ ID NO: 1 may comprise the modification which promotes binding of the protein variant to a solid-state matrix, and the protein variant may comprise one of: SEQ ID NO: 29, SEQ ID NO: 31 and SEQ ID NO: 35. The modification of SEQ ID NO: 1 may comprise the modification which extends the N-terminus of the cleaved portion of SEQ ID NO: 1, and the protein variant may comprise SEQ ID NO: 33. The modification of SEQ ID NO: 1 may comprise the deletion of an amino acid residue of at least one of the C-terminal region and the N-terminal region of SEQ ID NO: 1, and the modification may comprise a modification of one of: SEQ ID NO: 3, SEQ ID NO: 5 and SEQ ID NO: 7. The modification of SEQ ID NO: 1 may comprise a modification in one or more of: a wing loop residue, a tunnel loop residue, an upper internal surface residue, a lower internal surface residue, an external surface residue, a C-terminal residue, and an N-terminal residue.

In another embodiment according to the invention, there is provided a protein variant, the protein variant comprising a modification of an amino acid sequence comprising SEQ ID NO: 1, the modification comprising one of: SEQ ID NO: 27; SEQ ID NO: 11; SEQ ID NO: 37; SEQ ID NO: 15, SEQ ID NO: 17, SEQ ID NO: 21, SEQ ID NO: 23, SEQ ID NO: 25, SEQ ID NO: 19, SEQ ID NO: 9, SEQ ID NO: 13, SEQ ID NO: 29, SEQ ID NO: 31, SEQ ID NO: 35, SEQ ID NO: 33, SEQ ID NO: 3, SEQ ID NO: 5, and SEQ ID NO: 7.

In another embodiment according to the invention, there is provided a protein variant, the protein variant comprising a modification of an amino acid sequence comprising SEQ ID NO: 1, the modification comprising one of: SEQ ID NO: 27; SEQ ID NO: 37; SEQ ID NO: 15, SEQ ID NO: 17, SEQ ID NO: 23, SEQ ID NO: 25, SEQ ID NO: 19, SEQ ID NO: 9, SEQ ID NO: 13, SEQ ID NO: 29, SEQ ID NO: 31, SEQ ID NO: 35, SEQ ID NO: 33, SEQ ID NO: 3, SEQ ID NO: 5, and SEQ ID NO: 7.

In another embodiment according to the invention, there is provided a nucleic acid molecule comprising a modification of a nucleic acid sequence of SEQ ID NO: 2, the modification comprising one or more of: (i) a modification in a portion of the nucleic acid sequence that encodes an upper internal surface residue or a lower internal surface residue of a protein encoded by the nucleic acid sequence, the modification producing an alteration of an electrostatic surface potential of an upper internal surface or a lower internal surface of the protein encoded by the nucleic acid sequence; (ii) a modification comprising an insertion of a cysteine residue into a protein encoded by the nucleic acid sequence or a replacement of an amino acid residue of a protein encoded by the nucleic acid sequence with a cysteine residue; (iii) a modification to produce a modification of a tunnel loop residue of a protein encoded by the nucleic acid sequence, the modification in the tunnel loop residue comprising an expansion of a narrowest constriction of a tunnel loop of the protein encoded by the nucleic acid sequence, a restriction of the narrowest constriction of the tunnel loop of the protein encoded by the nucleic acid sequence, or a removal of the narrowest constriction of the tunnel loop of the protein encoded by the nucleic acid sequence; (iv) a modification to produce a modification of a tunnel loop residue of a protein encoded by the nucleic acid sequence, the modification resulting in an alteration of an electrostatic charge property of a tunnel loop of the protein encoded by the nucleic acid sequence; (v) a modification which alters an external charge of a protein encoded by the nucleic acid sequence; (vi) a modification which promotes binding of a protein encoded by the nucleic acid sequence to a solid-state matrix; (vii) a modification which extends an N-terminus or a C-terminus of a protein encoded by the nucleic acid sequence or an N-terminus or a C-terminus of a cleaved portion of the protein encoded by the nucleic acid sequence; and (viii) a deletion of an amino acid residue of at least one of a C-terminal region and an N-terminal region of a protein encoded by the nucleic acid sequence.

In further, related embodiments, the modification of SEQ ID NO: 2 may comprise a modification in the portion of the nucleic acid sequence that encodes the lower internal surface residue of the protein encoded by the nucleic acid sequence, the modification producing the alteration of the electrostatic surface potential of the lower internal surface of the protein encoded by the nucleic acid sequence, and the nucleic acid molecule may comprise SEQ ID NO: 28. The modification of SEQ ID NO: 2 may comprise the modification comprising an insertion of a cysteine residue into a protein encoded by the nucleic acid sequence or a replacement of an amino acid residue of a protein encoded by the nucleic acid sequence with a cysteine residue, and the nucleic acid molecule may comprise SEQ ID NO: 12 or SEQ ID NO: 38. The modification of SEQ ID NO: 2 may comprise the modification to produce a modification of a tunnel loop residue of the protein encoded by the nucleic acid sequence, the modification in the tunnel loop residue comprising the expansion of the narrowest constriction of the tunnel loop of the protein encoded by the nucleic acid sequence, the restriction of the narrowest constriction of the tunnel loop of the protein encoded by the nucleic acid sequence, or the removal of the narrowest constriction of the tunnel loop of the protein encoded by the nucleic acid sequence, and the nucleic acid molecule may comprise one of: SEQ ID NO: 16, SEQ ID NO: 18, SEQ ID NO: 22, SEQ ID NO: 24 and SEQ ID NO: 26. The modification of SEQ ID NO: 2 may comprise a modification to produce a modification of a tunnel loop residue of the protein encoded by the nucleic acid sequence, the modification resulting in the alteration of the electrostatic charge property of the tunnel loop of the protein encoded by the nucleic acid sequence, and the nucleic acid molecule may comprise SEQ ID NO: 20. The modification of SEQ ID NO: 2 may comprise the modification which alters the external charge of the protein encoded by the nucleic acid sequence, and the nucleic acid molecule may comprise one of: SEQ ID NO: 10 and SEQ ID NO: 14. The modification of SEQ ID NO: 2 may comprise the modification which promotes binding of the protein encoded by the nucleic acid sequence to the solid-state matrix, and the nucleic acid molecule may comprise one of: SEQ ID NO: 30, SEQ ID NO: 32 and SEQ ID NO: 36. The modification of SEQ ID NO: 2 may comprise the modification which extends the N-terminus of the cleaved portion of the protein encoded by the nucleic acid sequence, and the nucleic acid molecule may comprise SEQ ID NO: 34. The modification of SEQ ID NO: 2 may comprise a deletion of an amino acid residue of at least one of the C-terminal region and the N-terminal region of the protein encoded by the nucleic acid sequence, and the nucleic acid molecule may comprise one of: SEQ ID NO: 4, SEQ ID NO: 6 and SEQ ID NO: 8. The modification of SEQ ID NO: 2 may comprise a modification to produce a modification in one or more of: a wing loop residue, a tunnel loop residue, an upper internal surface residue, a lower internal surface residue, an external surface residue, a C-terminal end residue, and an N-terminal end residue; of a protein encoded by the nucleic acid sequence.

In another embodiment according to the invention, there is provided a nucleic acid molecule comprising a modification of a nucleic acid sequence of SEQ ID NO: 2, the nucleic acid molecule comprising one of: SEQ ID NO: 28; SEQ ID NO: 12; SEQ ID NO: 38; SEQ ID NO: 16, SEQ ID NO: 18, SEQ ID NO: 22, SEQ ID NO: 24, SEQ ID NO: 26, SEQ ID NO: 20, SEQ ID NO: 10, SEQ ID NO: 14, SEQ ID NO: 30, SEQ ID NO: 32, SEQ ID NO: 36, SEQ ID NO: 34, SEQ ID NO: 4, SEQ ID NO: 6, and SEQ ID NO: 8.

In another embodiment according to the invention, there is provided a nucleic acid molecule comprising a modification of a nucleic acid sequence of SEQ ID NO: 2, the nucleic acid molecule comprising one of: SEQ ID NO: 28; SEQ ID NO: 38; SEQ ID NO: 16, SEQ ID NO: 18, SEQ ID NO: 24, SEQ ID NO: 26, SEQ ID NO: 20, SEQ ID NO: 10, SEQ ID NO: 14, SEQ ID NO: 30, SEQ ID NO: 32, SEQ ID NO: 36, SEQ ID NO: 34, SEQ ID NO: 4, SEQ ID NO: 6, and SEQ ID NO: 8.

In another embodiment according to the invention, there is provided a method of sensing a biomolecule, the method comprising: applying a voltage to an electrolyte on both sides of a solid-state matrix, the solid-state matrix comprising a solid-state pore opening, and a hydrophilic protein channel in a stable insertion fit within the solid-state pore opening, the hydrophilic protein channel comprising a protein nanopore channel; and measuring a voltage change produced by passage of the biomolecule through the protein nanopore channel.

In further, related embodiments, the biomolecule may comprise one or more of: a protein, a nucleic acid, a biopolymer and an organic molecule. The biomolecule may comprise single-stranded DNA, double-stranded DNA or RNA. A protein forming at least part of the hydrophilic protein channel may comprise a modification of an amino acid sequence comprising SEQ ID NO: 1, the modification comprising one or more of: (i) a modification of an upper internal surface residue or a lower internal surface residue of the protein of the hydrophilic protein channel, the modification comprising an alteration of an electrostatic surface potential of an upper internal surface or a lower internal surface of SEQ ID NO: 1; (ii) a modification comprising an insertion of a cysteine residue into SEQ ID NO: 1 or a replacement of an amino acid residue of SEQ ID NO: 1 with a cysteine residue; (iii) a modification of a tunnel loop residue of the protein of the hydrophilic protein channel, the modification comprising an expansion of a narrowest constriction of a tunnel loop of SEQ ID NO: 1, a restriction of the narrowest constriction of the tunnel loop of SEQ ID NO: 1, or a removal of the narrowest constriction of the tunnel loop of SEQ ID NO: 1; (iv) a modification of a tunnel loop residue of the protein of the hydrophilic protein channel, the modification resulting in an alteration of an electrostatic charge property of a tunnel loop of SEQ ID NO: 1; (v) a modification which alters an external charge of the protein of the hydrophilic protein channel; (vi) a modification which promotes binding of the protein of the hydrophilic protein channel to the solid-state matrix; (vii) a modification which extends an N-terminus or a C-terminus of SEQ ID NO: 1 or an N-terminus or a C-terminus of a cleaved portion of SEQ ID NO: 1; and (viii) a deletion of an amino acid residue of at least one of a C-terminal region and an N-terminal region of SEQ ID NO: 1. The modification of SEQ ID NO: 1 may comprise a modification of a lower internal surface residue of the protein of the hydrophilic protein channel, the modification comprising the alteration of the electrostatic surface potential of the lower internal surface of SEQ ID NO: 1, and the protein of the hydrophilic protein channel may comprise SEQ ID NO: 27. The modification of SEQ ID NO: 1 may comprise a replacement of an amino acid residue of SEQ ID NO: 1 with a cysteine residue, and the protein of the hydrophilic protein channel may comprise SEQ ID NO: 11 or SEQ ID NO: 37. The modification of SEQ ID NO: 1 may comprise a modification of the tunnel loop residue of the protein of the hydrophilic protein channel, the modification comprising the expansion of the narrowest constriction of the tunnel loop of SEQ ID NO: 1, the restriction of the narrowest constriction of the tunnel loop of SEQ ID NO: 1, or the removal of the narrowest constriction of the tunnel loop of SEQ ID NO: 1, and the protein of the hydrophilic protein channel may comprise one of: SEQ ID NO: 15, SEQ ID NO: 17, SEQ ID NO: 21, SEQ ID NO: 23, and SEQ ID NO: 25. The modification of SEQ ID NO: 1 may comprise the modification in a tunnel loop residue of the protein of the hydrophilic protein channel, the modification resulting in the alteration of the electrostatic charge property of the tunnel loop of SEQ ID NO: 1, and the protein of the hydrophilic protein channel may comprise SEQ ID NO: 19. The modification of SEQ ID NO: 1 may comprise the modification which alters an external charge of the hydrophilic protein channel, and the protein of the hydrophilic protein channel may comprise one of: SEQ ID NO: 9 and SEQ ID NO: 13. The modification of SEQ ID NO: 1 may comprise the modification which promotes binding of the protein of the hydrophilic protein channel to the solid-state matrix, and the protein of the hydrophilic protein channel may comprises one of: SEQ ID NO: 29, SEQ ID NO: 31 and SEQ ID NO: 35. The modification of SEQ ID NO: 1 may comprise the modification to extend the N-terminal of the cleaved portion of SEQ ID NO: 1, and the protein of the hydrophilic protein channel may comprise SEQ ID NO: 33. The modification of SEQ ID NO: 1 may comprise the deletion of an amino acid residue of at least one of the C-terminal region and the N-terminal region of SEQ ID NO: 1, and the modification may comprise a modification of one of: SEQ ID NO: 3, SEQ ID NO: 5 and SEQ ID NO: 7. The protein of the hydrophilic protein channel may comprise a modification of SEQ ID NO: 1, the modification comprising a modification in one or more of: a wing loop residue, a tunnel loop residue, an upper internal surface residue, a lower internal surface residue, an external surface residue, a C-terminal residue, and an N-terminal residue. A protein forming at least part of the hydrophilic protein channel may comprise a modification of SEQ ID NO: 1, the modification comprising one or more of: a modification of residue 328 of SEQ ID NO: 1, a modification of residue 189 of SEQ ID NO: 1, and a modification of residue 367 of SEQ ID NO: 1. A protein forming at least part of the hydrophilic protein channel may comprise a modification of SEQ ID NO: 1, the modification comprising one of: SEQ ID NO: 27; SEQ ID NO: 11; SEQ ID NO: 37; SEQ ID NO: 15, SEQ ID NO: 17, SEQ ID NO: 21, SEQ ID NO: 23, SEQ ID NO: 25, SEQ ID NO: 19, SEQ ID NO: 9, SEQ ID NO: 13, SEQ ID NO: 29, SEQ ID NO: 31, SEQ ID NO: 35, SEQ ID NO: 33, SEQ ID NO: 3, SEQ ID NO: 5, and SEQ ID NO: 7. A protein forming at least part of the hydrophilic protein channel may comprise a modification of SEQ ID NO: 1, the modification comprising one of: SEQ ID NO: 27; SEQ ID NO: 37; SEQ ID NO: 15, SEQ ID NO: 17, SEQ ID NO: 23, SEQ ID NO: 25, SEQ ID NO: 19, SEQ ID NO: 9, SEQ ID NO: 13, SEQ ID NO: 29, SEQ ID NO: 31, SEQ ID NO: 35, SEQ ID NO: 33, SEQ ID NO: 3, SEQ ID NO: 5, and SEQ ID NO: 7.

In other, related embodiments, the solid-state matrix may comprise at least one of: silicon, hafnium and nickel. The solid-state matrix may comprise at least one of: a silicon containing nitride, a silicon containing carbide and a silicon containing oxide. The solid-state matrix may comprise a thickness of less than about 30 nm. The solid-state pore opening may comprise a diameter of between about 5.4 nm and about 6 nm. The solid-state matrix may comprise a coating to promote binding of the solid-state matrix to a protein forming at least part of the hydrophilic protein channel. The coating may comprise a thiol-coupling compound. The coating may comprise a maleimide compound.

In another embodiment according to the invention, there is provided a method of manufacturing a sensor, the method comprising: applying at least one of a voltage and a pressure to an electrolyte solution on both sides of a solid-state matrix comprising a solid-state pore opening, the electrolyte solution comprising a hydrophilic protein; and as a result of the applying of the at least one of the voltage and the pressure, forming a stable insertion fit of a hydrophilic protein channel comprising the hydrophilic protein within the solid-state pore opening, the hydrophilic protein channel comprising a protein nanopore channel.

In further, related embodiments, the hydrophilic protein of the hydrophilic protein channel may comprise a modification of an amino acid sequence comprising SEQ ID NO: 1, the modification comprising one or more of: (i) a modification of an upper internal surface residue or a lower internal surface residue of the protein of the hydrophilic protein channel, the modification comprising an alteration of an electrostatic surface potential of an upper internal surface or a lower internal surface of SEQ ID NO: 1; (ii) a modification comprising an insertion of a cysteine residue into SEQ ID NO: 1 or a replacement of an amino acid residue of SEQ ID NO: 1 with a cysteine residue; (iii) a modification of a tunnel loop residue of the protein of the hydrophilic protein channel, the modification comprising an expansion of a narrowest constriction of a tunnel loop of SEQ ID NO: 1, a restriction of the narrowest constriction of the tunnel loop of SEQ ID NO: 1, or a removal of the narrowest constriction of the tunnel loop of SEQ ID NO: 1; (iv) a modification of a tunnel loop residue of the protein of the hydrophilic protein channel, the modification resulting in an alteration of an electrostatic charge property of a tunnel loop of SEQ ID NO: 1; (v) a modification which alters an external charge of the protein of the hydrophilic protein channel; (vi) a modification which promotes binding of the protein of the hydrophilic protein channel to the solid-state matrix; (vii) a modification which extends an N-terminus or a C-terminus of SEQ ID NO: 1 or an N-terminus or a C-terminus of a cleaved portion of SEQ ID NO: 1; and (viii) a deletion of an amino acid residue of at least one of a C-terminal region and an N-terminal region of SEQ ID NO: 1. The modification of SEQ ID NO: 1 may comprise a modification of the lower internal surface residue of the protein of the hydrophilic protein channel, the modification comprising the alteration of the electrostatic surface potential of the lower internal surface of SEQ ID NO: 1, and the protein of the hydrophilic protein channel may comprise SEQ ID NO: 27. The modification of SEQ ID NO: 1 may comprise a replacement of an amino acid residue of SEQ ID NO: 1 with a cysteine residue, and the protein of the hydrophilic protein channel may comprise SEQ ID NO: 11 or SEQ ID NO: 37. The modification of SEQ ID NO: 1 may comprise a modification of the tunnel loop residue of the protein of the hydrophilic protein channel, the modification comprising the expansion of the narrowest constriction of the tunnel loop of SEQ ID NO: 1, the restriction of the narrowest constriction of the tunnel loop of SEQ ID NO: 1, or the removal of the narrowest constriction of the tunnel loop of SEQ ID NO: 1, and the protein of the hydrophilic protein channel may comprise one of: SEQ ID NO: 15, SEQ ID NO: 17, SEQ ID NO: 21, SEQ ID NO: 23, and SEQ ID NO: 25. The modification of SEQ ID NO: 1 may comprise the modification in a tunnel loop residue of the protein of the hydrophilic protein channel, the modification resulting in the alteration of the electrostatic charge property of the tunnel loop of SEQ ID NO: 1, and the protein of the hydrophilic protein channel may comprise SEQ ID NO: 19. The modification of SEQ ID NO: 1 may comprise the modification which alters the external charge of the hydrophilic protein channel, and the protein of the hydrophilic protein channel may comprise one of: SEQ ID NO: 9 and SEQ ID NO: 13. The modification of SEQ ID NO: 1 may comprise the modification which promotes binding of the protein of the hydrophilic protein channel to the solid-state matrix, and the protein of the hydrophilic protein channel may comprise one of: SEQ ID NO: 29, SEQ ID NO: 31 and SEQ ID NO: 35. The modification of SEQ ID NO: 1 may comprise the modification which extends the N-terminus of the cleaved portion of SEQ ID NO: 1, and the protein of the hydrophilic protein channel may comprise SEQ ID NO: 33. The modification of SEQ ID NO: 1 may comprise the deletion of an amino acid residue of at least one of the C-terminal region and the N-terminal region of SEQ ID NO: 1, and the modification may comprise a modification of one of: SEQ ID NO: 3, SEQ ID NO: 5 and SEQ ID NO: 7. The protein of the hydrophilic protein channel may comprise a modification of SEQ ID NO: 1, the modification comprising a modification in one or more of: a wing loop residue, a tunnel loop residue, an upper internal surface residue, a lower internal surface residue, an external surface residue, a C-terminal residue, and an N-terminal residue. The protein of the hydrophilic protein channel may comprise a modification of SEQ ID NO: 1, the modification comprising one or more of: a modification of residue 328 of SEQ ID NO: 1, a modification of residue 189 of SEQ ID NO: 1, and a modification of residue 367 of SEQ ID NO: 1. A protein forming at least part of the hydrophilic protein channel may comprise a modification of SEQ ID NO: 1, the modification comprising one of: SEQ ID NO: 27; SEQ ID NO: 11; SEQ ID NO: 37; SEQ ID NO: 15, SEQ ID NO: 17, SEQ ID NO: 21, SEQ ID NO: 23, SEQ ID NO: 25, SEQ ID NO: 19, SEQ ID NO: 9, SEQ ID NO: 13, SEQ ID NO: 29, SEQ ID NO: 31, SEQ ID NO: 35, SEQ ID NO: 33, SEQ ID NO: 3, SEQ ID NO: 5, and SEQ ID NO: 7. A protein forming at least part of the hydrophilic protein channel may comprise a modification of SEQ ID NO: 1, the modification comprising one of: SEQ ID NO: 27; SEQ ID NO: 37; SEQ ID NO: 15, SEQ ID NO: 17, SEQ ID NO: 23, SEQ ID NO: 25, SEQ ID NO: 19, SEQ ID NO: 9, SEQ ID NO: 13, SEQ ID NO: 29, SEQ ID NO: 31, SEQ ID NO: 35, SEQ ID NO: 33, SEQ ID NO: 3, SEQ ID NO: 5, and SEQ ID NO: 7.

In other related embodiments, the solid-state matrix may comprise at least one of: silicon, hafnium and nickel. The solid-state matrix may comprise at least one of: a silicon containing nitride, a silicon containing carbide and a silicon containing oxide. The solid-state matrix may comprise a thickness of less than about 30 nm. The solid-state pore opening may comprise a diameter of between about 5.4 nm and about 6 nm. The method may further comprise coating the solid-state matrix to promote binding of the solid-state matrix to a protein forming at least part of the hydrophilic protein channel. Coating the solid-state matrix may comprise applying a thiol-coupling compound to the solid-state matrix. Coating the solid-state matrix may comprise applying a coating comprising a maleimide compound to the solid-state matrix.

In another embodiment according to the invention, there is provided a protein variant encoded by a modification of a nucleic acid sequence of SEQ ID NO: 2, the modification comprising one or more of: (i) a modification in a portion of the nucleic acid sequence that encodes an upper internal surface residue or a lower internal surface residue of the protein variant encoded by the nucleic acid sequence, the modification producing an alteration of an electrostatic surface potential of an upper internal surface or a lower internal surface of the protein variant encoded by the nucleic acid sequence; (ii) a modification comprising an insertion of a cysteine residue into the protein variant encoded by the nucleic acid sequence or a replacement of an amino acid residue of the protein variant encoded by the nucleic acid sequence with a cysteine residue; (iii) a modification to produce a modification of a tunnel loop residue of the protein variant encoded by the nucleic acid sequence, the modification in the tunnel loop residue comprising an expansion of a narrowest constriction of a tunnel loop of the protein variant encoded by the nucleic acid sequence, a restriction of the narrowest constriction of the tunnel loop of the protein variant encoded by the nucleic acid sequence, or a removal of the narrowest constriction of the tunnel loop of the protein variant encoded by the nucleic acid sequence; (iv) a modification to produce a modification of a tunnel loop residue of the protein variant encoded by the nucleic acid sequence, the modification resulting in an alteration of an electrostatic charge property of a tunnel loop of the protein variant encoded by the nucleic acid sequence; (v) a modification which alters an external charge of the protein variant encoded by the nucleic acid sequence; (vi) a modification which promotes binding of the protein variant encoded by the nucleic acid sequence to a solid-state matrix; (vii) a modification which extends an N-terminus or a C-terminus of the protein variant encoded by the nucleic acid sequence or an N-terminus or a C-terminus of a cleaved portion of the protein variant encoded by the nucleic acid sequence; and (viii) a deletion of an amino acid residue of at least one of a C-terminal region and an N-terminal region of the protein variant encoded by the nucleic acid sequence.

In further, related embodiments, the modification of SEQ ID NO: 2 may comprise a modification in a portion of the nucleic acid sequence that encodes the lower internal surface residue of the protein variant encoded by the nucleic acid sequence, the modification producing the alteration of the electrostatic surface potential of the lower internal surface of the protein variant encoded by the nucleic acid sequence, and the modification of the nucleic acid sequence may comprise SEQ ID NO: 28. The modification of SEQ ID NO: 2 may comprise a replacement of an amino acid residue of the protein variant encoded by the nucleic acid sequence with the cysteine residue, and the modification of the nucleic acid sequence may comprise SEQ ID NO: 12 or SEQ ID NO: 38. The modification of SEQ ID NO: 2 may comprise the modification to produce a modification of a tunnel loop residue of the protein variant encoded by the nucleic acid sequence, the modification in the tunnel loop residue comprising the expansion of the narrowest constriction of the tunnel loop of the protein variant encoded by the nucleic acid sequence, the restriction of the narrowest constriction of the tunnel loop of the protein variant encoded by the nucleic acid sequence, or the removal of the narrowest constriction of the tunnel loop of the protein variant encoded by the nucleic acid sequence, and the modification of the nucleic acid sequence may comprise one of: SEQ ID NO: 16, SEQ ID NO: 18, SEQ ID NO: 22, SEQ ID NO: 24, and SEQ ID NO: 26. The modification of SEQ ID NO: 2 may comprise the modification to produce a modification of a tunnel loop residue of the protein variant encoded by the nucleic acid sequence, the modification resulting in an alteration of an electrostatic charge property of a tunnel loop of the protein variant encoded by the nucleic acid sequence, and the modification of the nucleic acid sequence may comprise SEQ ID NO: 20. The modification of SEQ ID NO: 2 may comprise the modification which alters the external charge of the protein variant encoded by the nucleic acid sequence, and the modification of the nucleic acid sequence may comprise one of: SEQ ID NO: 10 and SEQ ID NO: 14. The modification of SEQ ID NO: 2 may comprise the modification which promotes binding of the protein variant encoded by the nucleic acid sequence to the solid-state matrix, and the modification of the nucleic acid sequence may comprise one of: SEQ ID NO: 30, SEQ ID NO: 32 and SEQ ID NO: 36. The modification of SEQ ID NO: 2 may comprise the modification which extends the N-terminus of the cleaved portion of the protein variant encoded by the nucleic acid sequence, and the modification of the nucleic acid sequence may comprise SEQ ID NO: 34. The modification of SEQ ID NO: 2 may comprise a deletion of an amino acid residue of at least one of a C-terminal region and an N-terminal region of the protein variant encoded by the nucleic acid sequence, and the modification of the nucleic acid sequence may comprise one of: SEQ ID NO: 4, SEQ ID NO: 6 and SEQ ID NO: 8. The modification of SEQ ID NO: 2 may comprise a modification to produce a modification in one or more of: a wing loop residue, a tunnel loop residue, an upper internal surface residue, a lower internal surface residue, an external surface residue, a C-terminal residue, and an N-terminal residue; of the protein variant encoded by the modification of the nucleic acid sequence.

In another embodiment according to the invention, there is provided a protein variant encoded by a modification of a nucleic acid sequence of SEQ ID NO: 2, the modification comprising one or more of: SEQ ID NO: 28; SEQ ID NO: 12; SEQ ID NO: 38; SEQ ID NO: 16, SEQ ID NO: 18, SEQ ID NO: 22, SEQ ID NO: 24, SEQ ID NO: 26, SEQ ID NO: 20, SEQ ID NO: 10, SEQ ID NO: 14, SEQ ID NO: 30, SEQ ID NO: 32, SEQ ID NO: 36, SEQ ID NO: 34, SEQ ID NO: 4, SEQ ID NO: 6, and SEQ ID NO: 8.

In another embodiment according to the invention, there is provided a protein variant encoded by a modification of a nucleic acid sequence of SEQ ID NO: 2, the modification comprising one or more of: SEQ ID NO: 28; SEQ ID NO: 38; SEQ ID NO: 16, SEQ ID NO: 18, SEQ ID NO: 24, SEQ ID NO: 26, SEQ ID NO: 20, SEQ ID NO: 10, SEQ ID NO: 14, SEQ ID NO: 30, SEQ ID NO: 32, SEQ ID NO: 36, SEQ ID NO: 34, SEQ ID NO: 4, SEQ ID NO: 6, and SEQ ID NO: 8.

In another embodiment according to the invention, there is provided a vector comprising a modification of a nucleic acid sequence of SEQ ID NO: 2, the modification comprising one or more of: (i) a modification in a portion of the nucleic acid sequence that encodes an upper internal surface residue or a lower internal surface residue of a protein encoded by the nucleic acid sequence, the modification producing an alteration of an electrostatic surface potential of an upper internal surface or a lower internal surface of the protein encoded by the nucleic acid sequence; (ii) a modification comprising an insertion of a cysteine residue into a protein encoded by the nucleic acid sequence or a replacement of an amino acid residue of a protein encoded by the nucleic acid sequence with a cysteine residue; (iii) a modification to produce a modification of a tunnel loop residue of a protein encoded by the nucleic acid sequence, the modification of the tunnel loop residue comprising an expansion of a narrowest constriction of a tunnel loop of the protein encoded by the nucleic acid sequence, a restriction of the narrowest constriction of the tunnel loop of the protein encoded by the nucleic acid sequence, or a removal of the narrowest constriction of the tunnel loop of the protein encoded by the nucleic acid sequence; (iv) a modification to produce a modification of a tunnel loop residue of a protein encoded by the nucleic acid sequence, the modification resulting in an alteration of an electrostatic charge property of a tunnel loop of the protein encoded by the nucleic acid sequence; (v) a modification which alters an external charge of a protein encoded by the nucleic acid sequence; (vi) a modification which promotes binding of a protein encoded by the nucleic acid sequence to a solid-state matrix; (vii) a modification which extends an N-terminus or a C-terminus of a protein encoded by the nucleic acid sequence or an N-terminus or a C-terminus of a cleaved portion of the protein encoded by the nucleic acid sequence; and (viii) a deletion of an amino acid residue of at least one of a C-terminal region and an N-terminal region of a protein encoded by the nucleic acid sequence.

In further related embodiments, the modification of SEQ ID NO: 2 may comprise a modification in the portion of the nucleic acid sequence that encodes the lower internal surface residue of the protein encoded by the nucleic acid sequence, the modification producing the alteration of the electrostatic surface potential of the lower internal surface of the protein encoded by the nucleic acid sequence, and the modification of the nucleic acid sequence may comprise SEQ ID NO: 28. The modification of SEQ ID NO: 2 may comprise a modification comprising an insertion of a cysteine residue into the protein encoded by the nucleic acid sequence or a replacement of an amino acid residue of a protein encoded by the nucleic acid sequence with the cysteine residue, and the modification of the nucleic acid sequence may comprise one of: SEQ ID NO: 12 and SEQ ID NO: 38. The modification of SEQ ID NO: 2 may comprise a modification to produce a modification of a tunnel loop residue of the protein encoded by the nucleic acid sequence, the modification in the tunnel loop residue comprising the expansion of the narrowest constriction of the tunnel loop of the protein encoded by the nucleic acid sequence, the restriction of the narrowest constriction of the tunnel loop of the protein encoded by the nucleic acid sequence, or the removal of the narrowest constriction of the tunnel loop of the protein encoded by the nucleic acid sequence, and the modification of the nucleic acid sequence may comprise one of: SEQ ID NO: 16, SEQ ID NO: 18, SEQ ID NO: 22, SEQ ID NO: 24, and SEQ ID NO: 26. The modification of SEQ ID NO: 2 may comprise a modification to produce a modification of the tunnel loop residue of the protein encoded by the nucleic acid sequence, the modification resulting in the alteration of the electrostatic charge property of the tunnel loop of the protein encoded by the nucleic acid sequence, and the modification of the nucleic acid sequence may comprise SEQ ID NO: 20. The modification of SEQ ID NO: 2 may comprise the modification which alters the external charge of the protein encoded by the nucleic acid sequence, and the modification of the nucleic acid sequence may comprise one of: SEQ ID NO: 10 and SEQ ID NO: 14. The modification of SEQ ID NO: 2 may comprise the modification which promotes binding of the protein encoded by the nucleic acid sequence to the solid-state matrix, and the modification of the nucleic acid sequence may comprise one of: SEQ ID NO: 30, SEQ ID NO: 32 and SEQ ID NO: 36. The modification of SEQ ID NO: 2 may comprise the modification which extends the N-terminus of the cleaved portion of the protein encoded by the nucleic acid sequence, and the modification of the nucleic acid sequence may comprise SEQ ID NO: 34. The modification of SEQ ID NO: 2 may comprise the deletion of the amino acid residue of at least one of the C-terminal region and the N-terminal region of the protein encoded by the nucleic acid sequence, and the modification of the nucleic acid sequence may comprise one of: SEQ ID NO: 4, SEQ ID NO: 6 and SEQ ID NO: 8. The modification of SEQ ID NO: 2 may comprise a modification to produce a modification in one or more of: a wing loop residue, a tunnel loop residue, an upper internal surface residue, a lower internal surface residue, an external surface residue, a C-terminal residue, and an N-terminal residue; of a protein encoded by the modification of the nucleic acid sequence.

In another embodiment according to the invention, there is provided a vector comprising a modification of a nucleic acid sequence of SEQ ID NO: 2, the modification comprising one or more of: SEQ ID NO: 28; SEQ ID NO: 12; SEQ ID NO: 38; SEQ ID NO: 16, SEQ ID NO: 18, SEQ ID NO: 22, SEQ ID NO: 24, SEQ ID NO: 26, SEQ ID NO: 20, SEQ ID NO: 10, SEQ ID NO: 14, SEQ ID NO: 30, SEQ ID NO: 32, SEQ ID NO: 36, SEQ ID NO: 34, SEQ ID NO: 4, SEQ ID NO: 6, and SEQ ID NO: 8.

In another embodiment according to the invention, there is provided a vector comprising a modification of a nucleic acid sequence of SEQ ID NO: 2, the modification comprising one or more of: SEQ ID NO: 28; SEQ ID NO: 38; SEQ ID NO: 16, SEQ ID NO: 18, SEQ ID NO: 24, SEQ ID NO: 26, SEQ ID NO: 20, SEQ ID NO: 10, SEQ ID NO: 14, SEQ ID NO: 30, SEQ ID NO: 32, SEQ ID NO: 36, SEQ ID NO: 34, SEQ ID NO: 4, SEQ ID NO: 6, and SEQ ID NO: 8.

In other embodiments, there is provided a cell comprising any of the vectors taught herein.

In another embodiment according to the invention, there is provided a nucleic acid sequence encoding any of the protein variants taught herein.

In further, related embodiments, the cell may be any of the vectors taught in the foregoing paragraphs.

BRIEF DESCRIPTION OF THE DRAWINGS

The patent or application file contains at least one drawing executed in color. Copies of this patent or patent application publication with color drawings will be provided by the Office upon request and payment of the necessary fee.

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

FIG. 2 shows a slice through the middle of molecular surface colored according to charge from red (−1 kT/e) to blue (+1 kT/e).

FIG. 6 is a graph of a typical current profile over time recorded through a 5.5 nm SS pore at +100 mV. After injection of 0.1 nmol of portal protein, short current drops are detected, interpreted as portal collisions with the solid-state nanopore.

FIG. 7 is a graph of a representative current vs time trace recorded for a 5.4 nm SS nanopore at +80 mV, showing stable insertion of a portal protein.

FIG. 8 is a graph of current as a function of the applied voltage for a 5.5 nm SS pore recorded before (red/cross markers, with a higher slope) and after insertion of a portal protein (purple/triangle, with a lower slope).

FIG. 9 is a graph of current noise analysis of a 5.5 nm diameter solid-state nanopore before (red, top curve) and after insertion of a portal protein (purple, bottom curve).

FIG. 10 is a graph of conductance of solid-state nanopore vs conductance of portal hybrid pore (n=32 for CD/N hybrids and n=15 for CGG hybrids). Experiments were performed in 0.5 M NaCl, 20 mM Tris pH 7.5.

FIGS. 11A-11C are graphs showing dynamics of TPX2 peptide transport, in experiments in accordance with an embodiment of the invention. FIG. 11A is a graph showing a current vs time trace recorded through a hybrid pore at +30, +40 and +55 mV in the presence of 10.3 µM TPX2 peptide. FIG. 11B is a semi-log plot of the event frequency as a function of the applied voltage. The line is an exponential fit to the equation. FIG. 11C is a semi-log plot of the peptide dwell time as a function of the applied voltage. The lines in FIGS. 11B and 11C are exponential fits. Experiments were performed in 0.5 M NaCl, 20 mM Tris pH 7.5.

FIGS. 12A-12E are graphs illustrating sensing of different biopolymers using a hybrid nanopore, in experiments in accordance with an embodiment of the invention. Current vs time trace recorded through the hybrid pore at +60 mV in the presence of (FIG. 12A) 36.0 µM insulin, (FIG. 12B) 7.7 µM DNA hairpin, (FIG. 12C) 10.3 µM TPX2 peptide and (FIG. 12D) 16.6 µM ssDNA. The data in (FIG. 12A) were filtered at 10 kHz (grey) or 0.5 kHz (green). FIG. 12E is a scatter plot of ΔI vs dwell time for the DNA hairpin (red), the peptide (purple) and the ssDNA (orange). Experiments were performed in 0.5 M NaCl, 20 mM Tris pH 7.5.

DETAILED DESCRIPTION

Figure 1:
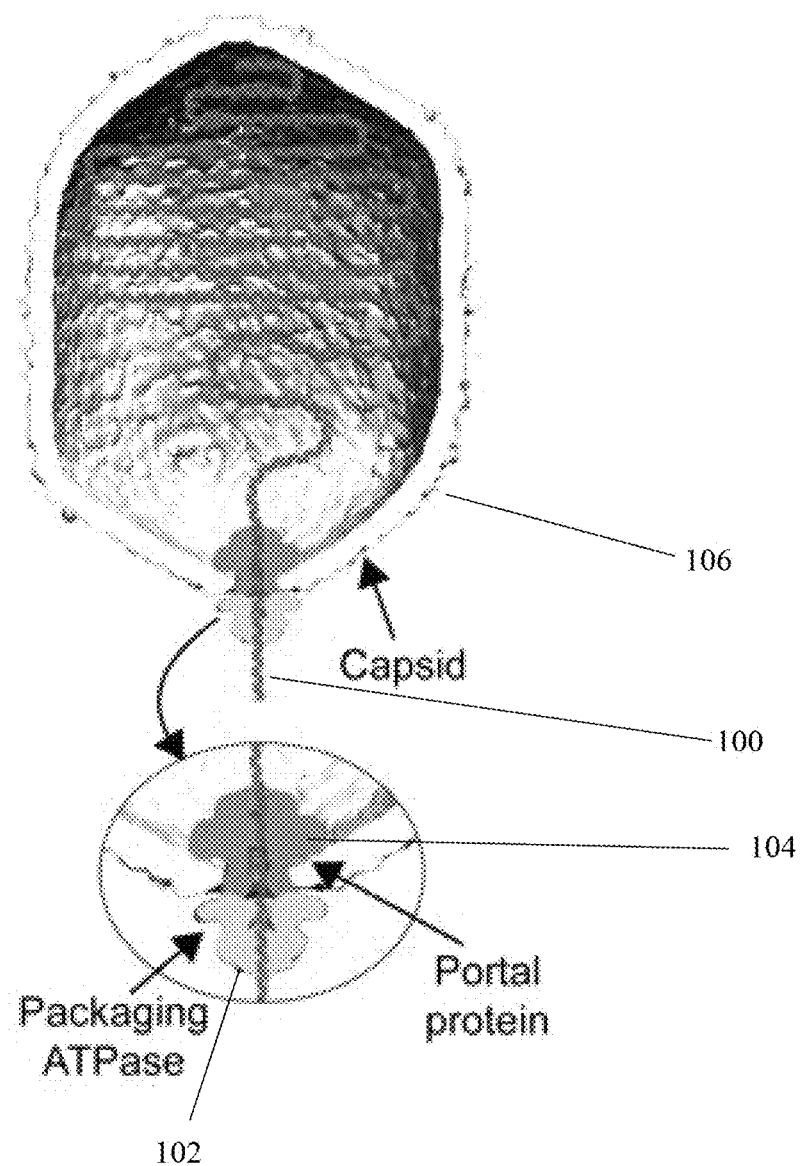
FIG. 1 is a schematic diagram of the DNA packaging machine of a dsDNA virus.

A description of example embodiments follows.

Hybrid nanopores in accordance with an embodiment of the invention, comprising a protein pore supported within a solid-state membrane, combine the robust nature of solid-state membranes with the easily tunable and precise engineering of protein nanopores. A lipid-free hybrid nanopore comprises a water soluble and stable, modified portal protein of the *Thermus thermophilus* bacteriophage G20c, electrokinetically inserted into a larger nanopore in a solid-state membrane. The hybrid pore is stable and easy to fabricate, and exhibits low peripheral leakage, allowing sensing and discrimination among different types of biomolecules.

The protein channel in accordance with embodiments of the invention can either voltage- or pressure-insert into the solid-state nanopore matrix to form the hybrid nanopore sensor device. The signal for sensing using this device can be either electrical or optical, the latter offering high-density parallelized readout from multiple adjacent pores. Embodiments include mechanisms to obtain the hybrid structure, to stabilize it, and to modify it so that different types of biomolecules can be sensed.

In embodiments, the hybrid sensor does not require any lipid support, which is typically fragile and not durable; it allows atomic-precision engineering to chemically define the pore sensor properties; and chemical methods of stabilizing the portal-to-solid-state interface are controlled by biomolecular engineering and materials science approaches. The hybrid sensor can, for example, provide the advantages of: rapid and stable insertion of a protein into a solid-state nanopore; mutations of the protein can be used for sensing improvement; and translocation of biopolymers (such as nucleic acids and polypeptides) through the hybrid sensor can be performed for sensing applications. Example potential merits of such a device are in applications that include: 1) high-resolution mapping of DNA, RNA sequencing, DNA sequencing; 2) protein identification, protein conformational change monitoring; 3) polypeptide sequencing; 4) small-molecule detection, biomolecular complex detection, and enzyme-ligand binding. The broad range of uses could potentially impact many areas of the human health, biotechnology and agri-food sectors.

The advent of single-molecule detection is having an unparalleled impact on the speed with which structural and dynamic aspects of molecules can be probed (1). In this regard, nanopores have shown much promise as electrical (2-7) and electro-optical sensors (8-10) and several nanopore-based systems are now being adopted as primary tools for DNA (11-13) and RNA (14) sequencing.

Despite recent progress, identification and quantification of molecular species in solution (15-28) requires a reproducible nanopore platform that affords physical stability, structural precision, and often, a spatially-defined pore position (for example, in electro-optical sensing). While synthetic nanopores fabricated in solid-state (SS) membranes offer physical robustness (29-31), pore-to-pore variability often limits the reproducibility of experiments, necessitating additional control checks and validation. On the contrary, protein channels embedded in organic thin membranes (e.g., a lipid-bilayer) offer the highest reproducibility due to the precise folding and repetitive nature of the constituting multi-subunit protein oligomers (32,33), but their supporting membrane is typically less chemically and physically robust, and further, the pore position is not well-defined due to in-plane diffusion of the protein channel (34). Hybrid nanopore devices, in which channel-containing proteins are embedded in larger pores made in a SS matrix, have been proposed as a strategic solution for combining the benefits—while overcoming the limitations—of existing nanopores (35). Although initial experiments based on inserting pore-containing proteins with lipophilic regions into a SS pore looked promising (35), challenges in inserting such proteins into a SS pore and in controlling the protein orientation have remained major obstacles in the applicability of hybrid nanopores to nanotechnology.

An embodiment according to the present invention provides a hybrid nanopore based on the hydrophilic portal protein derived from a thermostable virus, the *Thermus thermophilus* bacteriophage G20c (36). In double-stranded DNA viruses, the portal protein is incorporated into the capsid shell (see, e.g., FIG. 1), thereby serving as a natural pore through which DNA is moved in and out (37). FIG. 1 is a schematic diagram of the DNA packaging machine of a dsDNA virus. Viral genomic DNA 100 is translocated into the preformed virus capsid by the packaging ATPase 102 through the portal protein 104 embedded in the viral capsid 106. The protein contains a tight tunnel constriction with a repetitive chemical character, being made up by a circle of identical "tunnel loops", contributed by 12 subunits (38).

Figure 2:
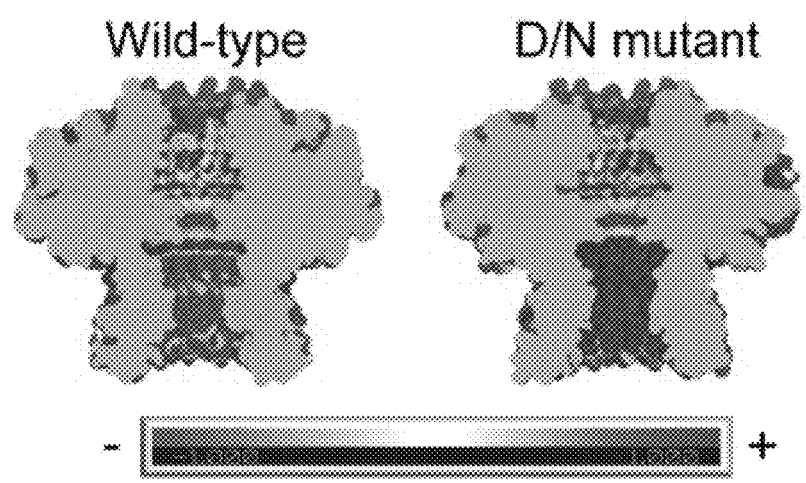
FIG. 2 is a schematic diagram showing electrostatic properties of the tunnel in wild-type (left) and mutant (right) portal proteins, where the mutant portal protein is the CD/N mutant of the G20c bacteriophage in accordance with an embodiment of the invention.

In an embodiment according to the invention, this protein is engineered to reprogram its physico-chemical and electrostatic properties. For example, in one protein version, CGG, (33) a portal with a larger minimum aperture of ~2.3 nm is defined by two residues in the tunnel loops substituted to glycines; and in another protein version, CD/N, the internal surface charges are electrostatically engineered by replacing aspartic acid (D) residues with asparagines (N). The latter CD/N mutation had a major impact on the charge of the internal tunnel's surface, (see FIG. 2) and permitted electrical sensing of biomolecules. FIG. 2 is a schematic diagram showing electrostatic properties of the tunnel in wild-type (left) and mutant (right) portal proteins, where the mutant portal protein is the CD/N mutant of the G20c bacteriophage in accordance with an embodiment of the invention. FIG. 2 shows a slice through the middle of molecular surface colored according to charge from red (−1 kT/e) to blue (+1 kT/e). In another example of this portal system, a cysteine substitution is made in an externally facing residue 49 (designated "C") which allows chemical labeling and surface immobilization of the portal protein. (33)

Figure 3:
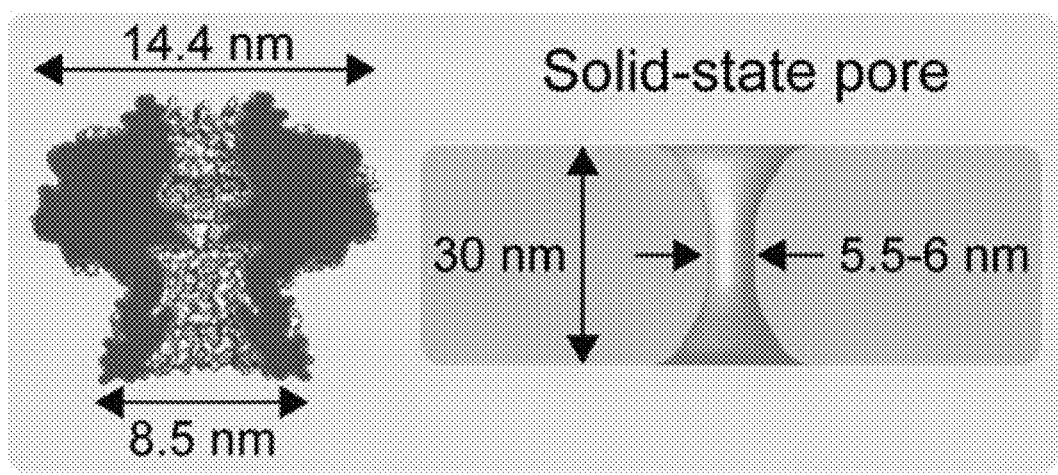
FIG. 3 is a schematic diagram showing dimensions of the portal protein (left) and the SS nanopore (right), in accordance with an embodiment of the invention.
Figure 4:
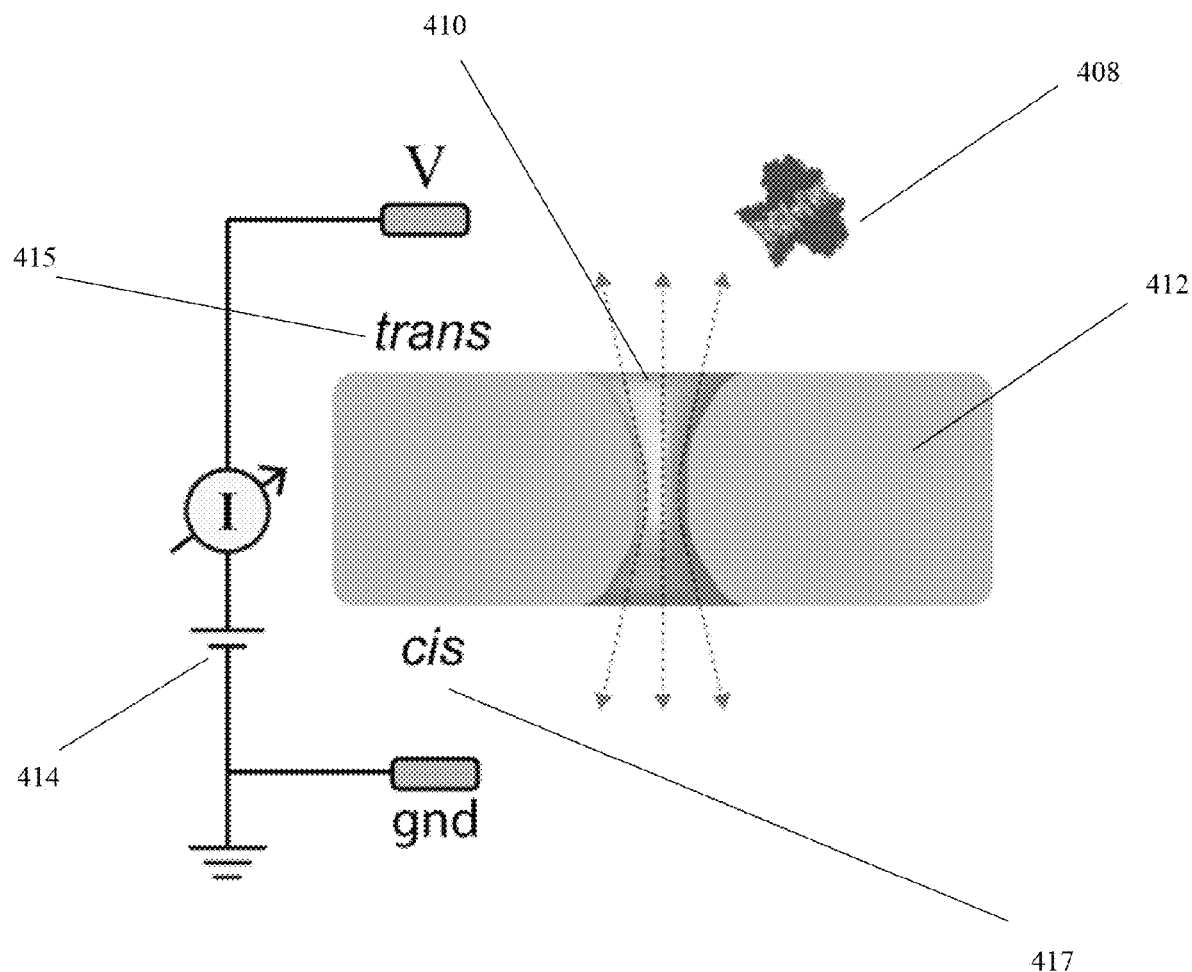
FIG. 4 is a schematic diagram illustrating insertion of a purified portal protein into a nanopore in a thin solid-state membrane, in accordance with an embodiment of the invention.
Figure 5:
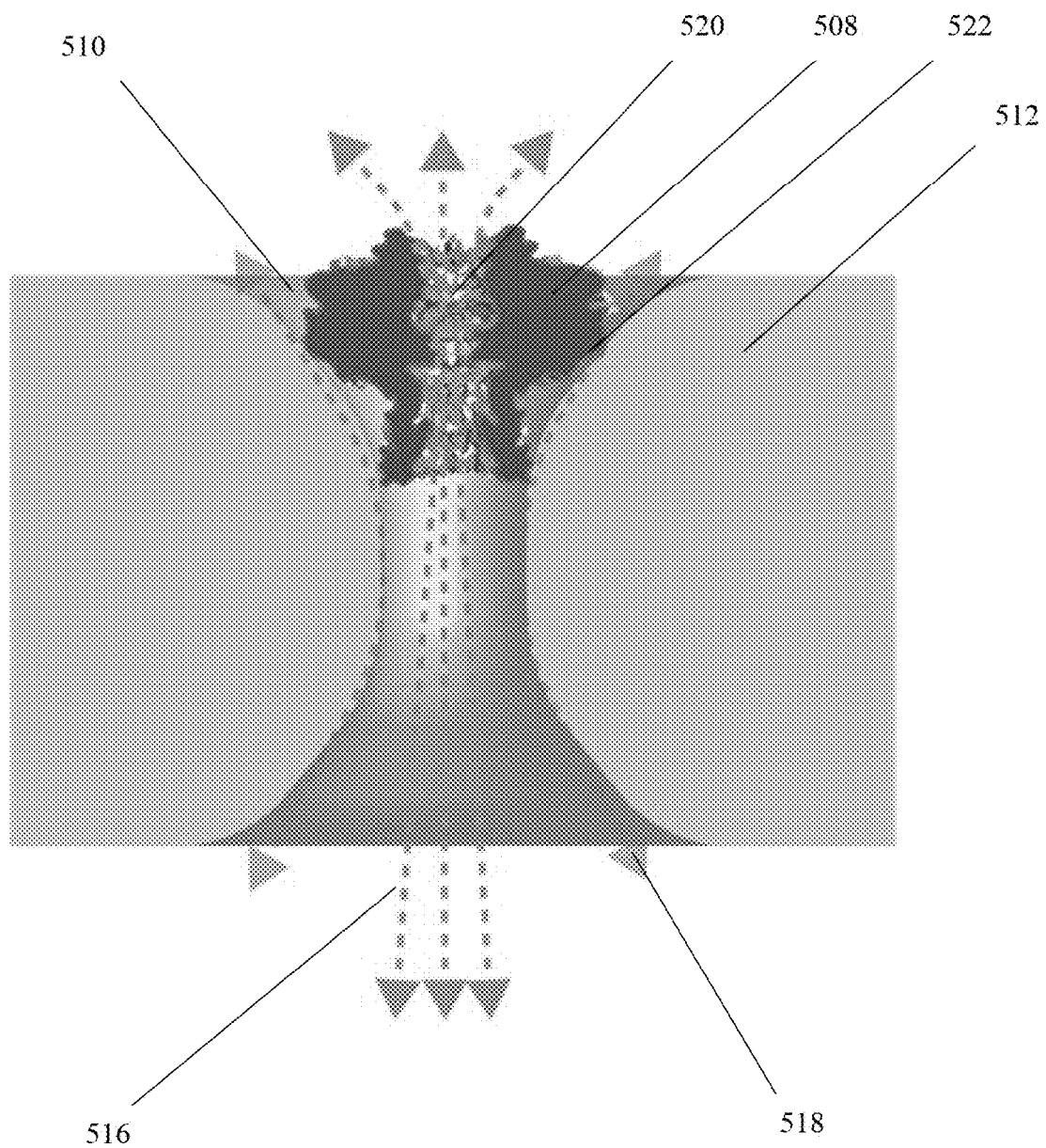
FIG. 5 is a schematic diagram of the hybrid nanopore, in accordance with an embodiment of the invention, in which application of voltage results in ion current through the pore, as well as leakage current that is peripheral to the pore.

An embodiment uses this structurally programmable portal protein as a nanoscale adapter by electrokinetically embedding it snugly inside a larger pore made in a freestanding silicon nitride (SiN), or other solid-state, membrane (see FIGS. 4 and 5). Electrokinetic "corking" occurs when the force on the protein, induced by applied voltage, is sufficient to "squeeze" the portal into the SS pore. It is found that, for stable insertion, a diameter of the solid-state nanopore of from 5.4 to 6 nm and a nominal membrane thickness of 30 nm, work well. Given the dimensions of the portal assembly (33) (see FIG. 3), the geometric constraints set by the SS pore restrict the range of possible orientations of the portal pore in it, such that the stem is inserted within the SS nanopore constriction, and the wider "cap" self-orients towards the top of the trans chamber (see FIG. 5). FIG. 3 is a schematic diagram showing dimensions of the portal protein (left) and the SS nanopore (right), in accordance with an embodiment of the invention. The portal protein is, for example, about 14.5 nm wide at its top, "cap" end, and about 8.5 nm wide at its narrower base end. The solid-state nanopore is, for example, between about 5.5 and about 6 nm wide, and about 30 nm in thickness (across the membrane). The larger size of the "cap", as compared with the SS pore diameter, prevents the entire protein from moving through the SS nanopore. Remarkably, interactions between the portal protein squeezed into the SS pore and the SS-pore surface contribute to a stable, self-inserting and self-aligning hybrid (see FIG. 5) that exhibits tolerable peripheral ion leakage, probed using cyclodextrin as a pore current modulator. FIG. 4 is a schematic diagram illustrating insertion of the purified portal protein, which assembles its dodecameric units to form a hydrophilic protein channel 408, into a nanopore solid-state pore opening 410 drilled into a thin solid-state (SS) matrix membrane 412, in accordance with an embodiment of the invention. Portal protein is applied to the trans chamber 415 of a SS nanopore device containing an electrolyte solution of 20 mM Tris pH 7.5, 0.5 M NaCl. The protein electrokinetically inserts into the SS pore during application of a positive voltage by voltage source 414. FIG. 5 is a schematic diagram of the hybrid nanopore, in accordance with an embodiment of the invention, in which application of voltage results in ion current 516 through the pore, as well as leakage current 518 that is peripheral to the pore. The hybrid nanopore sensor includes, with reference to both FIGS. 4 and 5, the voltage source 414, the electrolyte (not shown) in both the trans chamber 415 and cis chamber 417 (see FIG. 4) on both sides of the solid-state matrix 412. With reference to FIG. 5, the hybrid nanopore sensor includes: the hydrophilic protein channel 508, formed from the assembled dodecameric units of hydrophilic portal protein monomers; the solid-state matrix 512 with the solid-state pore opening 510 formed therein, where the solid-state pore opening 510 is a nanopore; and the protein nanopore channel 520 through the middle of the hydrophilic protein channel 508. The hydrophilic protein channel 508 forms a stable insertion fit 522 within the solid-state pore opening 510.

Figure 13:
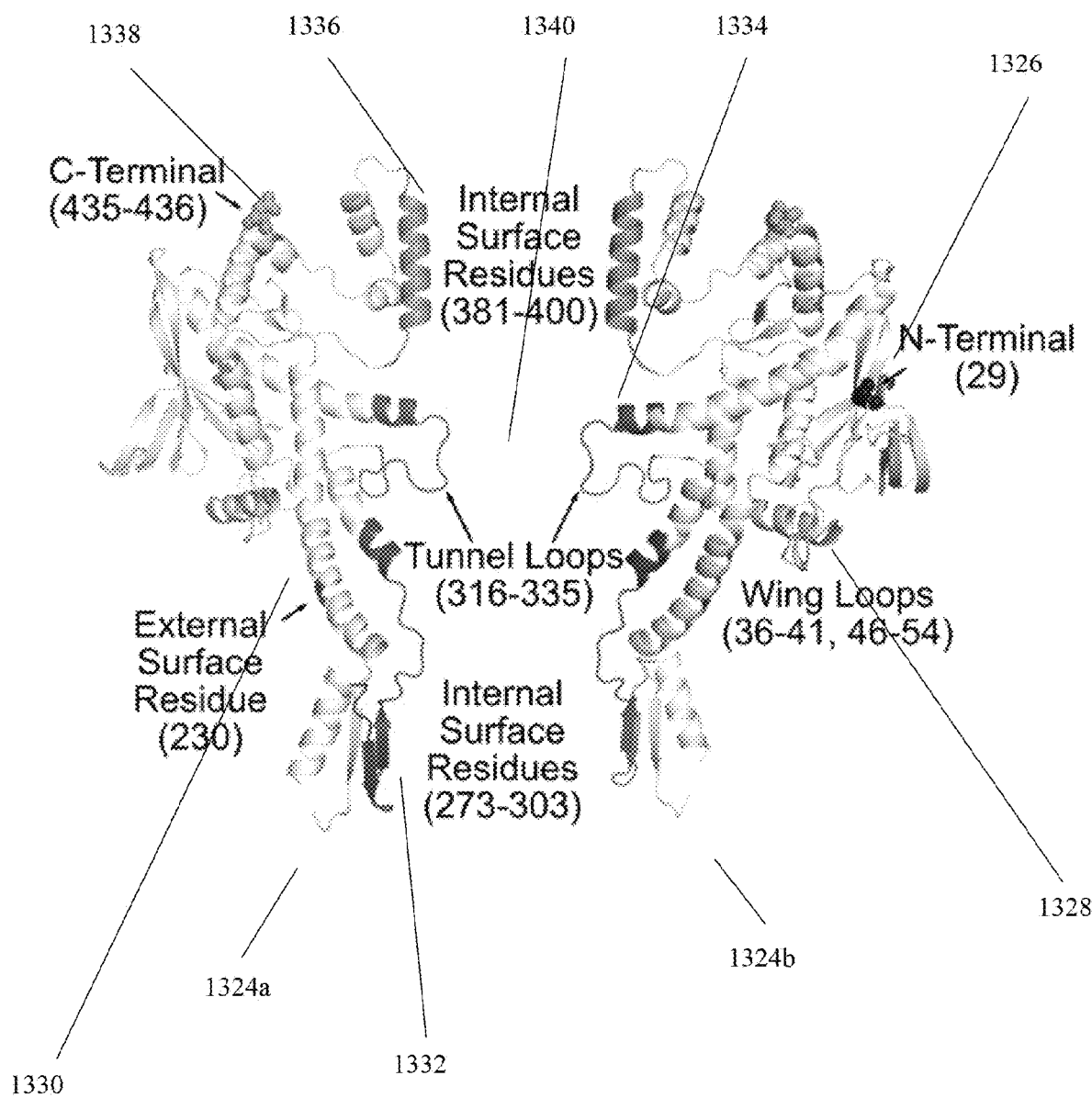
FIG. 13 is a schematic diagram showing component amino acid residue regions of the portal protein of the *Thermus thermophilus* bacteriophage G20c, which can be modified, in embodiments according to the invention, to promote assembly and operation of, and sensing with, the hybrid sensor.

FIG. 13 is a schematic diagram showing component amino acid residue regions of the portal protein of the *Thermus thermophilus* bacteriophage G20c, which can be modified, in embodiments according to the invention, to promote assembly and operation of, and sensing with, the hybrid sensor. In FIG. 13, two monomers 1324a and 1324b are shown (left and right are reflected version of each other), but it will be appreciated that twelve such monomers assemble to form the full dodecameric assembly that can create a protein channel in accordance with an embodiment of the invention. As shown in FIG. 13, the regions include: the N-terminal region 1326, which includes amino acid residue 29; the wing loop region 1328, which includes amino acid residues 36-41 and 46-54; the external surface residues 1330, which include amino acid residue 230; the internal surface residues 1332 of the lower tunnel region, which include amino acid residues 273-303; the tunnel loop region 1334, which includes amino acid residues 316-335, and forms a narrowest constriction 1340 where the tunnel loops are closest to each other; the internal surface residue 1336 of the upper tunnel region, which include amino acid residues 381-400; and the C-terminal region 1338, which includes amino acid residues 435-436.

Figure 14:
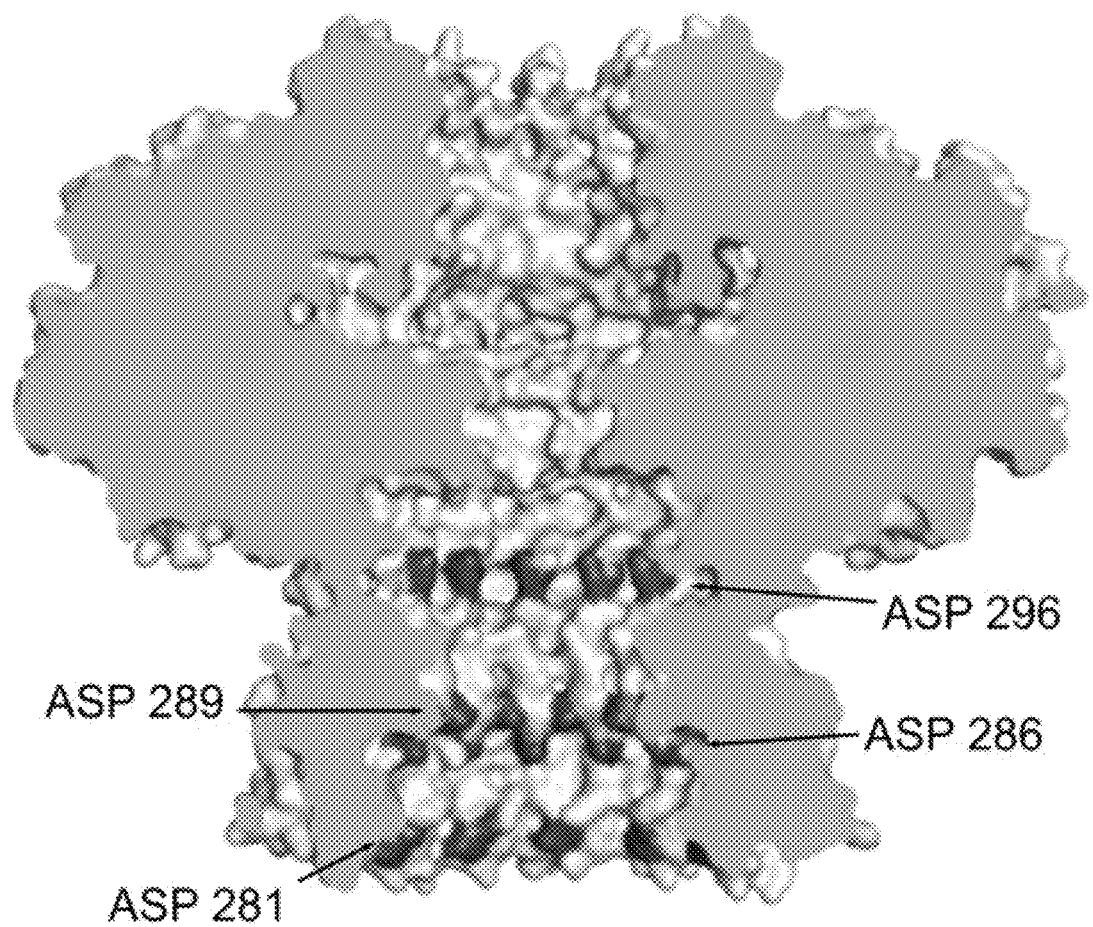
FIG. 14 is a schematic diagram showing an example of residues that can be mutated in one example, mutant, the CD/N mutant, in accordance with an embodiment of the invention.

FIG. 14 is a schematic diagram showing an example of residues that can be mutated in one example mutant, the CD/N mutant, in accordance with an embodiment of the invention. Here, residues ASP 281, ASP 286, ASP 289 and ASP 296 are mutated from aspartic acid (D) to asparagine (N).

The G20c portal protein is a stable circular dodecameric assembly of 12 monomers with a central tunnel of defined geometry and physicochemical properties. In accordance with some embodiments, a base scaffold of the protein is used that is trimmed to the core structure comprising residues 25-438 of the portal protein's amino acid sequence, where the unstructured N- and C-terminal regions (residues 1-24 and 439-448 of the wild type residues 1-448 of the protein) have been removed to improve stability. A major advantage of this scaffold is the absence of cysteine residues, which allows flexible design of cysteine-containing mutants that can be chemically derivatized for different applications, such as attachment to surfaces or insertion into membranes.

In accordance with embodiments of the invention, the properties of the portal protein can be engineered for specific sensing and device integration applications by mutating the surface residues lining the tunnel, those on the outer surface of the portal protein assembly and residues that stabilize or otherwise alter either intramonomer or intermonomer contacts. Mutations can, for example, include, but are not limited to, the segments containing internal tunnel lining residues 273-303 of the lower tunnel region and 381-400 of the upper tunnel region; tunnel loop residues 316-335; and surface residues such as the wing loops 36-41 and 46-54 that are part of a range of residues 36-54.

Further modifications to the protein can, for example, include fusion of peptide sequences, protein domains or proteins to the N or C-terminus of the protein or into external loops that will confer properties for attachment or sensing of ligand binding events to different biomolecules, bacteria, cells viruses and/or chemical assemblies.

In some embodiments, portal protein variants comprise specifically placed cysteine residues for chemical attachment to surfaces, insertion into lipid bilayers and/or linking to additional sensor components, such as ligand binding aptamers. These include the 49C or C mutant where a cysteine has been introduced into one of the wing loops at position 49; and the D400C variant where a cysteine has been placed at the top of the upper tunnel helix. Mutant proteins are referred to herein by the "Protein Version" names given in Tables 1-7, below. The 49C version has the amino acid sequence given in SEQ ID NO: 11 and the DNA sequence given in SEQ ID NO: 12. The D400C version has the amino acid sequence given in SEQ ID NO: 37 and the DNA sequence given in SEQ ID NO: 38. The 49C version can be used, either alone or in combination with other mutations, such as CGG or CD/N. D400C has been found to form dodecamer sized assemblies when purified.

In other embodiments, the tunnel properties of the portal assembly can be engineered, for example by expanding the narrowest constriction of the tunnel loops of residues 316-335 (see FIG. 13) and by altering the electrostatic surface potential of the tunnel, as in CD/N. Additional examples of other variants in the tunnel loop geometry that assemble into the characteristic circular protein complexes include: V325M designed to further restrict the narrowest aperture of the tunnel; and the Loop2GG and CLoop3G mutants that entirely remove the central constriction in the tunnel. Further charge alterations to the tunnel include the placement of a flexible positive lysine residue at the narrowest point of the tunnel loops (I328K) and proposed additional substitution of aspartic acid residues 383 and 400 in the upper tunnel helix (residues 381-400) with asparagine residues to reduce the negative charge in the upper tunnel surface.

In further embodiments, the external surface charge properties of the protein can be altered by introducing charged amino acids in place of uncharged surface residues, such as with the V40E and L230E, which are, respectively, in the wing loop region (for V40E) and the external surface residue region (for L230E). Similar alterations in the external surface residues can be made to create a more hydrophobic external surface. Peptide sequences have been successfully introduced into the wing loop 46-54 to promote binding to silicon surfaces (in the SIN1, SIN 2 and SIN 4 mutations). SIN1 and SIN2 form circular assemblies.

In other embodiments, extensions to the N- and C-terminal can be used to introduce longer peptide sequences for targeted surface (metal or lipid) interaction or to introduce ligand binding domains for specific sensing applications. Such extensions include the hexahistidine affinity tag used for nickel binding and purification. Additional N-terminal extensions include the SIN3 silicon binding sequence.

In one embodiment, the wild type full length portal protein of G20c bacteriophage, comprising SEQ ID NO: 1, can be modified in the lower internal surface residue of the hydrophilic protein channel, to alter the electrostatic surface potential of the lower internal surface of SEQ ID NO: 1. For example, for such a purpose, the hydrophilic protein channel can comprise the CD/N variant with amino acid SEQ ID NO: 27, which has a corresponding modified DNA sequence of SEQ ID NO: 28.

In another embodiment, the wild type portal protein, comprising SEQ ID NO: 1 can be modified to replace the residue of SEQ ID NO: 1 with a cysteine residue. For example, for such a purpose, the hydrophilic protein channel can comprise the 49C variant with amino acid SEQ ID NO: 11, which has a corresponding modified DNA sequence of SEQ ID NO: 12, or can comprise the D400C variant with amino acid SEQ ID NO: 37, which has a corresponding modified DNA sequence of SEQ ID NO: 38.

In another embodiment, the Wild Type portal protein of SEQ ID NO: 1 can be modified in the tunnel loop residue of the hydrophilic protein channel, the modification comprising an expansion of the narrowest constriction of the tunnel loop of SEQ ID NO: 1, a restriction of the narrowest constriction of the tunnel loop of SEQ ID NO: 1, or a removal of the narrowest constriction of the tunnel loop of SEQ ID NO: 1. For such purposes, the hydrophilic protein channel can, for example, comprise one of the G, M, CGG, Loop2GG and 49CLoop3G variants, which have, respectively, the amino acid sequences of SEQ ID NO: 15, SEQ ID NO: 17, SEQ ID NO: 21, SEQ ID NO: 23, and SEQ ID NO: 25, and the corresponding modified DNA sequences of SEQ ID NO: 16, SEQ ID NO: 18, SEQ ID NO: 22, SEQ ID NO: 24, and SEQ ID NO: 26.

In another embodiment, the Wild Type portal protein of SEQ ID NO: 1 can be modified in the tunnel loop residue of the hydrophilic protein channel, the modification comprising an alteration of an electrostatic charge property of the tunnel loop of SEQ ID NO: 1. For this purpose, the hydrophilic protein channel can, for example, comprise the K variant, which has amino acid SEQ ID NO: 19 and corresponding modified DNA sequence of SEQ ID NO: 20.

In another embodiment, the Wild Type portal protein of SEQ ID NO: 1 can be modified to alter an external charge of the hydrophilic protein channel. For example, for such a purpose, the hydrophilic protein channel can comprise one of the L230E and 40E variants, which respectively have amino acid SEQ ID NO: 9 and SEQ ID NO: 13, and corresponding modified DNA sequences SEQ ID NO: 10 and SEQ ID NO: 14.

In another embodiment, the Wild Type portal protein of SEQ ID NO: 1 can be modified to promote binding of the hydrophilic protein channel to the solid-state matrix. For example, for such a purpose, the hydrophilic protein channel can comprise one of the SIN1, SIN2 and SIN 4 variants, which respectively have amino acid SEQ ID NO: 29, SEQ ID NO: 31 and SEQ ID NO: 35, which have corresponding modified DNA sequences of SEQ ID NO: 30, SEQ ID NO: 32 and SEQ ID NO: 36.

In another embodiment, the Wild Type portal protein of SEQ ID NO: 1 can be modified to extend the N-terminal of a cleaved portion of SEQ ID NO: 1. For example, for such a purpose, the hydrophilic protein channel can comprise the SIN3 variant, which has amino acid SEQ ID NO: 33, and corresponding modified DNA sequence SEQ ID NO: 34.

In another embodiment, the Wild Type portal protein of SEQ ID NO: 1 can be modified to cleave off the amino acid residue of at least one of the C-terminal region and the N-terminal region of SEQ ID NO: 1. For example, for such a purpose, the modification can comprise a modification of one of the WT 1-438 C-term, WT 1-438 3C prot and WT Nanopore variants, for which the amino acid sequences are respectively given by SEQ ID NO: 3, SEQ ID NO: 5 and SEQ ID NO: 7, and for which the corresponding modified DNA sequences are SEQ ID NO: 4, SEQ ID NO: 6 and SEQ ID NO: 8.

In another embodiment, the Wild Type portal protein of SEQ ID NO: 1 can be modified in one or more of: a wing loop residue (such as residues in the range 36-41 or 46-54), a tunnel loop residue (such as residues in the range 316-335), an upper internal surface residue (such as residues in the range 381-400), a lower internal surface residue (such as residues in the range 273-303), an external surface residue (for example, residue 230), a C-terminal end residue (for example, residues 435-436), and an N-terminal end residue (for example, residue 29).

In addition, attachment of the portal protein to the solid-state surface can, for example, be assisted using vapor deposition of maleimide/thiol-silane compounds; by silicon binding peptides, such as binders to either, or both, SiN or SiOx; or by thiocholesterol or other maleimide-lipid conjugated to L49C by thiol chemistry. The solid-state matrix may comprise a coating to promote binding of the solid-state matrix to the hydrophilic protein channel. For example, the coating may comprise a thiol-coupling compound; and may, for example, comprise a maleimide compound or other thiol-coupling compound.

Although some embodiments herein are discussed based on use of a modified portal protein of the *Thermus thermophilus* bacteriophage G20c, it should be appreciated that portal proteins from other bacteriophages (including bacteriophages of *Thermus thermophilus*, and other bacteriophages) can be used, including any hydrophilic portal protein that achieves performance of a similar function to the hydrophilic protein channel in a stable insertion fit within a solid-state pore opening, that is taught herein. In one example, the portal protein of the *Thermus thermophilus* bacteriophage P23-45, or modifications of that portal protein, can be used. In that regard, SEQ ID NO: 40, or a modified protein based on SEQ ID NO: 40, can be used; and a protein encoded by its DNA sequence, which is SEQ ID NO: 41, or a modified protein encoded by a modified DNA of SEQ ID NO: 41, can be used. In particular, one or more of three amino acid variations of SEQ ID NO:1 can be made, which results in SEQ ID NO: 40, or a modification thereof: at residue 328 of SEQ ID NO: 1, there is an I amino acid residue, which, if changed to V, becomes the amino acid residue 328 of SEQ ID NO: 40; at residue 189 of SEQ ID NO: 1, there is an S amino acid residue, which, if changed to an N amino acid residue, becomes the amino acid residue 189 of SEQ ID NO: 40; and at amino acid residue 367 of SEQ ID NO: 1, there is an S residue, which, if changed to a G amino acid residue, becomes amino acid residue 367 of SEQ ID NO: 40. Thus, a mutation at one or more of amino acid residue locations 328, 189 and/or 367 of SEQ ID NO: 1 can be used.

In addition, it should be noted that monomer protein units of proteins taught herein can be assembled to form the full portal protein that functions to form the stable insertion fit within a solid-state pore opening that is taught herein. For example, the portal protein of the *Thermus thermophilus* bacteriophage G20c forms a dodecameric structure, made of 12 monomer protein units, which together assemble to form the full "plug" protein (see FIG. 4) that forms a stable insertion fit within the solid-state pore opening. Thus, a "hydrophilic protein channel," as used herein, can include more than one monomer of a protein, such as 12 monomer protein units assembled together to form the hydrophilic protein channel through the dodecameric combined protein structure assembled from the monomers of the protein.

EXAMPLES

There will now be described a set of example experiments, conducted in accordance with an embodiment of the invention.

Example 1

Figure 6:
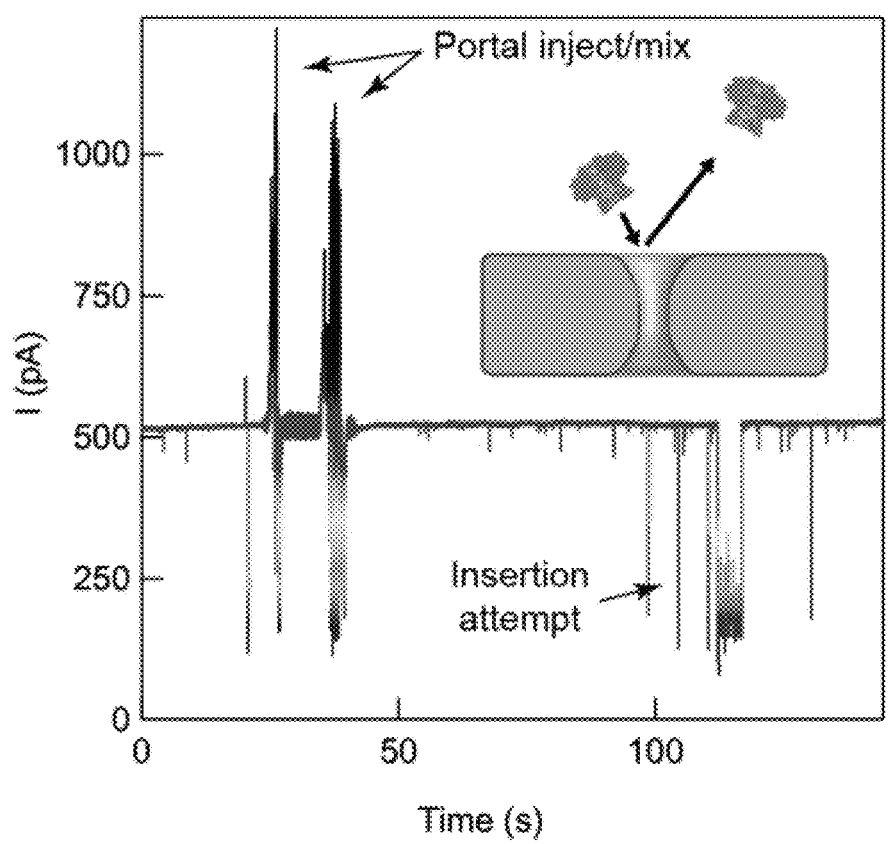
FIGS. 6-10 are graphs showing characterization of hybrid pore formation, in experiments in accordance with an embodiment of the invention.
Figure 7:
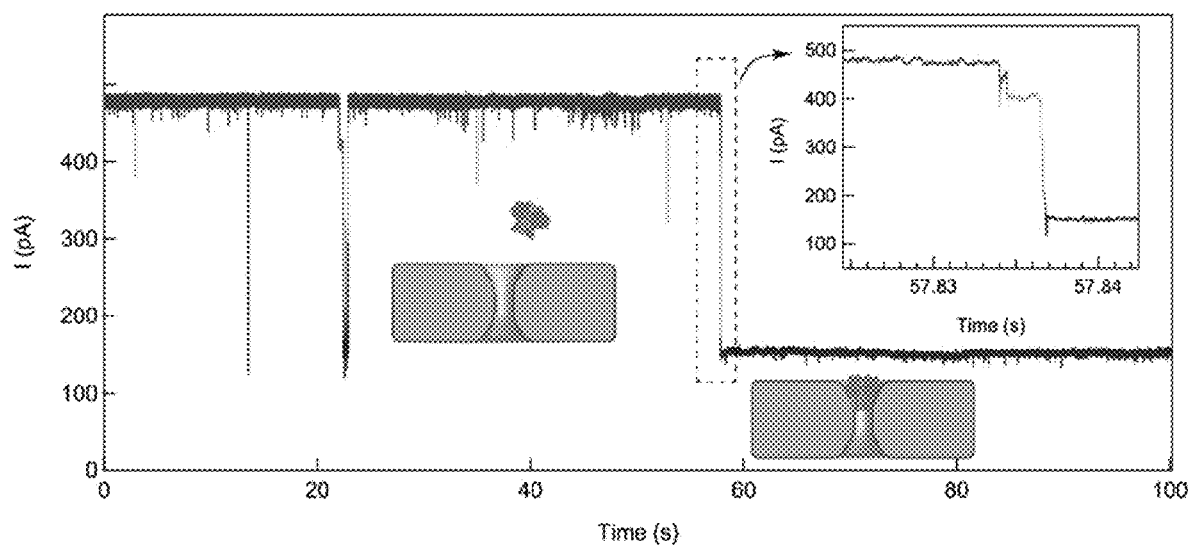
Figure 8:
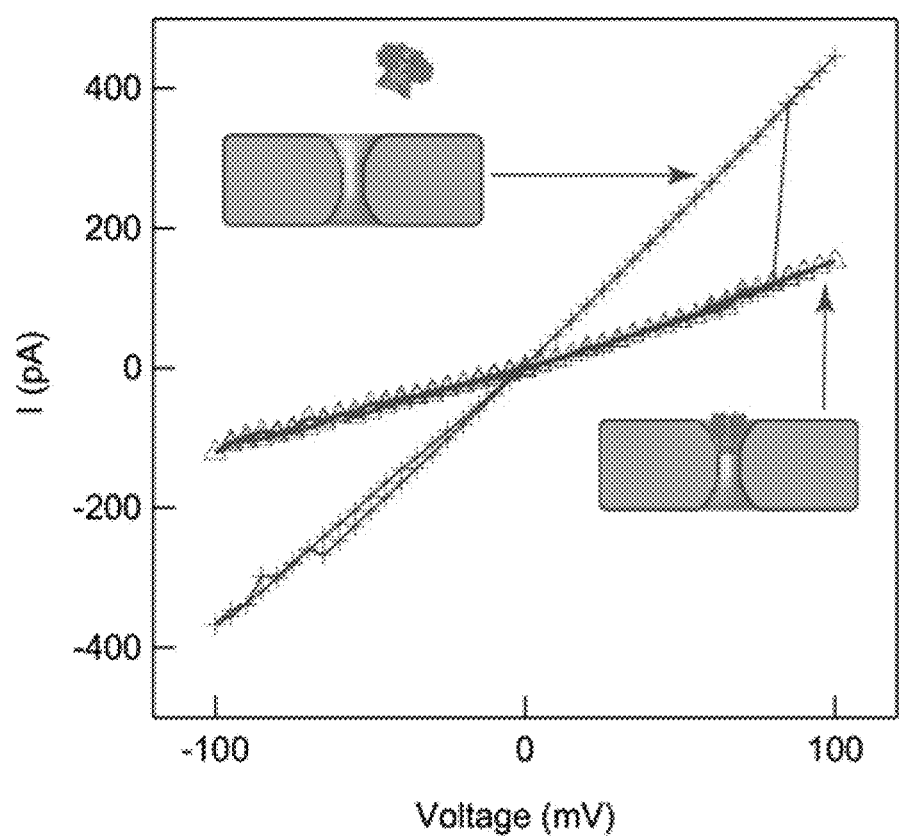
Figure 9:
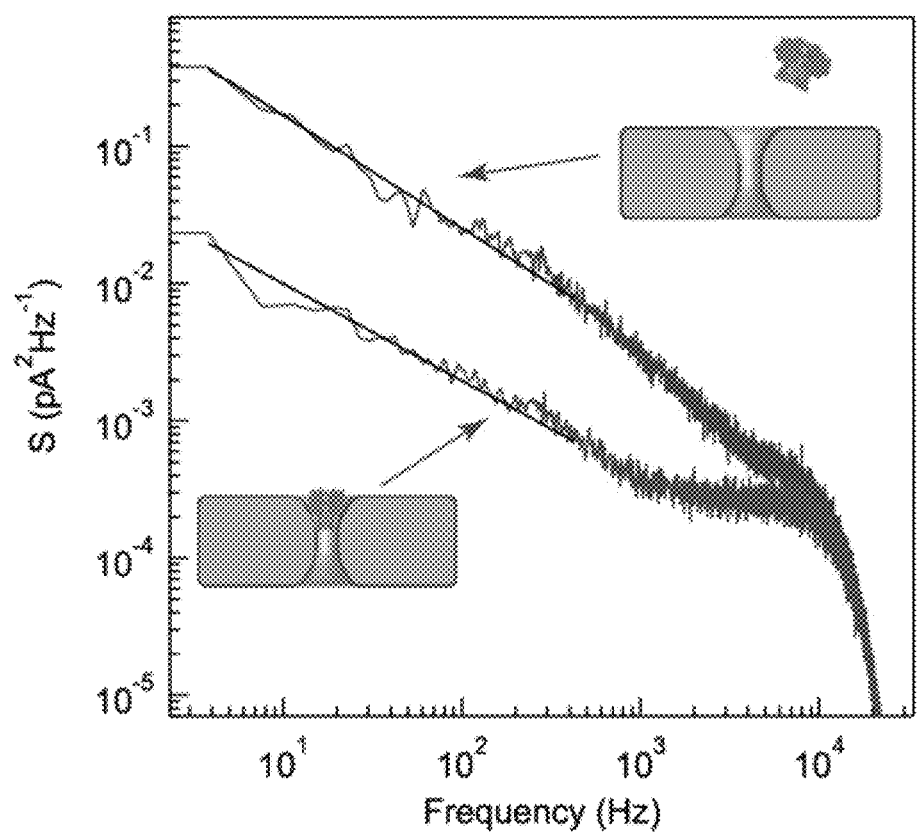
Figure 10:
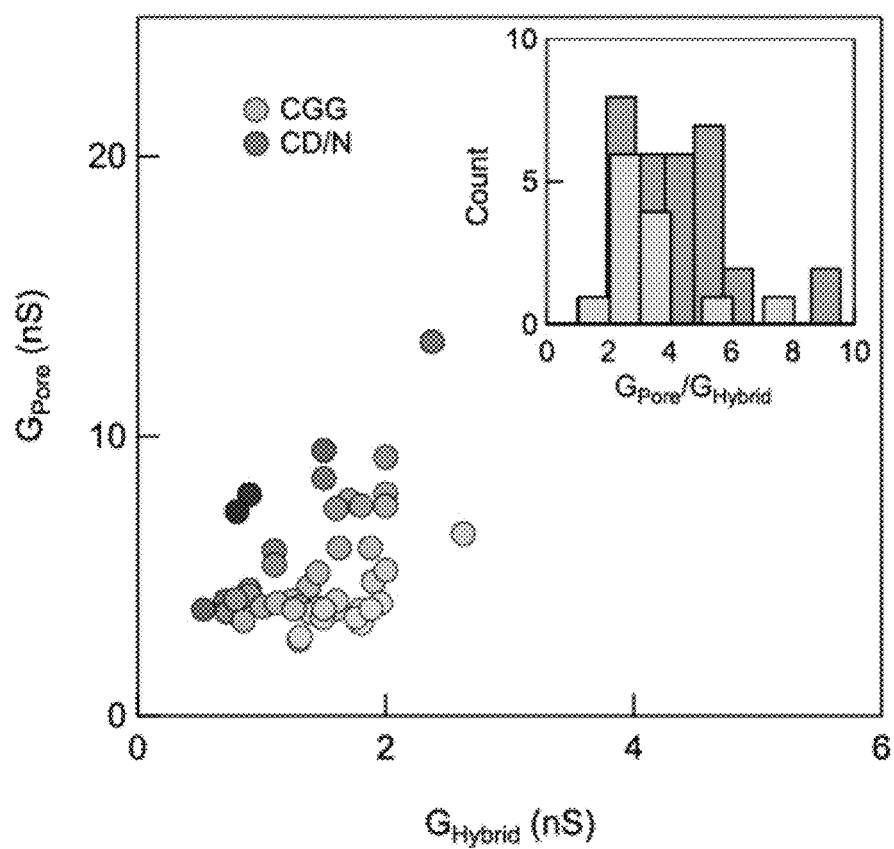

FIGS. 6-10 are graphs showing characterization of hybrid pore formation, in experiments in accordance with an embodiment of the invention. FIG. 6 is a graph of a typical current profile over time recorded through a 5.5 nm SS pore at +100 mV. After injection of 0.1 nmol of portal protein, short current drops are detected, interpreted as portal collisions with the solid-state nanopore. FIG. 7 is a graph of a representative current vs time trace recorded for a 5.4 nm SS nanopore at +80 mV, showing stable insertion of a portal protein. FIG. 8 is a graph of current as a function of the applied voltage for a 5.5 nm SS pore recorded before (red markers, with a higher slope) and after insertion of a portal protein (purple, with a lower slope). FIG. 9 is a graph of current noise analysis of a 5.5 nm diameter solid-state nanopore before (red, top curve) and after insertion of a portal protein (purple, bottom curve). FIG. 10 is a graph of conductance of solid-state nanopore vs conductance of portal hybrid pore (n=32 for CD/N hybrids and n=15 for CGG hybrids). Experiments were performed in 0.5 M NaCl, 20 mM Tris pH 7.5.

In experiments in accordance with an embodiment of the invention, the hybrid nanopores exhibit lifetimes of hours, and similar ion current noise values to a lipid bilayer-supported portal protein nanopore (33) (see FIGS. 6-10). The electrical properties of the hybrid pore were characterized and applied to electrically detect different biomolecules. Using the hybrid portal with engineered internal pore properties (CD/N, see FIG. 2, right), it was demonstrated that a folded protein larger than the pore interior does not enter the hybrid portal, whereas homopolymeric single-stranded DNA (ssDNA), double-stranded DNA (dsDNA) that contains a single-stranded tail, and a peptide predicted to have a random coil conformation with a 10-amino acid α-helix at the C-terminus, can all be discriminated based on their distinct signal amplitudes, in a way that is commensurate with their molecular cross-section. The results indicate that the hybrid portal is a versatile sensor of various biopolymer types, which may, with further development, find uses in genomic mapping as well as polypeptide and oligonucleotide sequencing.

After confirming the base current of stable SS nanopores of the desired diameter, addition of the portal protein to the trans chamber results in reversible partial blockades of the ionic current (FIGS. 6 and 7). These short-lived events are interpreted as portal protein collisions with the SS nanopore without stable insertion, where the ion current is partially blocked as the protein approaches the SS pore, prior to movement away. These short-lived events were usually followed by long-lived events (FIG. 7), of comparable current blockade levels, events that were only observed in SS pores with diameters of 5.4 to 6 nm. The long-lived events are interpreted as stable insertion of a portal protein into the SS nanopore to form a hybrid nanopore. The average conductance of these hybrid pores was calculated (FIG. 10) to be 1.50±0.48 nS and 1.33±0.42 nS for the CD/N (from 32 hybrid nanopores) and the CGG (from 15 hybrid nanopores) variants, respectively. Such hybrid pores remain stable at both positive and negative voltages up to +120 mV and −80 mV (FIG. 8), however, application of an electric field with strengths greater than −80 mV generally resulted in release of the protein from the SS nanopore. These data are consistent with the protein insertion being electrokinetically driven.

Obtaining a sufficient increase in the signal-to-noise ratio is a major challenge for properly identifying transport events by nanopore sensing. Power spectral densities of the current noise for a SS nanopore before, and after, insertion of a portal protein (FIG. 9) showed that the 1/f noise at low frequencies decreased upon formation of the hybrid pore. This 1/f noise reduction is consistent with a reduced pore conductance, as well as an indicator of the reduced surface charge fluctuations that are hallmarks of silicon nitride surfaces (39). This, along with the observation that capacitance-dominated noise at high frequencies was comparable for both pores, suggests that no new source was introduced during hybrid pore formation. It was deduced that the observed variation in the open pore current for different hybrid nanopores was likely to be caused by differences in SS geometry and the associated leakage currents around the portal protein. It was attempted to measure the extent of ion leakage from the pore by measuring β-cyclodextrin interactions with the hybrid pore for the CGG mutant, a mutant that was previously embedded into a lipid membrane (33). The results show that β-cyclodextrin does not translocate the pore, in contrast for the same experiment conducted on the lipid-embedded version of the same portal protein. While this precludes an accurate measurement of the leakage, these results suggest that "corking" the protein into a snug SS nanopore slightly reduces the innermost pore constriction. The reproducible signals obtained from biomolecules, as well as the steady baselines of the hybrid, allow current blockades as low as ~20 pA to be accurately measured. These data demonstrate that despite a low level of constant peripheral leakage, these hybrid pores are unique lipid-free protein-based pore sensors.

Example 2

The sensing capabilities of these hybrid nanopores were then investigated by analyzing the transport of a peptide, comprising residues 1-43 of the human TPX2 protein, as a function of applied voltage (FIGS. 11A-11C).

FIGS. 11A-11C are graphs showing dynamics of TPX2 peptide transport, in experiments in accordance with an embodiment of the invention. FIG. 11A is a graph showing a current vs time trace recorded through a hybrid pore at +30, +40 and +55 mV in the presence of 10.3 μM TPX2 peptide. FIG. 11B is a semi-log plot of the event frequency as a function of the applied voltage. The line is an exponential fit to the equation. FIG. 11C is a semi-log plot of the peptide dwell time as a function of the applied voltage. The lines in FIGS. 11B and 11C are exponential fits. Experiments were performed in 0.5 M NaCl, 20 mM Tris pH 7.5.

The TPX2 peptide is negatively charged at pH 7.5 (pI=3.7) and was added to the cis chamber, on the opposite side of the membrane to which the portal protein was introduced (see inset to FIG. 11B). Adjusting the applied voltage from +30 to +60 mV resulted in an increased baseline ion current through the hybrid pore, as well as the frequency of observed current blockades (FIG. 11A). Two kinds of current blockades associated with two different events were detected: bumping events, characterized by brief, low-level current blockades, arising from diffusion of the peptide close to the hybrid pore entrance; and translocation events, characterized by larger current blockades of longer duration. These two types of events are typically seen during translocation of DNA (40-42) and proteins (43-45) through protein channels. The inter-event time distribution is well fit by a single exponential equation. The entry frequency (FIG. 11B) of the peptide into the hybrid pore is described by a Van't Hoff Arrhenius relationship (44,46), $f=f_0 \exp(V/V_0)$, consistent with both translocation of DNA (40-42), proteins (43,47) and peptides (46, 48-51) through either α-hemolysin or aerolysin; and a significant entropic barrier for peptide entry into the pore. The dwell time distributions were well fit by a double-exponential equation, which are typically due to two types of processes, normally associated with short bumping and longer translocation events (16). It was found that the average frequency for both types of events increases exponentially (FIG. 11B), while the average dwell time for the long events decreased exponentially with the applied voltage (FIG. 11C). Based on prior work that employed the α-hemolysin and aerolysin nanopores, (43, 45) it was concluded that the long events represent transport of the peptide through the hybrid pore to the trans chamber.

Example 3

In order to further demonstrate the sensing capabilities of this hybrid pore, the transport of other biopolymers was further investigated: dsDNA that contains a ssDNA tail, ssDNA, a folded protein as well as the TPX2 peptide (FIGS. 12A-12E).

Figures 12A, 12E:
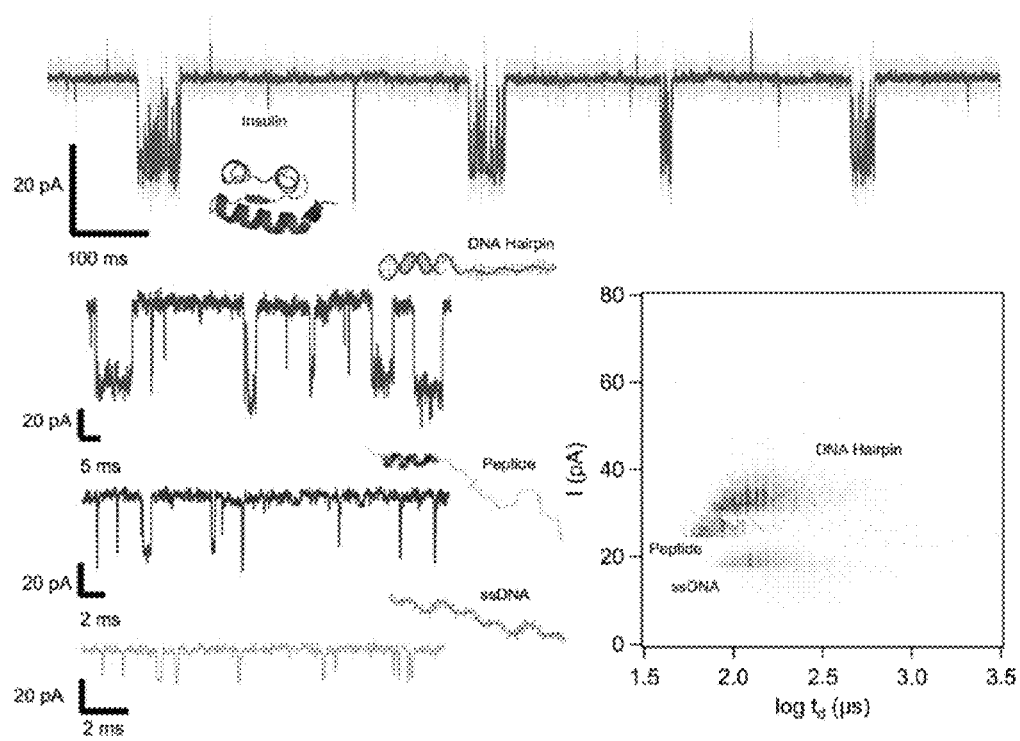

FIGS. 12A-12E are graphs illustrating sensing of different biopolymers using a hybrid nanopore, in experiments in accordance with an embodiment of the invention. Current vs time trace recorded through the hybrid pore at +60 mV in the presence of (FIG. 12A) 36.0 μM insulin, (FIG. 12B) 7.7 μM DNA hairpin, (FIG. 12C) 10.3 μM TPX2 peptide and (FIG. 12D) 16.6 μM ssDNA. The data in (FIG. 12A) were filtered at 10 kHz (grey) or 0.5 kHz (green). FIG. 12E is a scatter plot of ΔI vs dwell time for the DNA hairpin (red), the peptide (purple) and the ssDNA (orange). Experiments were performed in 0.5 M NaCl, 20 mM Tris pH 7.5.

Since all of these polymers are negatively charged at pH 7.5, following their addition to the cis chamber (the opposite side of the SS membrane to portal insertion), electrophoresis allows molecular capture into the base of the portal protein. After addition of each biopolymer: 36.0 μM Insulin (FIG. 12A); 7.7 μM hairpin-polydT$_{50}$ (FIG. 12B); 10.3 μM TPX2 peptide (FIGS. 11A-11C and 12C); 6.9 μM 60 bp-polydT$_{30}$; and 16.6 μM ssDNA polydA$_{20}$dC$_{20}$dA$_{20}$ (FIG. 12D); reversible partial blockades of the ionic current are observed at +60 mV. Similar short-lived bumping events as well as longer events were observed for each biopolymer, as described above for the TPX2 peptide (FIGS. 11A-11C). These types of blockades were also observed at several different voltages for DNA molecules, with voltage dependent changes in event frequency and duration for ssDNA polydA$_{20}$dC$_{20}$dA$_{20}$ consistent with translocation occurring, as noted for the peptide above (FIGS. 11A-11C). Conversely, the folded, globular molecule of insulin, with a smallest dimension of ~3 nm (PDB code: 1zeh) (52, 53) is too large for the ~2 nm constriction of the hybrid pore and therefore does not translocate. It is however possible that insulin explores the cavity at the portal tunnel's entrance (~5 nm) without being transported to the trans chamber, producing structured events that are long-lived and have a low current blockade level. Such events have been previously observed for nanoreactors, where biomolecules are "captured" or "tethered" within ClyA and FracC nanopores (20, 54).

Lastly, the event characteristics for different biopolymers were compared at the same applied voltage of +60 mV by overlaying their scatter plots of ΔI vs. dwell times, as shown in FIG. 12E. The level of current blockade, ΔI, appeared to be biopolymer dependent. Current blockades were found for the dsDNA (FIG. 12E) of ΔI=34.6±4.2 pA, while in contrast, ΔI=18.1±3.2 pA was found for ssDNA. This is nearly two times less than for the partially dsDNA, and is consistent with values found for dsDNA and ssDNA in SS nanopores (55), where the difference in conductance was found to be ~2.75 fold. For the peptide, ΔI=30.1±5.5 pA was found. Since it was shown that the peptide is transported through the pore (FIGS. 11A-11C) and the peptide is predicted to contain an α-helix of ~1.4 nm in diameter as seen in the structure of the TPX2 peptide bound to its partner kinase, Aurora A (PDB: 1OL5), the data are compatible with translocation through the narrowest constriction of the hybrid pore (~2 nm diameter). The ΔI value found for the peptide is consistent with the α-helical region being the main cause of the blockade, and with its diameter being intermediate between that of dsDNA and ssDNA. These data suggest that the predicted α-helix is present in the isolated peptide under these experimental conditions. While transport of structured biopolymers has been reported for nucleic acids (56, 57), it is believed that only a single report presents transport of an α-helical peptide through a protein nanopore (45).

Hybrid nanopores, supported by SS membranes could offer superior properties to both the planar lipid bilayer based pores (that are sensitive to temperature, osmotic pressure, and applied electric field strength and not geometrically controllable) and SS nanopores (that are prone to edge erosion and difficult to reproducibly fabricate with diameters <5 nm). However, despite having been the subject of industrial and academic research, development of a device that can be easily fabricated, has proven difficult. For example, producing a hybrid pore based on the α-hemolysin, a membrane protein, noted relatively short hybrid pore lifetime and required complex protein modifications (35). In contrast, the hybrid nanopore described here is based on a soluble, stable and relatively hydrophilic viral portal protein, whose chemical properties, including those inside tunnel, can be easily tuned.

An embodiment demonstrates biomolecule sensing capabilities of a novel lipid-free hybrid nanopore comprising the G20c portal protein inserted into a thin SS SiN membrane. This hybrid pore is easy to assemble, with the portal protein readily electrokinetically inserting into the SS-pores and typically remaining stable for hours of experimental time. The electrical sensing data clearly show characteristic readout for ds and ssDNA, as well as a peptide and a globular protein. The hybrid pore demonstrates utility as a nanosensor.

Materials and Methods
1. Preparation of CGG and CD/N

To produce the mutant portal protein, CGG, the following procedure was followed. An analogous procedure was used to produce a different mutant portal protein, CD/N. The following method of cloning, expression and purification of G20C portal proteins was used (here described for CGG and 49C mutants). The DNA encoding for G20c portal protein (residues 25-438) was amplified by PCR using Phusion high fidelity DNA polymerase (New England Biolabs, Ipswich, Massachusetts, U.S.A.), and cloned into the YSBL-Lic+ (Bonsor, D.; Butz, S. F.; Solomons, J.; Grant, S.; Fairlamb, I. J. S.; Fogg, M. J.; Grogan, G. Ligation Independent Cloning (LIC) as a Rapid Route to Families of Recombinant Biocatalysts From Sequenced Prokaryotic Genomes. *Org. Biomol. Chem.* 2006, 4, 1252-1260) expression plasmid encoding an N-terminal 3C protease cleavable hexahistidine tag using the HiFi DNA assembly master mix (New England Biolabs, Ipswich, Massachusetts, U.S.A.). All mutant variations of the wild-type (WT) protein were produced using a variation of the linear exponential PCR and ligase-dependent production of closed circular plasmid DNA using Phusion DNA polymerase (New England Biolabs, Ipswich, Massachusetts, U.S.A.). Briefly, primer sets were designed to introduce the mutation(s) and amplify the entire plasmid by PCR, after which the DNA product was purified using a PCR cleanup kit (Thermofisher). Phosphorylation and ligation of the amplified DNA ends and Dpn I digest of the template plasmid was achieved in a 3 h reaction at 37° C., containing 1× Cutsmart buffer (New England Biolabs, Ipswich, Massachusetts, U.S.A.), 1 mM ATP, 10 mM DTT, and 1 unit each of Dpn I, T4 polynucleotide kinase, T4 ligase (New England Biolabs, Ipswich, Massachusetts, U.S.A.). Ligated closed circular plasmid DNA was transformed into competent DH5α cells. Mutants were screened by colony PCR and confirmed by DNA sequencing in both directions.

Wild type and mutant proteins G20c WT (WT) and G20c V325G_I328G (GG)) were expressed and purified from *E. coli* BL21 (DE3) pLys S cells. Proteins containing cysteine mutants, G20c-L49C (49C) and G20c-L49C_V325G_I328G (CGG) were expressed and purified from the SHuffle (New England Biolabs, Ipswich, Massachusetts, U.S.A.) expression strain. Protein expression and purification was conducted as described (Williams, L. S.; Levdikov, V. M.; Minakhin, L.; Severinov, K.; Antson, A. A. 12-Fold Symmetry of the Putative Portal Protein From the *Thermus Thermophilus* Bacteriophage G20C Determined by XRay Analysis. *Acta Crystallogr., Sect. F: Struct. Biol. Cryst. Commun.* 2013, 69, 1239-1241.) in LB (Melford) containing 35 µg/mL kanamycin and 50 µg/mL chloramphenicol. Briefly, 10 mL of an overnight culture was inoculated into 1 L of LB (containing antibiotics) and incubated at 37° C. until the $OD_{600}$ reached 0.8, followed by induction overnight at 16° C. with 0.5 mM IPTG when the cells were harvested by centrifugation at 4000 rpm for 30 min and the pellets snap frozen in liquid nitrogen and stored at −80° C. until use. Proteins (49C and CGG) expressed in Shuffle cells were incubated at 30° C. before and after induction. Cell pellets were thawed and resuspended in 5 mL/g of lysis buffer (50 mM Tris pH 8, 1 M NaCl, 10 mM imidazole, 100 mM AEBSF, 10 mg/mL lysozyme) and lysed by sonication on ice. The lysate was clarified by centrifugation at 15000 rpm for 30 min, filtered through a 0.22 µm membrane before loading on a HisTrap FF 5 mL (GE Healthcare Life Sciences). The His-tagged G20c protein was eluted using a gradient to 100% Buffer B (1 M NaCl, 50 mM Tris pH 7.5, 500 mM imidazole) over 10 column volumes. Fractions of the purified protein were pooled, buffer exchanged into 50 mM Tris pH 8, 500 mM NaCl 50 mM potassium glutamate, and the histidine tag removed by 3C protease digestion at rt overnight. The cleaved protein was then further purified over a HisTrap FF 5 mL. Fractions containing cleaved G20c protein were pooled, concentrated, and finally purified on a 16/600 Superose 6 (GE healthcare Life Sciences) gel filtration column in 20 mM Tris pH8, 1 M NaCl, 50 mM potassium glutamate, concentrated by ultrafiltration using a 100 kDa cutoff filter (Vivaspin) to ~4 mg/mL for biophysical experiments or ~10 mg/mL for crystallographic studies, snap frozen on liquid nitrogen and stored at −80° C. Proteins containing the L49C mutation were purified in buffers containing 2 mM DTT.

Likewise, other mutant proteins taught herein were expressed and purified in a similar fashion as described in the preceding paragraph.

2. Protein Engineering and Purification:

Mutant portal proteins, CGG (33) was produced as described in Section 1 ("Preparation of CGG and CD/N"), above, in *E. coli*, and CD/N was prepared in an analogous fashion, with the exception that two buffer exchange steps over a desalting column (GE Healthcare) were used to improve 3C cleavage of the histidine affinity tag (50 mM Tris pH 8, 500 mM NaCl, 50 mM K Glutamate, 1 mM DTT) prior to a second IMAC step and purification to homogeneity in 20 mM Tris pH 8, 1 M NaCl, 1 mM DTT, before freezing in liquid nitrogen and storage at −80° C. Protein was exchanged into 20 mM Tris pH 7.5, 0.5 M NaCl buffer (Zeba Spin Columns, Thermofisher) for use in hybrid nanopore formation. CD/N mutant proteins where characterized for stability and assembly state by nanoDSF and negative stained TEM.

3. Experimental Set-Up:

Nanopores were fabricated in 30 nm thick SiN membranes using previously reported methods (58,59). The pore diameters ranged between 5.4 and 6 nm in order to squeeze properly the portal protein. Nanopores were cleaned with hot piranha (3:1 $H_2SO_4/H_2O_2$), followed by hot deionized water before each experiment. After being dried under vacuum, nanopore chips were assembled in a custom cell equipped with Ag/AgCl electrodes, and quick-curing silicone elastomer was applied between the chip and the cell to seal the device and thereby reduce the noise by minimizing the chip capacitance. We introduced 0.5 M NaCl, 20 mM Tris pH 7.5 as an electrolyte solution onto both sides of the chip. Portal protein was always added to the trans chamber and the biopolymers to the cis chamber. All experiments were carried out at ambient temperature. Human insulin was purchased from Alfa Aesar (Thermofisher), dsDNA Hairpin (5'-GCTGTCTGTTGCTCTCTCGCAACAGACAGC $T_{50}$-3') (SEQ ID NO:42), ssDNA (5'-$dA_{20}dC_{20}dA_{20}$-3') SEQ ID NO:43), 60 bp-polydT30 ((5'-TCAGGGTTTTTTTACT)$_4$ $T_{30}$-3') SEQ ID NO:44) and its complementary strand ((3'-AGTAAAAAAACCCTGA-5')$_4$) SEQ ID NO:45) were synthesized by Integrated DNA Technology.

4. Electrical Detection and Data Acquisition:

The ionic current through SS nanopores and portal hybrid protein was measured using an Axopatch 200B amplifier (Molecular Devices). Data were filtered at 10 kHz and acquired at 250 kHz using the DigiData 1200 digitizer with a custom National Instruments LabVIEW program. Data was processed and events were detected using Python software (https://github.com/rhenley/Pyth-Ion/). The values for the open pore current ($I_0$) and the standard deviation of the noise (a) was extracted. (The threshold (Th) applied in Python to separate events from the noise is given by Th=$I_0$−4σ. The average duration of blockades is deduced from the distribution of blockade duration, $\tau_t$. The two blockade time distributions of independent events are adjusted with a double exponential function, y=$A_1$ exp(t/$\tau_1$)+$A_2$ exp(t/$\tau_2$). All statistical analyses were performed using Igor Pro software (WaveMetrics Inc.).

Definitions and Discussion of Terminology

As used herein, a "protein" is a biological molecule consisting of one or more chains of amino acids. Proteins differ from one another primarily in their sequence of amino acids, which is dictated by the nucleotide sequence of the encoding gene. A peptide is a single linear polymer chain of two or more amino acids bonded together by peptide bonds between the carboxyl and amino groups of adjacent amino acid residues; multiple peptides in a chain can be referred to as a polypeptide. Proteins can be made of one or more polypeptides. Shortly after or even during synthesis, the residues in a protein are often chemically modified by posttranslational modification, which alters the physical and chemical properties, folding, stability, activity, and ultimately, the function of the proteins. Sometimes proteins have non-peptide groups attached, which can be called prosthetic groups or cofactors.

As used herein, a "protein variant" refers to a protein that differs from a reference peptide by one or more modifications, for example, substitutions, insertions or deletions, and is not naturally occurring. A protein variant can include an isolated protein, which is not naturally occurring, and is free from the cell, or other proteins in a medium, in which it was produced. An isolated protein is a protein or fragment thereof that is substantially free of other proteins, and encompasses proteins that are isolated to a higher purity, such as proteins that are 80%, 81%, 82%, 83%, 84%, 85%, 86%, 87%, 88%, 89%, 90%, 91%, 92%, 93%, 94%, 95%, 96%, 97%, 98%, 99% or 100% pure. The protein can, for example, be isolated from the extracellular medium in which the microorganism to be assayed is growing, or from the cell membrane of the microorganism, using standard protein purification techniques, described, for example, in (See, e.g., Ausubel, F. M. et al. ("*Current Protocols in Molecular Biology*", John Wiley & Sons, (1998) the entire teachings of which are incorporated herein by reference).

The proteins of embodiments also encompass fragments and sequence variants of the proteins described herein. Variants include a substantially homologous protein encoded by the same genetic locus in an organism, i.e., an allelic variant, as well as other variants. Variants also encompass proteins derived from other genetic loci in an organism. Variants also include proteins substantially homologous or identical to these proteins but derived from another organism and/or d and 1 isomers (i.e., an ortholog), produced by chemical synthesis, or produced by recombinant methods.

In some embodiments, the protein variant comprises an amino acid sequence, such as one of the sequences listed herein or a sequence having at least 50%, 60%, 70%, 80%, 85%, 90%, 95%, or 99% sequence identity to one of the sequences listed herein, as determined using a sequence comparison program and parameters described herein.

The percent identity of two amino acid sequences can be determined by aligning the sequences for optimal comparison purposes (e.g., gaps can be introduced in the sequence of a first sequence). The amino acids at corresponding positions are then compared, and the percent identity between the two sequences is a function of the number of identical positions shared by the sequences (i.e., % identity=# of identical positions/total # of positions×100). In certain embodiments, the length of the amino acid sequence aligned for comparison purposes is at least 30%, preferably, at least 40%, more preferably, at least 60%, and even more preferably, at least 70%, 80%, 90%, or 100% of the length of the reference sequence. The actual comparison of the two sequences can be accomplished by well-known methods, for example, using a mathematical algorithm. A preferred, non-limiting example of such a mathematical algorithm is described in Karlin et al., 90 PROC. NAT'L ACAD. SCI. USA 5873-77 (1993), which is incorporated herein by reference. Such an algorithm is incorporated into the BLAST programs (version 2.2) as described by Schaffer et al., 29 NUCLEIC ACIDS RES. 2994-3005 (2001), which is incorporated herein by reference. When utilizing BLAST and Gapped BLAST programs, the default parameters of the respective programs can be used. In one embodiment, the database searched is a non-redundant database, and parameters for sequence comparison can be set at: no filters; Expect value of 10; Word Size of 3; the Matrix is BLOSUM62; and Gap Costs have an Existence of 11 and an Extension of 1.

In another embodiment, the percent identity between two amino acid sequences can be determined by using the GAP program in the GCG software package (available from Accelrys, Inc. of San Diego, CA) using either a Blossom 63 matrix or a PAM250 matrix, and a gap weight of 12, 10, 8, 6, or 4 and a length weight of 2, 3, or 4. In yet another embodiment, the percent identity between two nucleic acid sequences can be determined using a gap weight of 50 and a length weight of 3. Other preferred sequence comparison methods are described herein.

The invention also encompasses proteins having a lower degree of identity but having sufficient similarity so as to perform one or more of the same functions performed by a protein encoded by a nucleic acid molecule of the invention (e.g., the ability to provide the hydrophilic protein channel in a stable insertion fit within a solid-state pore opening). Similarity is determined by conserved amino acid substitution. Such substitutions are those that substitute a given amino acid in a peptide by another amino acid of like characteristics. Conservative substitutions are likely to be phenotypically silent. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., SCIENCE 247:1306-10 (1990), which is incorporated herein by reference.

Functional variants can also contain substitution of similar amino acids that result in no change or an insignificant change in function. Alternatively, such substitutions may positively or negatively affect function to some degree. Non-functional variants typically contain one or more non-conservative amino acid substitutions, deletions, insertions, inversions, or truncations or a substitution, insertion, inversion, or deletion in a critical residue or critical region.

The invention also includes protein and peptide fragments of the amino acid sequences of the various mentioned proteins or variants (e.g., functional variants) thereof.

Fragments can be discrete (not fused to other amino acids or peptides) or can be within a larger peptide. Further, several fragments can be comprised within a single larger peptide. The peptides can, for example, be produced using standard recombinant protein techniques (See, e.g., Ausubel, F. M. et al. ("*Current Protocols in Molecular Biology*", John Wiley & Sons, (1998) the entire teachings of which are incorporated herein by reference). In addition, the proteins of the present invention can also be generated using recombinant techniques.

In some embodiments, protein variants are produced by mutation of amino acid sequences, but protein variants in embodiments can also be produced by removing or adding one or more amino acid residues through other well-known means, including chemical synthesis.

As used herein, a "modification" of a protein refers to a substitution, insertion or deletion of one or more amino acids.

As used herein, a "modification of an amino acid sequence" refers to a mutant amino acid sequence that is not naturally occurring, and that has a mutation relative to a reference amino acid sequence, that is, by an alteration of the amino acid sequence of the reference amino acid sequence, such as by substitution, insertion or deletion of one or more amino acid residues.

As used herein, "nucleic acid" refers to a macromolecule composed of chains (a polymer or an oligomer) of monomeric nucleotide. The most common nucleic acids are deoxyribonucleic acid (DNA) and ribonucleic acid (RNA). It should be further understood that the present invention can be used for sensing biomolecules containing artificial nucleic acids such as peptide nucleic acid (PNA), morpholino, locked nucleic acid (LNA), glycol nucleic acid (GNA) and threose nucleic acid (TNA), among others. In various embodiments of the present invention, nucleic acids can be derived from a variety of sources such as bacteria, virus, humans, and animals, as well as sources such as plants and fungi, among others. The source can be a pathogen. Alternatively, the source can be a synthetic organism. Nucleic acids can, for example, be genomic, extrachromosomal or synthetic. In addition, the term "nucleic acid," is used herein to include a polymeric form of nucleotides of any length, including, but not limited to, ribonucleotides or deoxyribonucleotides. Further, the term refers only to the primary structure of the molecule. Thus, in certain embodiments the term can include triple-, double- and single-stranded DNA, PNA, complementary DNA (cDNA), as well as triple-, double- and single-stranded RNA. It can also include modifications, such as by methylation and/or by capping, and unmodified forms of a polynucleotide. More particularly, the term "nucleic acid," includes polydeoxyribonucleotides (containing 2-deoxy-D-ribose), polyribonucleotides (containing D-ribose), any other type of polynucleotide which is an N- or C-glycoside of a purine or pyrimidine base, and other polymers containing nonnucleotidic backbones, for example, polyamide (e.g., peptide nucleic acids (PNAs)) and polymorpholino (commercially available from Anti-Virals, Inc., Corvallis, Oreg., U.S.A., as Neugene) polymers, and other synthetic sequence-specific nucleic acid polymers providing that the polymers contain nucleobases in a configuration which allows for base pairing and base stacking, such as is found in DNA and RNA. In addition, a "nucleic acid" can include a plasmid DNA (pDNA), such as a plasmid DNA vector.

As used herein, a "modification of a nucleic acid sequence" refers to a mutant nucleic acid (e.g., DNA) that is not naturally occurring, and that has a mutation relative to a reference nucleic acid, that is, by an alteration of the nucleotide sequence of the reference nucleic acid sequence, such as by substitution, insertion or deletion of one or more nucleotides. In some embodiments, the mutation can be a missense mutation, which is a type of nonsynonymous substitution that is a point mutation in which a single nucleotide change results in a codon that codes for a different amino acid. In some embodiments, modifications of a nucleic acid sequence produce modified proteins and peptides described herein.

In some embodiments, a nucleic acid molecule comprising a modification of a nucleic acid sequence can be isolated or recombinant. In addition, such a modification of a nucleic acid sequence can be produced using techniques of cell-free protein synthesis, which produce protein using biological machinery in a cell-free system, without the use of living cells. Cell free expression systems can, for example, be used, that use linear DNA sequences propagated by polymerase chain reaction (PCR) reactions.

As used herein, a "vector" is a molecule, e.g., a plasmid or virus designed for gene expression in cells. The vector is used to introduce a specific gene into a target cell, and can commandeer the cell's mechanism for protein synthesis to produce the protein encoded by the gene. In addition, in some embodiments, a "vector" comprising a modification of a nucleic acid sequence can refer to any DNA plasmid containing the sequence for propagation of the DNA plasmid and/or for expression of the peptide encoded by the modification of a nucleic acid sequence in any cellular system (such as a bacteria, yeast or eukaryotic cell system).

Modifications of a nucleic acid sequence taught herein can, for example, be produced using the techniques taught in "Improved Methods for Site-directed Mutagenesis using NEBuilder® HiFi DNA Assembly Master Mix," New England BioLabs® Inc., Ipswich, Massachusetts, U.S.A., found at the URL..https://www.neb.com/applications/cloning-and-synthetic-biology/dna-assembly-and-cloning/-/media/nebus/files/application-notes/improved-methods-for-site-directed-mutagenesis-using- nebuilder-hifi-dna-assembly-master-mix.pdf.. where ".." replaces a hyperlink. Other means of mutating or modifying nucleic acids are well known in the art.

As used herein, a "biomolecule" refers to a nucleic acid, a protein, a biopolymer, or any other biological molecule, or an organic molecule, or fragment or variant thereof, or any combination of such nucleic acids, proteins, biopolymers, other biological molecules, or organic molecules, or any combination thereof. For example, the biomolecule can, in some embodiments, be or include single-stranded DNA, double-stranded DNA or RNA. In addition, a "biomolecule" can include (1) an antibody, such as a monoclonal antibody, or another ligand specific molecule, and (2) other molecules that may have or could affect biologic and/or cellular activity.

In some embodiments, a protein included in a hydrophilic protein channel comprises a modification of SEQ ID NO: 1, the modification comprising one of: SEQ ID NO: 27; SEQ ID NO: 11; SEQ ID NO: 37; SEQ ID NO: 15, SEQ ID NO: 17, SEQ ID NO: 21, SEQ ID NO: 23, SEQ ID NO: 25, SEQ ID NO: 19, SEQ ID NO: 9, SEQ ID NO: 13, SEQ ID NO: 29, SEQ ID NO: 31, SEQ ID NO: 35, SEQ ID NO: 33, SEQ ID NO: 3, SEQ ID NO: 5, and SEQ ID NO: 7.

In another embodiment, a protein included in a hydrophilic protein channel comprises a modification of SEQ ID NO: 1, the modification comprising one of: SEQ ID NO: 27; SEQ ID NO: 37; SEQ ID NO: 15, SEQ ID NO: 17, SEQ ID NO: 23, SEQ ID NO: 25, SEQ ID NO: 19, SEQ ID NO: 9, SEQ ID NO: 13, SEQ ID NO: 29, SEQ ID NO: 31, SEQ ID NO: 35, SEQ ID NO: 33, SEQ ID NO: 3, SEQ ID NO: 5, and SEQ ID NO: 7.

In other embodiments, a protein variant comprises a modification of SEQ ID NO: 1, the modification comprising one of: SEQ ID NO: 27; SEQ ID NO: 11; SEQ ID NO: 37; SEQ ID NO: 15, SEQ ID NO: 17, SEQ ID NO: 21, SEQ ID NO: 23, SEQ ID NO: 25, SEQ ID NO: 19, SEQ ID NO: 9, SEQ ID NO: 13, SEQ ID NO: 29, SEQ ID NO: 31, SEQ ID NO: 35, SEQ ID NO: 33, SEQ ID NO: 3, SEQ ID NO: 5, and SEQ ID NO: 7.

In another embodiment, a protein variant comprises a modification of SEQ ID NO: 1, the modification comprising one of: SEQ ID NO: 27; SEQ ID NO: 37; SEQ ID NO: 15, SEQ ID NO: 17, SEQ ID NO: 23, SEQ ID NO: 25, SEQ ID NO: 19, SEQ ID NO: 9, SEQ ID NO: 13, SEQ ID NO: 29, SEQ ID NO: 31, SEQ ID NO: 35, SEQ ID NO: 33, SEQ ID NO: 3, SEQ ID NO: 5, and SEQ ID NO: 7.

In other embodiments, a nucleic acid molecule comprises a modification of a nucleic acid sequence of SEQ ID NO: 2, the modification of the nucleic acid sequence comprising one of: SEQ ID NO: 28; SEQ ID NO: 12; SEQ ID NO: 38; SEQ ID NO: 16, SEQ ID NO: 18, SEQ ID NO: 22, SEQ ID NO: 24, SEQ ID NO: 26, SEQ ID NO: 20, SEQ ID NO: 10, SEQ ID NO: 14, SEQ ID NO: 30, SEQ ID NO: 32, SEQ ID NO: 36, SEQ ID NO: 34, SEQ ID NO: 4, SEQ ID NO: 6, and SEQ ID NO: 8.

In another embodiment, a nucleic acid molecule comprises a modification of a nucleic acid sequence of SEQ ID NO: 2, the modification of the nucleic acid sequence comprising one of: SEQ ID NO: 28; SEQ ID NO: 38; SEQ ID NO: 16, SEQ ID NO: 18, SEQ ID NO: 24, SEQ ID NO: 26, SEQ ID NO: 20, SEQ ID NO: 10, SEQ ID NO: 14, SEQ ID NO: 30, SEQ ID NO: 32, SEQ ID NO: 36, SEQ ID NO: 34, SEQ ID NO: 4, SEQ ID NO: 6, and SEQ ID NO: 8.

In other embodiments, a protein variant is encoded by a modification of a nucleic acid sequence of SEQ ID NO: 2, the modification of the nucleic acid sequence comprising one of: SEQ ID NO: 28; SEQ ID NO: 12; SEQ ID NO: 38; SEQ ID NO: 16, SEQ ID NO: 18, SEQ ID NO: 22, SEQ ID NO: 24, SEQ ID NO: 26, SEQ ID NO: 20, SEQ ID NO: 10, SEQ ID NO: 14, SEQ ID NO: 30, SEQ ID NO: 32, SEQ ID NO: 36, SEQ ID NO: 34, SEQ ID NO: 4, SEQ ID NO: 6, and SEQ ID NO: 8.

In another embodiment, a protein variant is encoded by a modification of a nucleic acid sequence of SEQ ID NO: 2, the modification of the nucleic acid sequence comprising one of: SEQ ID NO: 28; SEQ ID NO: 38; SEQ ID NO: 16, SEQ ID NO: 18, SEQ ID NO: 24, SEQ ID NO: 26, SEQ ID NO: 20, SEQ ID NO: 10, SEQ ID NO: 14, SEQ ID NO: 30, SEQ ID NO: 32, SEQ ID NO: 36, SEQ ID NO: 34, SEQ ID NO: 4, SEQ ID NO: 6, and SEQ ID NO: 8.

In other embodiments, a vector comprises a modification of a nucleic acid sequence of SEQ ID NO: 2, the modification of the nucleic acid sequence comprising one of: SEQ ID NO: 28; SEQ ID NO: 12; SEQ ID NO: 38; SEQ ID NO: 16, SEQ ID NO: 18, SEQ ID NO: 22, SEQ ID NO: 24, SEQ ID NO: 26, SEQ ID NO: 20, SEQ ID NO: 10, SEQ ID NO: 14, SEQ ID NO: 30, SEQ ID NO: 32, SEQ ID NO: 36, SEQ ID NO: 34, SEQ ID NO: 4, SEQ ID NO: 6, and SEQ ID NO: 8.

In another embodiment, a vector comprises a modification of a nucleic acid sequence of SEQ ID NO: 2, the modification of the nucleic acid sequence comprising one of: SEQ ID NO: 28; SEQ ID NO: 38; SEQ ID NO: 16, SEQ ID NO: 18, SEQ ID NO: 24, SEQ ID NO: 26, SEQ ID NO: 20, SEQ ID NO: 10, SEQ ID NO: 14, SEQ ID NO: 30, SEQ ID NO: 32, SEQ ID NO: 36, SEQ ID NO: 34, SEQ ID NO: 4, SEQ ID NO: 6, and SEQ ID NO: 8.

In other embodiments, a cell comprises a vector that comprises a modification of a nucleic acid sequence of SEQ ID NO: 2, the modification of the nucleic acid sequence comprising one of: SEQ ID NO: 28; SEQ ID NO: 12; SEQ ID NO: 38; SEQ ID NO: 16, SEQ ID NO: 18, SEQ ID NO: 22, SEQ ID NO: 24, SEQ ID NO: 26, SEQ ID NO: 20, SEQ ID NO: 10, SEQ ID NO: 14, SEQ ID NO: 30, SEQ ID NO: 32, SEQ ID NO: 36, SEQ ID NO: 34, SEQ ID NO: 4, SEQ ID NO: 6, and SEQ ID NO: 8.

In another embodiment, a cell comprises a vector that comprises a modification of a nucleic acid sequence of SEQ ID NO: 2, the modification of the nucleic acid sequence comprising one of: SEQ ID NO: 28; SEQ ID NO: 38; SEQ ID NO: 16, SEQ ID NO: 18, SEQ ID NO: 24, SEQ ID NO: 26, SEQ ID NO: 20, SEQ ID NO: 10, SEQ ID NO: 14, SEQ ID NO: 30, SEQ ID NO: 32, SEQ ID NO: 36, SEQ ID NO: 34, SEQ ID NO: 4, SEQ ID NO: 6, and SEQ ID NO: 8.

As used herein, a "nanopore" refers to a pore with a maximum pore dimension of less than about 20 nanometers, such as less than about 10 nanometers, or less than about 5 nanometers, or about 2 nanometers or less.

As used herein, a "solid-state matrix" refers to matrix made of a solid-state material, which is non-molecular solid material. For example, the solid-state matrix can be made of materials such as a silicon-containing nitride (e.g., silicon nitride), a silicon-containing carbide (e.g., silicon carbon), a silicon-containing oxide (e.g. silicon oxide), nickel, silicon, hafnium, or other solid-state materials.

As used herein, a "solid-state pore opening" refers to a pore opening formed in a solid-state matrix.

As used herein, a "hydrophilic protein" refers to a protein that includes residues that are soluble in water, at least over a substantial portion of a surface that is in contact with the water, such as an external surface of the hydrophilic protein.

As used herein, a "hydrophilic protein channel" refers to a protein structure comprising a channel opening therethrough, the structure being formed by one or more hydrophilic proteins.

As used herein a "stable insertion fit" of a hydrophilic protein channel within a solid-state pore opening refers to a substantially snug fit of the hydrophilic protein channel's external surface within the solid-state pore opening, such that the hydrophilic protein channel is stable for at least 2 hours, for example more than 3 hours, 4 hours, 5 hours or more, including substantially permanently stable, in the solid-state pore opening, while in the presence of a water solvent.

As used herein, a "protein nanopore channel" refers to a channel opening formed by and through a protein, the channel having a diameter less than about 20 nanometers, such as less than about 10 nanometers, or less than about 5 nanometers, or about 2 nanometers or less.

As used herein, a "wing loop residue" refers to an amino acid residue in a portion of a protein that is positioned in a substantially wing-shaped external portion of the protein. For example, on the portal protein of the *Thermus thermophilus* bacteriophage G20c, the wing loop residue can be one of the residues 36-41 or 46-54.

As used herein, a "tunnel loop residue" refers to an amino acid residue in a portion of a protein that forms an intruding loop within a channel that is formed by the protein, such as by multiple monomers of the protein or within a single monomer of the protein. For example, on the portal protein of the *Thermus thermophilus* bacteriophage G20c, the tunnel loop residue can be one of the residues 316-335.

As used herein, an "upper internal surface residue" refers to an amino acid residue in a portion of a protein that forms an internal surface of a tunnel portion of a channel that is formed by the protein, such as by multiple monomers of the protein or within a single monomer of the protein, and that is positioned "upwards" as determined by an accepted orientation of the protein, for example one that is in a "cap" portion of a cork-shaped protein that becomes inserted in a pore with its cap portion upwards and its "stem" portion embedded further into the pore. For example, on the portal protein of the *Thermus thermophilus* bacteriophage G20c, the upper internal surface residue can be one of the residues 381-400.

As used herein, a "lower internal surface residue" refers to an amino acid residue in a portion of a protein that forms an internal surface of a tunnel portion of a channel that is formed by the protein, such as by multiple monomers of the protein or within a single monomer of the protein, and that is positioned "downwards" or in a lower portion as determined by an accepted orientation of the protein, for example one that is in a "stem" portion of a cork-shaped protein that becomes inserted in a pore with its cap portion upwards and its "stem" portion embedded further into the pore. For example, on the portal protein of the *Thermus thermophilus* bacteriophage G20c, the lower internal surface residue can be one of the residues 273-303.

As used herein, an "external surface residue" refers to a residue on an outer surface of the protein, such as one that is exposed to a solid-state pore. For example, on the portal protein of the *Thermus thermophilus* bacteriophage G20c, the external surface residue can be residue 230, although is not limited to that residue and can include other external surface residues.

Tables and Sequences on Protein Versions and the Associated DNA

The below tables, Tables 1-7, provide properties of protein versions taught herein, and the associated DNA. In the left column of each table, the protein version is provided, corresponding to the same protein version listed in the other tables.

TABLE 1

Protein Version with Mutant Grouping and Amino Acid Range

| Protein Version | Mutant Grouping | Amino Acid Range |
|---|---|---|
| WT Full Length | None | 1-448 |
| WT 1-438 C-term | C-terminal Extension | 1-438 |
| WT 1-438 3C prot | WT | 1-438 |
| WT Nanopore | WT | 25-438 |
| L230E | External Surface | 25-438 |
| 49C | Wing Loops | 25-438 |
| 40E | Wing Loops | 25-438 |
| G | Tunnel Loops | 25-438 |
| M | Tunnel Loops | 25-438 |
| K | Tunnel Loops | 25-438 |
| CGG | Wing Loops/Tunnel Loops | 25-438 |
| Loop2GG | Tunnel Loops | 25-438 |
| 49CLoop3G | Tunnel Loops | 25-438 |
| CD/N | Wing Loops/Lower Tunnel | 25-438 |
| SIN1 | Wing Loop Insertion | 25-438 |
| SIN2 | Wing Loop Insertion | 25-438 |
| SIN3 | N-Terminal Extension | 25-438 |
| SIN4 | Wing Loop Insertion | 25-438 |
| 400C | Upper Tunnel/Crown | 1-438 |

TABLE 2

Protein Version with Expression Construct and Affinity Purification Tag

| Protein Version | Expression Construct | Affinity Purification Tag |
|---|---|---|
| WT Full Length | None | None |
| WT 1-438 C-term | pET22b | C-terminal HexaHistidine |
| WT 1-438 3C prot | pYSBL_Lic+ | N-terminal HexaHistidine 3CProtease |
| WT Nanopore | pYSBL_Lic+ | N-terminal HexaHistidine 3CProtease |
| L230E | pYSBL_Lic+ | N-terminal HexaHistidine 3CProtease |
| 49C | pYSBL_Lic+ | N-terminal HexaHistidine 3CProtease |
| 40E | pYSBL_Lic+ | N-terminal HexaHistidine 3CProtease |
| G | pYSBL_Lic+ | N-terminal HexaHistidine 3CProtease |
| M | pYSBL_Lic+ | N-terminal HexaHistidine 3CProtease |

TABLE 2-continued

Protein Version with Expression Construct and Affinity Purification Tag

| Protein Version | Expression Construct | Affinity Purification Tag |
| --- | --- | --- |
| K | pYSBL_Lic+ | N-terminal HexaHistidine 3CProtease |
| CGG | pYSBL_Lic+ | N-terminal HexaHistidine 3CProtease |
| Loop2GG | pYSBL_Lic+ | N-terminal HexaHistidine 3CProtease |
| 49CLoop3G | pYSBL_Lic+ | N-terminal HexaHistidine 3CProtease |
| CD/N | pYSBL_Lic+ | N-terminal HexaHistidine 3CProtease |
| SIN1 | pYSBL_Lic+ | N-terminal HexaHistidine 3CProtease |
| SIN2 | pYSBL_Lic+ | N-terminal HexaHistidine 3CProtease |
| SIN3 | pYSBL_Lic+ | N-terminal HexaHistidine 3CProtease |
| SIN4 | pYSBL_Lic+ | N-terminal HexaHistidine 3CProtease |
| 400C | pYSBL_Lic+ | C-terminal HexaHistidine |

In the below sequences, the affinity tags in the protein sequence are included for those constructs where they are not removed post purification, for example, SEQ ID NO: 3 and SEQ ID NO: 37. However, since histidine tags can perturb nucleic acid interaction with proteins, particularly a circular ring of twelve such tags as is formed in a dodecameric assembly of proteins, the final purified protein (with, for example, a hexahistadine tag) can be cleaved with 3C protease to remove the hexahistidine tag, leaving GPA as the remaining part of the tag at the N-terminus of the protein. Hence, GPA is the sequence for the N-terminal 3 amino acids for the following sequence listings, which reflect those proteins after having been cleaved: SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33 and SEQ ID NO: 35. However, the full length tag sequence present prior to cleavage is included in the DNA sequence of the full open reading frame used to express the protein in *E. coli*. For the protein version WT Nanopore, below, the full length amino acid sequence prior to cleavage is given in SEQ ID NO: 39. The cleaved amino acid sequence of this protein is given in SEQ ID NO: 7.

TABLE 3

Protein Version with Amino Acid Mutation
Residue position number in full length wild type (WT) amino acid sequence.

| Protein Version | Amino Acid Mutation | Insert Sequence |
| --- | --- | --- |
| WT Full Length | N/A | |
| WT 1-438 C-term | N/A (cleaving off residues 439 through 448) | |
| WT 1-438 3C prot | N/A (cleaving off residues 439 through 448) | |
| WT Nanopore | N/A (cleaving off residues 1 through 24 and 439 through 448) | |
| L230E | L230E | |
| 49C | L49C | |
| 40E | V40E | |
| G | V325G | |
| M | V325M | |
| K | I328K | |
| CGG | L49C/V325G/I328G | |
| Loop2GG | V325G/Δ326/A327G/I328G | |
| 49CLoop3G | L49C/Δ281-296G | |
| CD/N | L49C/D281N/D286N/D289N/D296N/V352A | |
| SIN1 | Insert E48_GTPGSRG_L49/D281N/D286N/D289N/D296N | SEQ ID NO: 46 |
| SIN2 | Insert E48_GRKLPDAG_L49/D281N/D286N/D289N/D296N | SEQ ID NO: 47 |
| SIN3 | Insert SSKKSGSYSGSKGS_K25/L49C/D281N/D286N/D289N/D296N | SEQ ID NO: 48 |
| SIN4 | Insert E48_GYRPGFYFR_L49/D281N/D286N/D289N/D296N | SEQ ID NO: 49 |
| 400C | D400C | |

TABLE 4

Protein Version with DNA Mutation
Nucleotide position number in the full length wild type
DNA sequence of the open reading frame coding for the
protein.

| Protein Version | DNA Mutation | WT Sequence Replaced | Insert Sequence |
|---|---|---|---|
| WT Full Length | N/A | | |
| WT 1-438 C-term | N/A | | |
| WT 1-438 3C prot | N/A | | |
| WT Nanopore | N/A | | |
| L230E | GAG_681-683_CTC | | |
| 49C | CTA_139-141_TGT | | |
| *40E | T_119_A | | |
| G | GTA_973-975_GGA | | |
| *M | GTA_973-975_ATG | | |
| K | TA_983-984_AG | | |
| CGG | CTA_139-141_TGT/GTA_973-975_GGA/ATA_982-984_GGA | | |
| Loop2GG | GTACAGGCGATA_973-984_GGAGGCGGT | | SEQ ID NO: 50 |
| 49CLoop3G | CTA_139-141_TGT/AACATGGGGGTACAGGCGATAAAC_964-987_GGT | | SEQ ID NO: 51 |
| CD/N | CTA_139-141_TGT/G_841_A/G_856_A/G_865_A/G_886_A/T_1055_C | | |
| SIN1 | Insert GAG_143-145_GGTACGCCAGGTTCTCGCGGC_146-148_CTA | | SEQ ID NO: 52 |
| SIN2 | Insert GAG_143-145_GGTCGTAAACTGCCGGATGCAGGC_146-148_CTA | | SEQ ID NO: 53 |
| SIN3 | Insert AGCAGTAAGAAAAGTGGAAGCTATAGCGGCAGCAAAGGCAGC_73-75_AAG/CTA_139-141_TGT | | SEQ ID NO: 54 |
| SIN4 | Insert_GAG_143-145_GGATATCGCCCGGGCTTTTATTTTCGC_146-148_CTA | | |
| *400C | GA_1198-1199_TG | | |

Sequences marked with an "*" in Table 4, above, were sequenced in one direction (across the new introduced mutation) and the complete sequence was assembled from the data available from the template used to produce the new mutant construct. All other sequences assembled from original DNA sequencing data.

TABLE 5

Protein Version with Amino Acid Sequence and DNA Sequence

| Protein Version | Amino Acid Sequence | DNA Sequence |
|---|---|---|
| WT Full Length | SEQ ID NO: 1 | SEQ ID NO: 2 |
| WT 1-438 C-term | SEQ ID NO: 3 | SEQ ID NO: 4 |
| WT 1-438 3C prot | SEQ ID NO: 5 | SEQ ID NO: 6 |
| WT Nanopore | SEQ ID NO: 7 | SEQ ID NO: 8 |

TABLE 5-continued

Protein Version with Amino Acid Sequence and DNA Sequence

| Protein Version | Amino Acid Sequence | DNA Sequence |
|---|---|---|
| L230E | SEQ ID NO: 9 | SEQ ID NO: 10 |
| 49C | SEQ ID NO: 11 | SEQ ID NO: 12 |
| 40E | SEQ ID NO: 13 | SEQ ID NO: 14 |
| G | SEQ ID NO: 15 | SEQ ID NO: 16 |
| M | SEQ ID NO: 17 | SEQ ID NO: 18 |
| K | SEQ ID NO: 19 | SEQ ID NO: 20 |
| CGG | SEQ ID NO: 21 | SEQ ID NO: 22 |
| Loop2GG | SEQ ID NO: 23 | SEQ ID NO: 24 |
| 49CLoop3G | SEQ ID NO: 25 | SEQ ID NO: 26 |
| CD/N | SEQ ID NO: 27 | SEQ ID NO: 28 |
| SIN1 | SEQ ID NO: 29 | SEQ ID NO: 30 |
| SIN2 | SEQ ID NO: 31 | SEQ ID NO: 32 |
| SIN3 | SEQ ID NO: 33 | SEQ ID NO: 34 |
| SIN4 | SEQ ID NO: 35 | SEQ ID NO: 36 |
| 400C | SEQ ID NO: 37 | SEQ ID NO: 38 |

TABLE 6

Example-Protein Version with Nanopore Insertion Performed

| Protein Version | Nanopore Insertion Performed |
|---|---|
| WT 1-438 C-term | Thick Hafnium 6-8 nm |
| WT 1-438 3C prot | Thick SiN 6-8 nm |
| WT Nanopore | Thick SiN 6-8 nm |
| 49C | Planar Lipid Bilayer |
| CGG | Thick SiN 6-8 nm/planar lipid bilayer |
| CD/N | Thick SiN 6-8 nm |

TABLE 7

Example-Protein Version with Nanopore Translocation Performed

| Protein Version | Nanopore Translocation Performed |
|---|---|
| 49C | Cyclodextrin |
| CGG | Cyclodextrin |
| CD/N | dsDNA/ssDNA/peptide |

In the below sequences, a letter "X" signifies "any amino acid," and a letter "n" signifies any nucleotide (n=A, T, C or G).

SEQ ID NO: 1
MAKRGRKPKELVPGPGSIDPSDVPKLEGASVPVMS

TSYDVVVDREFDELLQGKDGLLVYHKMLSDGTVKN

ALNYIFGRIRSAKWYVEPASTDPEDIAIAAFIHAQ

LGIDDASVGKYPFGRLFAIYENAYIYGMAAGEIVL

TLGADGKLILDKIVPIHPFNIDEVLYDEEGGPKAL

KLSGEVKGGSQFVSGLEIPIWKTVVFLHNDDGSFT

GQSALRAAVPHWLAKRALILLINHGLERFMIGVPT

LTIPKSVRQGTKQWEAAKEIVKNFVQKPRHGIILP

DDWKFDTVDLKSAMPDAIPYLTYHDAGIARALGID

FNTVQLNMGVQAINIGEFVSLTQQTIISLQREFAS

AVNLYLIPKLVLPNWPSATRFPRLTFEMEERNDFS

AAANLMGMLINAVKDSEDIPTELKALIDALPSKMR

RALGVVDEVREAVRQPADSRYLYTRRRR

SEQ ID NO: 2
ATGGCTAAGCGAGGACGTAAACCCAAAGAGCTGGT

CCCCGGACCTGGCTCCATTGACCCATCTGACGTTC

CCAAGCTCGAGGGCGCCTCCGTGCCGGTGATGTCC

ACCAGTTACGACGTGGTGGTGGACCGGGAGTTTGA

CGAGCTACTGCAGGGCAAGGACGGCTTGCTCGTCT

ACCACAAGATGCTCTCGGACGGCACGGTTAAGAAC

GCCCTCAACTACATCTTCGGACGCATCCGCTCGGC

GAAGTGGTACGTAGAGCCCGCCTCTACCGACCCGG

AAGACATCGCCATCGCCGCCTTCATCCACGCCCAG

TTAGGCATAGACGACGCTTCGGTGGGCAAGTATCC

CTTTGGCCGCCTTTTCGCCATCTACGAAAACGCCT

ACATATACGGCATGGCCGCCGGGGAAATCGTACTA

ACCCTTGGCGCGGACGGCAAGCTCATCCTTGACAA

AATCGTCCCTATCCACCCTTTCAACATTGACGAGG

TGCTTTACGACGAGGAAGGCGGTCCAAAGGCGCTA

AAGCTAAGCGGAGAGGTGAAGGGCGGAAGCCAGTT

TGTGAGCGGGTTGGAGATTCCTATATGGAAGACCG

TGGTCTTCCTGCACAACGACGACGGCTCCTTCACC

GGACAGAGCGCCCTCAGAGCCGCCGTGCCGCATTG

GCTAGCCAAACGAGCCCTCATTCTCCTCATCAACC

ACGGGTTGGAGCGCTTCATGATTGGCGTGCCCACC

CTCACCATCCCCAAGAGCGTGCGTCAGGGAACCAA

GCAATGGGAGGCCGCCAAGGAAATCGTCAAGAACT

TTGTTCAAAAACCACGGCATGGTATAATACTGCCT

GACGACTGGAAGTTTGACACGGTAGACCTGAAGTC

GGCCATGCCCGACGCCATTCCCTACCTGACCTACC

ACGACGCGGGCATCGCTAGGGCGCTTGGCATAGAC

TTCAACACCGTTCAACTAAACATGGGGGTACAGGC

GATAAACATCGGCGAGTTCGTAAGCCTGACCCAGC

AGACCATCATTTCGCTCCAGCGGGAGTTCGCTAGC

GCGGTCAACCTCTACCTCATCCCCAAGCTAGTGCT

```
TCCCAACTGGCCGAGCGCTACTCGCTTTCCTAGGC
TCACCTTTGAGATGGAGGAGCGCAACGACTTCTCC
GCCGCGGCCAACCTTATGGGCATGCTCATCAACGC
GGTTAAGGACTCCGAAGACATTCCCACCGAGCTCA
AGGCGCTAATAGACGCTCTGCCTAGCAAGATGCGC
CGGGCGCTTGGCGTGGTGGACGAGGTGAGGGAAGC
GGTACGCCAACCCGCCGATTCCCGCTACCTGTACA
CGCGAAGGAGGAGGTAG
```

SEQ ID NO: 3
```
MAKRGRKPKELVPGPGSIDPSDVPKLEGASVPVMS
TSYDVVVDREFDELLQGKDGLLVYHKMLSDGTVKN
ALNYIFGRIRSAKWYVEPASTDPEDIAIAAFIHAQ
LGIDDASVGKYPFGRLFAIYENAYIYGMAAGEIVL
TLGADGKLILDKIVPIHPFNIDEVLYDEEGGPKAL
KLSGEVKGGSQFVSGLEIPIWKTVVFLHNDDGSFT
GQSALRAAVPHWLAKRALILLINHGLERFMIGVPT
LTIPKSVRQGTKQWEAAKEIVKNFVQKPRHGIILP
DDWKFDTVDLKSAMPDAIPYLTYHDAGIARALGID
FNTVQLNMGVQAINIGEFVSLTQQTIISLQREFAS
AVNLYLIPKLVLPNWPSATRFPRLTFEMEERNDFS
AAANLMGMLINAVKDSEDIPTELKALIDALPSKMR
RALGVVDEVREAVRQPADLEHHHHHH
```

SEQ ID NO: 4
```
ATGGCTAAGCGAGGACGTAAACCCAAAGAGCTGGT
CCCCGGACCTGGCTCCATTGACCCATCTGACGTTC
CCAAGCTCGAGGGCGCCTCCGTGCCGGTGATGTCC
ACCAGTTACGACGTGGTGGTGGACCGGGAGTTTGA
CGAGCTACTGCAGGGCAAGGACGGCTTGCTCGTCT
ACCACAAGATGCTCTCGGACGGCACGGTTAAGAAC
GCCCTCAACTACATCTTCGGACGCATCCGCTCGGC
GAAGTGGTACGTAGAGCCCGCCTCTACCGACCCGG
AAGACATCGCCATCGCCGCCTTCATCCACGCCCAG
TTAGGCATAGACGACGCTTCGGTGGGCAAGTATCC
CTTTGGCCGCCTTTTCGCCATCTACGAAAACGCCT
ACATATACGGCATGGCCGCCGGGGAAATCGTACTA
ACCCTTGGCGCGGACGGCAAGCTCATCCTTGACAA
AATCGTCCCTATCCACCCTTTCAACATTGACGAGG
TGCTTTACGACGAGGAAGGCGGTCCAAAGGCGCTA
AAGCTAAGCGGAGAGGTGAAGGGCGGAAGCCAGTT
TGTGAGCGGGTTGGAGATTCCTATATGGAAGACCG
TGGTCTTCCTGCACAACGACGACGGCTCCTTCACC
GGACAGAGCGCCCTCAGAGCCGCCGTGCCGCATTG
```

```
GCTAGCCAAACGAGCCCTCATTCTCCTCATCAACC
ACGGGTTGGAGCGCTTCATGATTGGCGTGCCCACC
CTCACCATCCCCAAGAGCGTGCGTCAGGGAACCAA
GCAATGGGAGGCCGCCAAGGAAATCGTCAAGAACT
TTGTTCAAAAACCACGGCATGGTATAATACTGCCT
GACGACTGGAAGTTTGACACGGTAGACCTGAAGTC
GGCCATGCCCGACGCCATTCCCTACCTGACCTACC
ACGACGCGGGCATCGCTAGGGCGCTTGGCATAGAC
TTCAACACCGTTCAACTAAACATGGGGGTACAGGC
GATAAACATCGGCGAGTTCGTAAGCCTGACCCAGC
AGACCATCATTTCGCTCCAGCGGGAGTTCGCTAGC
GCGGTCAACCTCTACCTCATCCCCAAGCTAGTGCT
TCCCAACTGGCCGAGCGCTACTCGCTTTCCTAGGC
TCACCTTTGAGATGGAGGAGCGCAACGACTTCTCC
GCCGCGGCCAACCTTATGGGCATGCTCATCAACGC
GGTTAAGGACTCCGAAGACATTCCCACCGAGCTCA
AGGCGCTAATAGACGCTCTGCCTAGCAAGATGCGC
CGGGCGCTTGGCGTGGTGGACGAGGTGAGGGAAGC
GGTACGCCAACCCGCCGATctcgagcaccaccacc
accaccacTAG
```

SEQ ID NO: 5
```
GPAMAKRGRKPKELVPGPGSIDPSDVPKLEGASVP
VMSTSYDVVVDREFDELLQGKDGLLVYHKMLSDGT
VKNALNYIFGRIRSAKWYVEPASTDPEDIAIAAFI
HAQLGIDDASVGKYPFGRLFAIYENAYIYGMAAGE
IVLTLGADGKLILDKIVPIHPFNIDEVLYDEEGGP
KALKLSGEVKGGSQFVSGLEIPIWKTVVFLHNDDG
SFTGQSALRAAVPHWLAKRALILLINHGLERFMIG
VPTLTIPKSVRQGTKQWEAAKEIVKNFVQKPRHGI
ILPDDWKFDTVDLKSAMPDAIPYLTYHDAGIARAL
GIDFNTVQLNMGVQAINIGEFVSLTQQTIISLQRE
FASAVNLYLIPKLVLPNWPSATRFPRLTFEMEERN
DFSAAANLMGMLINAVKDSEDIPTELKALIDALPS
KMRRALGVVDEVREAVRQPAD
```

SEQ ID NO: 6
```
ATGGGCAGCAGCCATCATcATCATCATCACAGCAG
CGGCCTGGAAGTTCTGTTCCAGGGACCAGCAATGG
CTAAGCGAGGACGTAAACCCAAAGAGCTGGTCCCC
GGACCTGGCTCCATTGACCCATCTGACGTTCCCAA
GCTCGAGGGCGCCTCCGTGCCGGTGATGTCCACCA
GTTACGACGTGGTGGTGGACCGGGAGTTTGACGAG
```

```
CTACTGCAGGGCAAGGACGGCTTGCTCGTCTACCA
CAAGATGCTCTCGGACGGCACGGTTAAGAACGCCC
TCAACTACATCTTCGGACGCATCCGCTCGGCGAAG
TGGTACGTAGAGCCCGCCTCTACCGACCCGGAAGA
CATCGCCATCGCCGCCTTCATCCACGCCCAGTTAG
GCATAGACGACGCTTCGGTGGGCAAGTATCCCTTT
GGCCGCCTTTTCGCCATCTACGAAAACGCCTACAT
ATACGGCATGGCCGCCGGGGAAATCGTACTAACCC
TTGGCGCGGACGGCAAGCTCATCCTTGACAAAATC
GTCCCTATCCACCCTTTCAACATTGACGAGGTGCT
TTACGACGAGGAAGGCGGTCCAAAGGCGCTAAAGC
TAAGCGGAGAGGTGAAGGGCGGAAGCCAGTTTGTG
AGCGGGTTGGAGATTCCTATATGGAAGACCGTGGT
CTTCCTGCACAACGACGACGGCTCCTTCACCGGAC
AGAGCGCCCTCAGAGCCGCCGTGCCGCATTGGCTA
GCCAAACGAGCCCTCATTCTCCTCATCAACCACGG
GTTGGAGCGCTTCATGATTGGCGTGCCCACCCTCA
CCATCCCCAAGAGCGTGCGTCAGGGAACCAAGCAA
TGGGAGGCCGCCAAGGAAATCGTCAAGAACTTTGT
TCAAAAACCACGGCATGGTATAATACTGCCTGACG
ACTGGAAGTTTGACACGGTAGACCTGAAGTCGGCC
ATGCCCGACGCCATTCCCTACCTGACCTACCACGA
CGCGGGCATCGCTAGGGCGCTTGGCATAGACTTCA
ACACCGTTCAACTAAACATGGGGGTACAGGCGATA
AACATCGGCGAGTTCGTAAGCCTGACCCAGCAGAC
CATCATTTCGCTCCAGCGGGAGTTCGCTAGCGCGG
TCAACCTCTACCTCATCCCCAAGCTAGTGCTTCCC
AACTGGCCGAGCGCTACTCGCTTTCCTAGGCTCAC
CTTTGAGATGGAGGAGCGCAACGACTTCTCCGCCG
CGGCCAACCTTATGGGCATGCTCATCAACGCGGTT
AAGGACTCCGAAGACATTCCCACCGAGCTCAAGGC
GCTAATAGACGCTCTGCCTAGCAAGATGCGCCGGG
CGCTTGGCGTGGTGGACGAGGTGAGGGAAGCGGTA
CGCCAACCCGCCGATTAA
                            SEQ ID NO: 7
GPAKLEGASVPVMSTSYDVVVDREFDELLQGKDGL
LVYHKMLSDGTVKNALNYIFGRIRSAKWYVEPAST
DPEDIAIAAFIHAQLGIDDASVGKYPFGRLFAIYE
NAYIYGMAAGEIVLTLGADGKLILDKIVPIHPFNI
DEVLYDEEGGPKALKLSGEVKGGSQFVSGLEIPIW
KTVVFLHNDDGSFTGQSALRAAVPHWLAKRALILL
INHGLERFMIGVPTLTIPKSVRQGTKQWEAAKEIV
KNFVQKPRHGIILPDDWKFDTVDLKSAMPDAIPYL
TYHDAGIARALGIDFNTVQLNMGVQAINIGEFVSL
TQQTIISLQREFASAVNLYLIPKLVLPNWPSATRF
PRLTFEMEERNDFSAAANLMGMLINAVKDSEDIPT
ELKALIDALPSKMRRALGVVDEVREAVRQPAD
                            SEQ ID NO: 8
ATGGGCAGCAGCCATCATcATCATCATCACAGCAG
CGGCCTGGAAGTTCTGTTCCAGGGACCAGCAAAGC
TCGAGGGCGCCTCCGTGCCGGTGATGTCCACCAGT
TACGACGTGGTGGTGGACCGGGAGTTTGACGAGCT
ACTGCAGGGCAAGGACGGCTTGCTCGTCTACCACA
AGATGCTCTCGGACGGCACGGTTAAGAACGCCCTC
AACTACATCTTCGGACGCATCCGCTCGGCGAAGTG
GTACGTAGAGCCCGCCTCTACCGACCCGGAAGACA
TCGCCATCGCCGCCTTCATCCACGCCCAGTTAGGC
ATAGACGACGCTTCGGTGGGCAAGTATCCCTTTGG
CCGCCTTTTCGCCATCTACGAAAACGCCTACATAT
ACGGCATGGCCGCCGGGGAAATCGTACTAACCCTT
GGCGCGGACGGCAAGCTCATCCTTGACAAAATCGT
CCCTATCCACCCTTTCAAcATTGACGAGGTGCTTT
ACGACGAGGaAGGCGGTCCAAAGGCGCTAAAGCTA
AGCGGAGAGGTGAAGGGCGGAAGCCAGTTTGTGAG
CGGGTTGGAGATTCCTATATGGAAGACCGTGGTCT
TCCTGCACAACGACGACGGCTCCTTCACCGGACAG
AGCGCCCTCAGAGCCGCCGTGCCGCATTGGCTAGC
CAAACGAGCCCTCATTCTCCTCATCAACCACGGGT
TGGAGCGCTTCATGATTGGCGTGCCCACCCTCACC
ATCCCCAAGAGCGTGCGTCAGGGAACCAAGCAATG
GGAGGCCGCCAAGGAAATCGTCAAGAACTTTGTTC
AAAAACCacGGCATGGTATAATACTGCCTGACGAC
TGGAAGTTTGACAcGGTAGACCTGAAGTCGGCCAT
GCCCGACGCCATTCCCTACCTGACCTACCACGACG
CGGGCATCGCTAGGGCGCTTGGCATAGACTTCAAC
ACCGTTCAACTAAACATGGGGGTACAGGCGATAAA
CATCGGCGAGTTCGTAAGCCTGACCCAGCAGACCA
TCATTTCGCTCCAGCGGGAGTTCGCTAGCGCGGTC
AACCTCTACCTCATCCCCAAGCTAGTGCTTCCCAA
CTGGCCGAGCGCTACTCGCTTTCCTAGGCTCACCT
TTGAGATGGAGGAGCGCAACGACTTCtcCGCCGCG
GCCAACCTTATGGGCATGCTCATCaACGCGGTTAA
```

-continued

```
GGACTCCGAAGACATTCCCacCGAGCTcaaGGCGC
TAATAGACGCTCTGCCTAGCaAGATGCGCCGGGCG
CTTGGCGTGGTGGACGAGGTGAGGGAAGCGGTACG
CCaACCCGcCgATTAA
```

SEQ ID NO: 9

```
GPAKLEGASVPVMSTSYDVVVDREFDELLQGKDGL
LVYHKMLSDGTVKNALNYIFGRIRSAKWYVEPAST
DPEDIAIAAFIHAQLGIDDASVGKYPFGRLFAIYE
NAYIYGMAAGEIVLTLGADGKLILDKIVPIHPFNI
DEVLYDEEGGPKALKLSGEVKGGSQFVSGLEIPIW
KTVVFLHNDDGSFTGQSALRAAVPHWLAKRALIEL
INHGLERFMIGVPTLTIPKSVRQGTKQWEAAKEIV
KNFVQKPRHGIILPDDWKFDTVDLKSAMPDAIPYL
TYHDAGIARALGIDFNTVQLNMGVQAINIGEFVSL
TQQTIISLQREFASAVNLYLIPKLVLPNWPSATRF
PRLTFEMEERNDFSAAANLMGMLINAVKDSEDIPT
ELKALIDALPSKMRRALGVVDEVREAVRQPAD
```

SEQ ID NO: 10

```
ATGGGCAGCAGCCATcatCAtCATCATCACAGCAG
CGGCCTGGAAGTTCTGTTCCAGGgaCCAGCAAAGC
TCGAGGGCGCCTCCgtGCCGgtgATGTCCACCAGT
TACGACGTGgtGGTGGACCGGGAGTTTGACGAGCT
ACTGCAGGGCAAGGACGGCTTGCTCGTCTACCACA
AGATGCTCTCGGACGGCACGGTTAAGAACGCCCTC
AACTACATCTTCGGACGCATCCGCTCGGCGAAGTG
GTACGTAGAGCCCGCCTCTACCGACCCGGAAGACA
TCGCCATCGCCGCCTTCATCCACGCCCAGTTAGGC
ATAGACGACGCTTCGGTGGGCAAGTATCCCTTTGG
CCGCCTTTTCGCCATCTACGAAAACGCCTACATAT
ACGGCATGGCCGCCGGGGAAATCGTACTAACCCTT
GGCGCGGACGGCAAGCTCATCCTTGACAAAATCGT
CCCTATCCACCCTTTCAACATTGACGAGGTGCTTT
ACGACGAGGAAGGCGGTCCAAAGGCGCTAAAGCTA
AGCGGAGAGGTGAAGGGCGGAAGCCAGTTTGTGAG
CGGGTTGGAGATTCCTATATGGAAGACCGTGGTCT
TCCTGCACAACGACGACGGCTCCTTCACCGGACAG
AGCGCCCTCAGAGCCGCCGTGCCGCATTGGCTAGC
CAAACGAGCCCTCATTGAGCTCATCAACCACGGGT
TGGAGCGCTTCATGATTGGCGTGCCCACCCTCACC
ATCCCCAAGAGCGTGCGTCAGGGAACCAAGCAATG
GGAGGCCGCCAAGGAAATCGTCAAGAACTTTGTTC
AAAAACCACGGCATGGTATAATACTGCCTGACGAC
```

```
TGGAAGTTTGACACGGTAGACCTGAAGTCGGCCAT
GCCCGACGCCATTCCCTACCTGACCTACCACGACG
CGGGCATCGCTAGGGCGCTTGGCATAGACTTCAAC
ACCGTTCAACTAAACATGGGGgTaCAGGCGATAAA
CATCGGCGAGTTCGTAAGCCTGACCcAGCAGACCA
TCATTtCgCTCCAGCGGGAGTtcGCTAGCGCGGTC
AACCTCTACCTCATCCCcAAGCTAGTgcTtCCcAA
CTGGCCGAGCGCTACTCGCTTTCCTAGGCTCACCT
TTGAGATGGAGGAGCGCAACGACTTCtcCGCCGCG
GCCAACCTTATGGGCATGCTCATCaACGCGGTTAA
GGACTCCGAAGACATTCCCacCGAGCTcaaGGCGC
TAATAGACGCTCTGCCTAGCaAGATGCGCCGGGCG
CTTGGCGTGGTGGACGAGGTGAGGGAAGCGGTACG
CCaACCCGcCgATTAA
```

SEQ ID NO: 11

```
GPAKLEGASVPVMSTSYDVVVDREFDECLQGKDGL
LVYHKMLSDGTVKNALNYIFGRIRSAKWYVEPAST
DPEDIAIAAFIHAQLGIDDASVGKYPFGRLFAIYE
NAYIYGMAAGEIVLTLGADGKLILDKIVPIHPFNI
DEVLYDEEGGPKALKLSGEVKGGSQFVSGLEIPIW
KTVVFLHNDDGSFTGQSALRAAVPHWLAKRALILL
INHGLERFMIGVPTLTIPKSVRQGTKQWEAAKEIV
KNFVQKPRHGIILPDDWKFDTVDLKSAMPDAIPYL
TYHDAGIARALGIDFNTVQLNMGVQAINIGEFVSL
TQQTIISLQREFASAVNLYLIPKLVLPNWPSATRF
PRLTFEMEERNDFSAAANLMGMLINAVKDSEDIPT
ELKALIDALPSKMRRALGVVDEVREAVRQPAD
```

SEQ ID NO: 12

```
ATGGGCAGCAGCCATCATCATCATCATCACAGCAG
CGGCCTGgAAGTTCTGTTCCAGGGACCAGCAAAGC
TCGAGGGCGCCTCCgtGCCGGTGATGTCCACCAGT
tACGACGTGGTGGTGGACCGGGAGTTTGACGAGTG
TCTGCAGGGCAAGGACGGCTTGCTCGTCTACCACA
AGATGCTCTCGGACGGCACGGTTAAGAACGCCCTC
AACTACATCTTCGGACGCATCCGCTCGGCGAAGTG
GTACGTAGAGCCCGCCTCTACCGACCCGGAAGACA
TCGCCATCGCCGCCTTCATCCACGCCCAGTTAGGC
ATAGACGACGCTTCGGTGGGCAAGTATCCCTTTGG
CCGCCTTTTCGCCATCTACGAAAACGCCTACATAT
ACGGCATGGCCGCCGGGGAAATCGTACTAACCCTT
GGCGCGGACGGCAAGCTCATCCTTGACAAAATCGT
```

-continued
CCCTATCCACCCTTTCAACATTGACGAGGTGCTTT
ACGACGAGGAAGGCGGTCCAAAGGCGCTAAAGCTA
AGCGGAGAGGTGAAGGGCGGAAGCCAGTTTGTGAG
CGGGTTGGAGATTCCTATATGGAAGACCGTGGTCT
TCCTGCACAACGACGACGGCTCCTTCACCGGACAG
AGCGCCCTCAGAGCCGCCGTGCCGCATTGGCTAGC
CAAACGAGCCCTCATTCTCCTCATCAACCACGGGT
TGGAGCGCTTCATGATTGGCGTGCCCACCCTCACC
ATCCCCAAGAGCGTGCGTCAGGGAACCAAGCAATG
GGAGGCCGCCAAGGAaaTCGTCAAGAACTTtGTTC
AAAAnCCACGGCATGGTATAATACTGCCTGACGAC
TGGAAGTTTGACACGGTAGACCTgAaGTCGGCCAT
GCCCGACGCCATTCCCTACCTGACCTACCACGACG
CGGGCATCGCTAGGGCGCTtGGCATAGACTTcaaC
ACCgTtCAACTAAACATGGGGGTACAGGCGATAAA
CATCGGCGAGTTCGTAAGCCTGACCCAGCAGACCA
TCATTTCGCTCCAGCGGGAGTTCGCTAGCGCGGTC
AACCTCTACCTCATCCCCAAGCTAGTGCTTCCCAA
CTGGCCGAGCGCTACTCGCTTTCCTAGGCTCACCT
TTGAGATGGAGGAGCGCAACGACTTCtcCGCCGCG
GCCAACCTTATGGGCATGCTCATCaACGCGGTTAA
GGACTCCGAAGACATTCCCacCGAGCTcaaGGCGC
TAATAGACGCTCTGCCTAGCaAGATGCGCCGGGCG
CTTGGCGTGGTGGACGAGGTGAGGGAAGCGGTACG
CCaACCCGcCgATTAA SEQ ID NO: 13
GPAKLEGASVPVMSTSYDEVVDREFDELLQGKDGL
LVYHKMLSDGTVKNALNYIFGRIRSAKWYVEPAST
DPEDIAIAAFIHAQLGIDDASVGKYPFGRLFAIYE
NAYIYGMAAGEIVLTLGADGKLILDKIVPIHPFNI
DEVLYDEEGGPKALKLSGEVKGGSQFVSGLEIPIW
KTVVFLHNDDGSFTGQSALRAAVPHWLAKRALILL
INHGLERFMIGVPTLTIPKSVRQGTKQWEAAKEIV
KNFVQXPRHGIILPDDWKFDTVDLKSAMPDAIPYL
TYHDAGIARALGIDFNTVQLNMGVQAINIGEFVSL
TQQTIISLQREFASAVNLYLIPKLVLPNWPSATRF
PRLTFEMEERNDFSAAANLMGMLINAVKDSEDIPT
ELKALIDALPSKMRRALGVVDEVREAVRQPAD SEQ ID NO: 14
ATGGGCAGCAGCCATCATCATCATCATCACAGCAG
CGGCCTgGaAGTTCTGTTCCAGGGACCAGCAAAGC
TCGAGGGCGCCTCCgtGCCGGTGATGTCCACCAGT -continued
tACGACGAGGTGGTGGACCGGGAGTTTGACGAGCT
ACTGCAGGGCAAGGACGGCTTGCTCGTCTACCACA
AGATGCTCTCGGACGGCACGGTTAAGAACGCCCTC
AACTACATCTTCGGACGCATCCGCTCGGCGAAGTG
GTACGTAGAGCCCGCCTCTACCGACCCGGAAGACA
TCGCCATCGCCGCCTTCATCCACGCCCAGTTAGGC
ATAGACGACGCTTCGGTGGGCAAGTATCCCTTTGG
CCGCCTTTTCGCCATCTACGAAAACGCCTACATAT
ACGGCATGGCCGCCGGGGAAATCGTACTAACCCTT
GGCGCGGACGGCAAGCTCATCCTTGACAAAATCGT
CCCTATCCACCCTTTCAACATTGACGAGGTGCTTT
ACGACGAGGAAGGCGGTCCAAAGGCGCTAAAGCTA
AGCGGAGAGGTGAAGGGCGGAAGCCAGTTTGTGAG
CGGGTTGGAGATTCCTATATGGAAGACCGTGGTCT
TCCTGCACAACGACGACGGCTCCTTCACCGGACAG
AGCGCCCTCAGAGCCGCCGTGCCGCATTGGCTAGC
CAAACGAGCCCTCATTCTCCTCATCAACCACGGGT
TGGAGCGCTTCATGATTGGCGTGCCCACCCTCACC
ATCCCCAAGAGCGTGCGTCAGGGAACCAAGCAATG
GGAGGCCGCCAAGGAaaTCGTCAAGAACTTtGTTC
AAAAnCCACGGCATGGTATAATACTGCCTGACGAC
TGGAAGTTTGACACGGTAGACCTgAaGTCGGCCAT
GCCCGACGCCATTCCCTACCTGACCTACCACGACG
CGGGCATCGCTAGGGCGCTtGGCATAGACTTcaaC
ACCgTtCAACTAAACATGGGGGTACAGGCGATAAA
CATCGGCGAGTTCGTAAGCCTGACCCAGCAGACCA
TCATTTCGCTCCAGCGGGAGTTCGCTAGCGCGGTC
AACCTCTACCTCATCCCCAAGCTAGTGCTTCCCAA
CTGGCCGAGCGCTACTCGCTTTCCTAGGCTCACCT
TTGAGATGGAGGAGCGCAACGACTTCtcCGCCGCG
GCCAACCTTATGGGCATGCTCATCaACGCGGTTAA
GGACTCCGAAGACATTCCCacCGAGCTcaaGGCGC
TAATAGACGCTCTGCCTAGCaAGATGCGCCGGGCG
CTTGGCGTGGTGGACGAGGTGAGGGAAGCGGTACG
CCaACCCGcCgATTAA SEQ ID NO: 15
GPAKLEGASVPVMSTSYDVVVDREFDELLQGKDGL
LVYHKMLSDGTVKNALNYIFGRIRSAKWYVEPAST
DPEDIAIAAFIHAQLGIDDASVGKYPFGRLFAIYE
NAYIYGMAAGEIVLTLGADGKLILDKIVPIHPFNI
DEVLYDEEGGPKALKLSGEVKGGSQFVSGLEIPIW

KTVVFLHNDDGSFTGQSALRAAVPHWLAKRALILL

INHGLERFMIGVPTLTIPKSVRQGTKQWEAAKEIV

KNFVQKPRHGIILPDDWKFDTVDLKSAMPDAIPYL

TYHDAGIARALGIDFNTVQLNMGGQAINIGEFVSL

TQQTIISLQREFASAVNLYLIPKLVLPNWPSATRF

PRLTFEMEERNDFSAAANLMGMLINAVKDSEDIPT

ELKALIDALPSKMRRALGVVDEVREAVRQPAD

SEQ ID NO: 16
ATGGGCAGCAGCCATCATcATCATCATCACAGCAG

CGGCCTGGAAGTTCTGTTCCAGGGACCAGCAAAGC

TCGAGGGCGCCTCCGTGCCGGTGATGTCCACCAGT

TACGACGTGGTGGTGGACCGGGAGTTTGACGAGCT

ACTGCAGGGCAAGGACGGCTTGCTCGTCTACCACA

AGATGCTCTCGGACGGCACGGTTAAGAACGCCCTC

AACTACATCTTCGGACGCATCCGCTCGGCGAAGTG

GTACGTAGAGCCCGCCTCTACCGACCCGGAAGACA

TCGCCATCGCCGCCTTCATCCACGCCCAGTTAGGC

ATAGACGACGCTTCGGTGGGCAAGTATCCCTTTGG

CCGCCTTTTCGCCATCTACGAAAACGCCTACATAT

ACGGCATGGCCGCCgggGAAATCGTACTAAcCCtt

GGCGCGGACGGCAAGCTCATCCTTGACaaaATCGT

CCCTAtcCACCCttTCAACATTGACGAGGTGCTTT

ACGACGAGGAAGGCGGTCCAAAGGCGCTAAAGCTA

AGCGGAGAGGTGAAgGGCGGAAGCCAGTTTGTGAG

CGGGTTGGAGATTCCTATATGGAAGACCGTGGTCT

TCCTGCACAACGACGACGGCTCCTTCACCGGACAG

AGCGCCCTCAGAGCCGCCGTGCCGCATTGGCTAGC

CAAACGAGCCCTCATTCTCCTCATCAACCACGGGT

TGGAGCGCTTCATGATTGGCGTGCCCACCCTCACC

ATCCCCAAGAGCGTGCGTCAGGGAACCAAGCAATG

GGAGGCCGCCAAGGAAATCGTCAAGAACTTTGTTC

AAAAACCACGGCATGGTATAATACTGCCTGACGAC

TGGAAGTTTGACACGGTAGACCTGAAGTCGGCCAT

GCCCGACGCCATTCCCTACCTGACCTACCACGACG

CGGGCATCGCTAGGGCGCTTGGCATAGACTTCAAC

ACCGTTCAACTAAACATGGGGGGACAGGCGATAAA

CATCGGCGAGTTCGTAAGCCTGACCCAGCAGACCA

TCATTTCGCTCCAGCGGGAGTTCGCTAGCGCGGTC

AACCTCTACCTCATCCCCAAGCTAGTGCTTCCCAA

CTGGCCGAGCGCTACTCGCTTTCCTAGGCTCACCT

TTGAGATGGAGGAGCGCAACGACTtctcCGCCGCG

GCCAACCTTATGGGCATGCTCATCaACGCGGTTAA

GGACTCCGAAGACATTCCCACCGAGCTcaAGGCGC

TAATAGACGCTCTGCCTAGCAAGATGCGCCGGGCG

CTTGGCGTGGTGGAcgAGGTGAGGGAAGCGGTAcG

CCaACCCGCCGATTaa

SEQ ID NO: 17
GPAKLEGASVPVMSTSYDVVVDREFDELLQGKDGL

LVYHKMLSDGTVKNALNYIFGRIRSAKWYVEPAST

DPEDIAIAAFIHAQLGIDDASVGKYPFGRLFAIYE

NAYIYGMAAGEIVLTLGADGKLILDKIVPIHPFNI

DEVLYDEEGGPKALKLSGEVKGGSQFVSGLEIPIW

KTVVFLHNDDGSFTGQSALRAAVPHWLAKRALILL

INHGLERFMIGVPTLTIPKSVRQGTKQWEAAKEIV

KNFVQKPRHGIILPDDWKFDTVDLKSAMPDAIPYL

TYHDAGIARALGIDFNTVQLNMGMQAINIGEFVSL

TQQTIISLQREFASAVNLYLIPKLVLPNWPSATRF

PRLTFEMEERNDFSAAANLMGMLINAVKDSEDIPT

ELKALIDALPSKMRRALGVVDEVREAVRQPAD

SEQ ID NO: 18
ATGGGCAGCAGCCATCATcATCATCATCACAGCAG

CGGCCTGGAAGTTCTGTTCCAGGGACCAGCAAAGC

TCGAGGGCGCCTCCGTGCCGGTGATGTCCACCAGT

TACGACGTGGTGGTGGACCGGGAGTTTGACGAGCT

ACTGCAGGGCAAGGACGGCTTGCTCGTCTACCACA

AGATGCTCTCGGACGGCACGGTTAAGAACGCCCTC

AACTACATCTTCGGACGCATCCGCTCGGCGAAGTG

GTACGTAGAGCCCGCCTCTACCGACCCGGAAGACA

TCGCCATCGCCGCCTTCATCCACGCCCAGTTAGGC

ATAGACGACGCTTCGGTGGGCAAGTATCCCTTTGG

CCGCCTTTTCGCCATCTACGAAAACGCCTACATAT

ACGGCATGGCCGCCgggGAAATCGTACTAAcCCtt

GGCGCGGACGGCAAGCTCATCCTTGACaaaATCGT

CCCTAtcCACCCttTCAACATTGACGAGGTGCTTT

ACGACGAGGAAGGCGGTCCAAAGGCGCTAAAGCTA

AGCGGAGAGGTGAAgGGCGGAAGCCAGTTTGTGAG

CGGGTTGGAGATTCCTATATGGAAGACCGTGGTCT

TCCTGCACAACGACGACGGCTCCTTCACCGGACAG

AGCGCCCTCAGAGCCGCCGTGCCGCATTGGCTAGC

CAAACGAGCCCTCATTCTCCTCATCAACCACGGGT

TGGAGCGCTTCATGATTGGCGTGCCCACCCTCACC

ATCCCCAAGAGCGTGCGTCAGGGAACCAAGCAATG

-continued
GGAGGCCGCCAAGGAAATCGTCAAGAACTTTGTTC
AAAAACCACGGCATGGTATAATACTGCCTGACGAC
TGGAAGTTTGACACGGTAGACCTGAAGTCGGCCAT
GCCCGACGCCATTCCCTACCTGACCTACCACGACG
CGGGCATCGCTAGGGCGCTTGGCATAGACTTCAAC
ACCGTTCAACTAAACATGGGGATGCAGGCGATAAA
CATCGGCGAGTTCGTAAGCCTGACCCAGCAGACCA
TCATTTCGCTCCAGCGGGAGTTCGCTAGCGCGGTC
AACCTCTACCTCATCCCCAAGCTAGTGCTTCCCAA
CTGGCCGAGCGCTACTCGCTTTCCTAGGCTCACCT
TTGAGATGGAGGAGCGCAACGACtTctcCGCCGCG
GCCAACCTTATGGGCATGCTCATCaACGCGGTTAA
GGACTCCGAAGACATTCCCACCGAGCTcaAGGCGC
TAATAGACGCTCTGCCTAGCAAGATGCGCCGGGCG
CTTGGCGTGGTGGAcgAGGTGAGGGAAGCGGTAcG
CCaACCCGCCGATTaa SEQ ID NO: 19
GPAKLEGASVPVMSTSYDVVVDREFDELLQGKDGL
LVYHKMLSDGTVKNALNYIFGRIRSAKWYVEPAST
DPEDIAIAAFIHAQLGIDDASVGKYPFGRLFAIYE
NAYIYGMAAGEIVLTLGADGKLILDKIVPIHPFNI
DEVLYDEEGGPKALKLSGEVKGGSQFVSGLEIPIW
KTVVFLHNDDGSFTGQSALRAAVPHWLAKRALILL
INHGLERFMIGVPTLTIPKSVRQGTKQWEAAKEIV
KNFVQKPRHGIILPDDWKFDTVDLKSAMPDAIPYL
TYHDAGIARALGIDFNTVQLNMGVQAKNIGEFVSL
TQQTIISLQREFASAVNLYLIPKLVLPNWPSATRF
PRLTFEMEERNDFSAAANLMGMLINAVKDSEDIPT
ELKALIDALPSKMRRALGVVDEVREAVRQPAD SEQ ID NO: 20
ATGGGCAGCAGCCATCATCATCATCATCACAGCAG
CGGCCTGGAAGTTCTGTTCCAGGGACCAGCAAAGC
TCGAGGGCGCCTCCGTGCCGGTGATGTCCACCAGT
TACGACGTGGTGGTGGACCGGGAGTTTGACGAGCT
ACTGCAGGGCAAGGACGGCTTGCTCGTCTACCACA
AGATGCTCTCGGACGGCACGGTTAAGAACGCCCTC
AACTACATCTTCGGACGCATCCGCTCGGCGAAGTG
GTACGTAGAGCCCGCCTCTACCGACCCGGAAGACA
TCGCCATCGCCGCCTTCATCCACGCCCAGTTAGGC
ATAGACGACGCTTCGGTGGGCAAGTATCCCTTTGG
CCGCCTTTTCGCCATCTACGAAAACGCCTACATAT
ACGGCATGGCCGCCGGGGAAATCGTACTAACCCTT -continued
GGCGCGGACGGCAAGCTCATCCTTGACAAAATCGT
CCCTATCCACCCTTTCAACATTGACGAGGTGCTTT
ACGACGAGGAAGGCGGTCCAAAGGCGCTAAAGCTA
AGCGGAGAGGTGAAGGGCGGAAGCCAGTTTGTGAG
CGGGTTGGAGATTCCTATATGGAAGACCGTGGTCT
TCCTGCACAACGACGACGGCTCCTTCACCGGACAG
AGCGCCCTCAGAGCCGCCGTGCCGCATTGGCTAGC
CAAACGAGCCCTCATTCTCCTCATCAACCACGGGT
TGGAGCGCTTCATGATTGGCGTGCCCACCCTCACC
ATCCCCAAGAGCGTGCGTCAGGGAACCAAGCAATG
GGAGGCCGCCAAGGAAATCGTCAAGAACTTTGTTC
AAAAACCACGGCATGGTATAATACTGCCTGACGAC
TGGAAGTTTGACACGGTAGACCTGAAGTCGGCCAT
GCCCGACGCCATTCCCTACCTGACCTACCACGACG
CGGGCATCGCTAGGGCGCTTGGCATAGACTTCAAC
ACCGTTCAACTAAACATGGGGGTACAGGCGAAGAA
CATCGGCGAGTTCGTAAGCCTGACCCAGCAGACCA
TCATTTCGCTCCAGCGGGAGTTCGCTAGCGCGGTC
AACCTCTACCTCATCCCCAAGCTAGTGCTTCCCAA
CTGGCCGAGCGCTACTCGCTTTCCTAGGCTCACCT
TTGAGATGGAGGAGCGCAACGACTTCTCCGCCGCG
GCCAACCTTATGGGCATGCTCATCAACGCGGTTAA
GGACTCCGAAGACATTCCCACCGAGCTCAAGGCGC
TAATAGACGCTCTGCCTAGCAAGATGCGCCGGGCG
CTTGGCGTGGTGGACGAGGTGAGGGAAGCGGTACG
CCAACCCGCCGATTAA SEQ ID NO: 21
GPAKLEGASVPVMSTSYDVVVDREFDECLQGKDGL
LVYHKMLSDGTVKNALNYIFGRIRSAKWYVEPAST
DPEDIAIAAFIHAQLGIDDASVGKYPFGRLFAIYE
NAYIYGMAAGEIVLTLGADGKLILDKIVPIHPFNI
DEVLYDEEGGPKALKLSGEVKGGSQFVSGLEIPIW
KTVVFLHNDDGSFTGQSALRAAVPHWLAKRALILL
INHGLERFMIGVPTLTIPKSVRQGTKQWEAAKEIV
KNFVQKPRHGIILPDDWKFDTVDLKSAMPDAIPYL
TYHDAGIARALGIDFNTVQLNMGGQAGNIGEFVSL
TQQTIISLQREFASAVNLYLIPKLVLPNWPSATRF
PRLTFEMEERNDFSAAANLMGMLINAVKDSEDIPT
ELKALIDALPSKMRRALGVVDEVREAVRQPAD SEQ ID NO: 22
ATGGGCAGCAGCCATCATcATCATCATCACAGCAG
CGGCCTGGAAGTTCTGTTCCAGGGACCAGCAAAGC
TCGAGGGCGCCTCCGTGCCGGTGATGTCCACCAGT
TACGACGTGGTGGTGGACCGGGAGTTTGACGAGTG
TCTGCAGGGCAAGGACGGCTTGCTCGTCTACCACA
AGATGCTCTCGGACGGCACGGTTAAGAACGCCCTC
AACTACATCTTCGGACGCATCCGCTCGGCGAAGTG
GTACGTAGAGCCCGCCTCTACCGACCCGGAAGACA
TCGCCATCGCCGCCTTCATCCACGCCCAGTTAGGC
ATAGACGACGCTTCGGTGGGCAAGTATCCCTTTGG
CCGCCTTTTCGCCATCTACGAAAACGCCTACATAT
ACGGCATGGCCGCCgggGAAATCGTACTAAcCCtt
GGCGCGGACGGCAAGCTCATCCTTGACaaaATCGT
CCCTAtcCACCCttTCAACATTGACGAGGTGCTTT
ACGACGAGGAAGGCGGTCCAAAGGCGCTAAAGCTA
AGCGGAGAGGTGAAgGGCGGAAGCCAGTTTGTGAG
CGGGTTGGAGATTCCTATATGGAAGACCGTGGTCT
TCCTGCACAACGACGACGGCTCCTTCACCGGACAG
AGCGCCCTCAGAGCCGCCGTGCCGCATTGGCTAGC
CAAACGAGCCCTCATTCTCCTCATCAACCACGGGT
TGGAGCGCTTCATGATTGGCGTGCCCACCCTCACC
ATCCCCAAGAGCGTGCGTCAGGGAACCAAGCAATG
GGAGGCCGCCAAGGAAATCGTCAAGAACTTTGTTC
AAAAACCACGGCATGGTATAATACTGCCTGACGAC
TGGAAGTTTGACACGGTAGACCTGAAGTCGGCCAT
GCCCGACGCCATTCCCTACCTGACCTACCACGACG
CGGGCATCGCTAGGGCGCTTGGCATAGACTTCAAC
ACCGTTCAACTAAACATGGGGGGACAGGCGGGAAA
CATCGGCGAGTTCGTAAGCCTGACCCAGCAGACCA
TCATTTCGCTCCAGCGGGAGTTCGCTAGCGCGGTC
AACCTCTACCTCATCCCCAAGCTAGTGCTTCCCAA
CTGGCCGAGCGCTACTCGCTTTCCTAGGCTCACCT
TTGAGATGGAGGAGCGCAACGACTtctcCGCCGCG
GCCAACCTTATGGGCATGCTCATCaACGCGGTTAA
GGACTCCGAAGACATTCCCACCGAGCTcaAGGCGC
TAATAGACGCTCTGCCTAGCAAGATGCGCCGGGCG
CTTGGCGTGGTGGacgAGGTGAGGGAAGCGGTAcG
CCaACCCGCCGATTaa SEQ ID NO: 23
GPAKLEGASVPVMSTSYDVVVDREFDELLQGKDGL
LVYHKMLSDGTVKNALNYIFGRIRSAKWYVEPAST
DPEDIAIAAFIHAQLGIDDASVGKYPFGRLFAIYE
NAYIYGMAAGEIVLTLGADGKLILDKIVPIHPFNI
DEVLYDEEGGPKALKLSGEVKGGSQFVSGLEIPIW
KTVVFLHNDDGSFTGQSALRAAVPHWLAKRALILL
INHGLERFMIGVPTLTIPKSVRQGTKQWEAAKEIV
KNFVQKPRHGIILPDDWKFDTVDLKSAMPDAIPYL
TYHDAGIARALGIDFNTVQLNMGGGGNIGEFVSLT
QQTIISLQREFASAVNLYLIPKLVLPNWPSATRFP
RLTFEMEERNDFSAAANLMGMLINAVKDSEDIPTE
LKALIDALPSKMRRALGVVDEVREAVRQPAD SEQ ID NO: 24
ATGGGCAGCAGCCATCATCATCATCATCACAGCAG
CGGCCTGGAAGTTCTGTTCCAGGGACCAGCAAAGC
TCGAGGGCGCCTCCGTGCCGGTGATGTCCACCAGT
TACGACGTGGTGGTGGACCGGGAGTTTGACGAGCT
ACTGCAGGGCAAGGACGGCTTGCTCGTCTACCACA
AGATGCTCTCGGACGGCACGGTTAAGAACGCCCTC
AACTACATCTTCGGACGCATCCGCTCGGCGAAGTG
GTACGTAGAGCCCGCCTCTACCGACCCGGAAGACA
TCGCCATCGCCGCCTTCATCCACGCCCAGTTAGGC
ATAGACGACGCTTCGGTGGGCAAGTATCCCTTTGG
CCGCCTTTTCGCCATCTACGAAAACGCCTACATAT
ACGGCATGGCCGCCGGGGAAATCGTACTAACCCTT
GGCGCGGACGGCAAGCTCATCCTTGACAAAATCGT
CCCTATCCACCCTTTCAACATTGACGAGGTGCTTT
ACGACGAGGAAGGCGGTCCAAAGGCGCTAAAGCTA
AGCGGAGAGGTGAAGGGCGGAAGCCAGTTTGTGAG
CGGGTTGGAGATTCCTATATGGAAGACCGTGGTCT
TCCTGCACAACGACGACGGCTCCTTCACCGGACAG
AGCGCCCTCAGAGCCGCCGTGCCGCATTGGCTAGC
CAAACGAGCCCTCATTCTCCTCATCAACCACGGGT
TGGAGCGCTTCATGATTGGCGTGCCCACCCTCACC
ATCCCCAAGAGCGTGCGTCAGGGAACCAAGCAATG
GGAGGCCGCCAAGGAAATCGTCAAGAACTTTGTTC
AAAAACCACGGCATGGTATAATACTGCCTGACGAC
TGGAAGTTTGACACGGTAGACCTGAAGTCGGCCAT
GCCCGACGCCATTCCCTACCTGACCTACCACGACG
CGGGCATCGCTAGGGCGCTTGGCATAGACTTCAAC
ACCGTTCAACTAAACATGGGGGGAGGCGGTAACAT
CGGCGAGTTCGTAAGCCTGACCCAGCAGACCATCA
TTTCGCTCCAGCGGGAGTTCGCTAGCGCGGTCAAC -continued

CTCTACCTCATCCCCAAGCTAGTGCTTCCCAACTG

GCCGAGCGCTACTCGCTTTCCTAGGCTCACCTTTG

AGATGGAGGAGCGCAACGACTTCTCCGCCGCGGCC

AACCTTATGGGCATGCTCATCAACGCGGTTAAGGA

CTCCGAAGACATTCCCACCGAGCTCAAGGCGCTAA

TAGACGCTCTGCCTAGCAAGATGCGCCGGGCGCTT

GGCGTGGTGGACGAGGTGAGGGAAGCGGTACGCCA

ACCCGCCGATTAA

SEQ ID NO: 25

GPAKLEGASVPVMSTSYDVVVDREFDECLQGKDGL
LVYHKMLSDGTVKNALNYIFGRIRSAKWYVEPAST
DPEDIAIAAFIHAQLGIDDASVGKYPFGRLFAIYE
NAYIYGMAAGEIVLTLGADGKLILDKIVPIHPFNI
DEVLYDEEGGPKALKLSGEVKGGSQFVSGLEIPIW
KTVVFLHNDDGSFTGQSALRAAVPHWLAKRALILL
INHGLERFMIGVPTLTIPKSVRQGTKQWEAAKEIV
KNFVQKPRHGIILPDDWKFDTVDLKSAMPDAIPYL
TYHDAGIARALGIDFNTVQLGIGEFVSLTQQTIIS
LQREFASAVNLYLIPKLVLPNWPSATRFPRLTFEM
EERNDFSAAANLMGMLINAVKDSEDIPTELKALID
ALPSKMRRALGVVDEVREAVRQPAD

SEQ ID NO: 26 cATCATCACAGCAGCGGCCTGGAAGTTCTGTTCCA

GGGACCAGCAAAGCTCGAGGGCGCCTCCGTGCCGG

TGATGTCCACCAGTTACGACGTGGTGGTGGACCGG

GAGTTTGACGAGTGTCTGCAGGGCAAGGACGGCTT

GCTCGTCTACCACAAGATGCTCTCGGACGGCACGG

TTAAGAACGCCCTCAACTACATCTTCGGACGCATC

CGCTCGGCGAAGTGGTACGTAGAGCCCGCCTCTAC

CGACCCGGAAGACATCGCCATCGCCGCCTTCATCC

ACGCCCAGTTAGGCATAGACGACGCTTCGGTGGGC

AAGTATCCCTTTGGCCGCCTTTTCGCCATCTACGA

AAACGCCTACATATACGGCATGGCCGCCGGGGAAA

TCGTACTAACCCTTGGCGCGGACGGCAAGCTCATC

CTTGACAAAATCGTCCCTATCCACCCTTTCAACAT

TGACGAGGTGCTTTACGACGAGGAAGGCGGTCCAA

AGGCGCTAAAGCTAAGCGGAGAGGTGAAGGGCGGA

AGCCAGTTTGTGAGCGGGTTGGAGATTCCTATATG

GAAGACCGTGGTCTTCCTGCACAACGACGACGGCT

CCTTCACCGGACAGAGCGCCCTCAGAGCCGCCGTG

CCGCATTGGCTAGCCAAACGAGCCCTCATTCTCCT

-continued

CATCAACCACGGGTTGGAGCGCTTCATGATTGGCG

TGCCCACCCTCACCATCCCCAAGAGCGTGCGTCAG

GGAACCAAGCAATGGGAGGCCGCCAAGGAAATCGT

CAAGAACTTTGTTCAAAAACCACGGCATGGTATAA

TACTGCCTGACGACTGGAAGTTTGACACGGTAGAC

CTGAAGTCGGCCATGCCCGACGCCATTCCCTACCT

GACCTACCACGACGCGGGCATCGCTAGGGCGCTTG

GCATAGACTTCAACACCGTTCAACTAGGTATCGGC

GAGTTCGTAAGCCTGACCCAGCAGACCATCATTTC

GCTCCAGCGGGAGTTCGCTAGCGCGGTCAACCTCT

ACCTCATCCCCAAGCTAGTGCTTCCCAACTGGCCG

AGCGCTACTCGCTTTCCTAGGCTCACCTTTGAGAT

GGAGGAGCGCAACGACTTCTCCGCCGCGGCCAACC

TTATGGGCATGCTCATCAACGCGGTTAAGGACTCC

GAAGACATTCCCACCGAGCTCAAGGCGCTAATAGA

CGCTCTGCCTAGCAAGATGCGCCGGGCGCTTGGCG

TGGTGGACGAGGTGAGGGAAGCGGTACGCCAACCC

GCCGantaa

SEQ ID NO: 27

GPAKLEGASVPVMSTSYDVVVDREFDECLQGKDGL
LVYHKMLSDGTVKNALNYIFGRIRSAKWYVEPAST
DPEDIAIAAFIHAQLGIDDASVGKYPFGRLFAIYE
NAYIYGMAAGEIVLTLGADGKLILDKIVPIHPFNI
DEVLYDEEGGPKALKLSGEVKGGSQFVSGLEIPIW
KTVVFLHNDDGSFTGQSALRAAVPHWLAKRALILL
INHGLERFMIGVPTLTIPKSVRQGTKQWEAAKEIV
KNFVQKPRHGIILPNDWKFNTVNLKSAMPNAIPYL
TYHDAGIARALGIDFNTVQLNMGVQAINIGEFVSL
TQQTIISLQREFASAANLYLIPKLVLPNWPSATRF
PRLTFEMEERNDFSAAANLMGMLINAVKDSEDIPT
ELKALIDALPSKMRRALGVVDEVREAVRQPAD

SEQ ID NO: 28

ATGGGCAGCAGCCATCATCATCATCATCACAGCAG

CGGCCTGGAAGTTCTGTTCCAGGGACCAGCAAAGC

TCGAGGGCGCCTCCGTGCCGGTGATGTCCACCAGT

TACGACGTGGTGGTGGACCGGGAGTTTGACGAGTG

TCTGCAGGGCAAGGACGGCTTGCTCGTCTACCACA

AGATGCTCTCGGACGGCACGGTTAAGAACGCCCTC

AACTACATCTTCGGACGCATCCGCTCGGCGAAGTG

GTACGTAGAGCCCGCCTCTACCGACCCGGAAGACA

TCGCCATCGCCGCCTTCATCCACGCCCAGTTAGGC

ATAGACGACGCTTCGGTGGGCAAGTATCCCTTTGG

-continued

```
CCGCCTTTTCGCCATCTACGAAAACGCCTACATAT
ACGGCATGGCCGCCGGGGAAATCGTACTAACCCTT
GGCGCGGACGGCAAGCTCATCCTTGACAAAATCGT
CCCTATCCACCCTTTCAACATTGACGAGGTGCTTT
ACGACGAGGAAGGCGGTCCAAAGGCGCTAAAGCTA
AGCGGAGAGGTGAAGGGCGGAAGCCAGTTTGTGAG
CGGGTTGGAGATTCCTATATGGAAGACCGTGGTCT
TCCTGCACAACGACGACGGCTCCTTCACCGGACAG
AGCGCCCTCAGAGCCGCCGTGCCGCATTGGCTAGC
CAAACGAGCCCTCATTCTCCTCATCAACCACGGGT
TGGAGCGCTTCATGATTGGCGTGCCCACCCTCACC
ATCCCCAAGAGCGTGCGTCAGGGAACCAAGCAATG
GGAGGCCGCCAAGGAAATCGTCAAGAACTTTGTTC
AAAAACCACGGCATGGTATAATACTGCCTAACGAC
TGGAAGTTTAACACGGTAAACCTGAAGTCGGCCAT
GCCCAACGCCATTCCCTACCTGACCTACCACGACG
CGGGCATCGCTAGGGCGCTTGGCATAGACTTCAAC
ACCGTTCAACTAAACATGGGGGTACAGGCGATAAA
CATCGGCGAGTTCGTAAGCCTGACCCAGCAGACCA
TCATTTCGCTCCAGCGGGAGTTCGCTAGCGCGGCC
AACCTCTACCTCATCCCCAAGCTAGTGCTTCCCAA
CTGGCCGAGCGCTACTCGCTTTCCTAGGCTCACCT
TTGAGATGGAGGAGCGCAACGACTTCTCCGCCGCG
GCCAACCTTATGGGCATGCTCATCAACGCGGTTAA
GGACTCCGAAGACATTCCCACCGAGCTCAAGGCGC
TAATAGACGCTCTGCCTAGCAAGATGCGCCGGGCG
CTTGGCGTGGTGGACGAGGTGAGGGAAGCGGTACG
CCAACCCGCCGATTAA
```

SEQ ID NO: 29
```
GPAKLEGASVPVMSTSYDVVVDREFDEGTPGSRGL
LQGKDGLLVYHKMLSDGTVKNALNYIFGRIRSAKW
YVEPASTDPEDIAIAAFIHAQLGIDDASVGKYPFG
RLFAIYENAYIYGMAAGEIVLTLGADGKLILDKIV
PIHPFNIDEVLYDEEGGPKALKLSGEVKGGSQFVS
GLEIPIWKTVVFLHNDDGSFTGQSALRAAVPHWLA
KRALILLINHGLERFMIGVPTLTIPKSVRQGTKQW
EAAKEIVKNFVQKPRHGIILPNDWKFNTVNLKSAM
PNAIPYLTYHDAGIARALGIDFNTVQLNMGVQAIN
IGEFVSLTQQTIISLQREFASAVNLYLIPKLVLPN
WPSATRFPRLTFEMEERNDFSAAANLMGMLINAVK
DSEDIPTELKALIDALPSKMRRALGVVDEVREAVR
QPAD
```

SEQ ID NO: 30
```
ATGGGCAGCAGCCATCATCATCATCATCACAGCAG
CGGCCTGGAAGTTCTGTTCCAGGGACCAGCAAAGC
TCGAGGGCGCCTCCGTGCCGGTGATGTCCACCAGT
TACGACGTGGTGGTGGACCGGGAGTTTGACGAGGG
TACGCCAGGTTCTCGCGCCTACTGCAGGGCAAGG
ACGGCTTGCTCGTCTACCACAAGATGCTCTCGGAC
GGCACGGTTAAGAACGCCCTCAACTACATCTTCGG
ACGCATCCGCTCGGCGAAGTGGTACGTAGAGCCCG
CCTCTACCGACCCGGAAGACATCGCCATCGCCGCC
TTCATCCACGCCCAGTTAGGCATAGACGACGCTTC
GGTGGGCAAGTATCCCTTTGGCCGCCTTTTCGCCA
TCTACGAAAACGCCTACATATACGGCATGGCCGCC
GGGGAAATCGTACTAACCCTTGGCGCGGACGGCAA
GCTCATCCTTGACAAAATCGTCCCTATCCACCCTT
TCAACATTGACGAGGTGCTTTACGACGAGGAAGGC
GGTCCAAAGGCGCTAAAGCTAAGCGGAGAGGTGAA
GGGCGGAAGCCAGTTTGTGAGCGGGTTGGAGATTC
CTATATGGAAGACCGTGGTCTTCCTGCACAACGAC
GACGGCTCCTTCACCGGACAGAGCGCCCTCAGAGC
CGCCGTGCCGCATTGGCTAGCCAAACGAGCCCTCA
TTCTCCTCATCAACCACGGGTTGGAGCGCTTCATG
ATTGGCGTGCCCACCCTCACCATCCCCAAGAGCGT
GCGTCAGGGAACCAAGCAATGGGAGGCCGCCAAGG
AAATCGTCAAGAACTTTGTTCAAAAACCACGGCAT
GGTATAATACTGCCTAACGACTGGAAGTTTAACAC
GGTAAACCTGAAGTCGGCCATGCCCAACGCCATTC
CCTACCTGACCTACCACGACGCGGGCATCGCTAGG
GCGCTTGGCATAGACTTCAACACCGTTCAACTAAA
CATGGGGGTACAGGCGATAAACATCGGCGAGTTCG
TAAGCCTGACCCAGCAGACCATCATTTCGCTCCAG
CGGGAGTTCGCTAGCGCGGTCAACCTCTACCTCAT
CCCCAAGCTAGTGCTTCCCAACTGGCCGAGCGCTA
CTCGCTTTCCTAGGCTCACCTTTGAGATGGAGGAG
CGCAACGACTTCTCCGCCGCGGCCAACCTTATGGG
CATGCTCATCAACGCGGTTAAGGACTCCGAAGACA
TTCCCACCGAGCTCAAGGCGCTAATAGACGCTCTG
```

```
                                        -continued
CCTAGCAAGATGCGCCGGGCGCTTGGCGTGGTGGA
CGAGGTGAGGGAAGCGGTACGCCAACCCGCCGATT
AA
```

SEQ ID NO: 31
```
GPAKLEGASVPVMSTSYDVVVDREFDEGRKLPDAG
LLQGKDGLLVYHKMLSDGTVKNALNYIFGRIRSAK
WYVEPASTDPEDIAIAAFIHAQLGIDDASVGKYPF
GRLFAIYENAYIYGMAAGEIVLTLGADGKLILDKI
VPIHPFNIDEVLYDEEGGPKALKLSGEVKGGSQFV
SGLEIPIWKTVVFLHNDDGSFTGQSALRAAVPHWL
AKRALILLINHGLERFMIGVPTLTIPKSVRQGTKQ
WEAAKEIVKNFVQKPRHGIILPNDWKFNTVNLKSA
MPNAIPYLTYHDAGIARALGIDFNTVQLNMGVQAI
NIGEFVSLTQQTIISLQREFASAVNLYLIPKLVLP
NWPSATRFPRLTFEMEERNDFSAAANLMGMLINAV
KDSEDIPTELKALIDALPSKMRRALGVVDEVREAV
RQPAD
```

SEQ ID NO: 32
```
ATGGGCAGCAGCCatCaTCAtcatCATCACAGCAG
CGGCCTGGAAGTTCTGTTCCAGGGACCAGCAAAGC
TCGAGGGCGCCTCCGTGCCGGTGATGTCCACCAGT
TACGACGTGGTGGTGGACCGGGAGTTTGACGAGGG
TCGTAAACTGCCGGATGCAGGCCTACTGCAGGGCA
AGGACGGCTTGCTCGTCTACCACAAGATGCTCTCG
GACGGCACGGTTAAGAACGCCCTCAACTACATCTT
CGGACGCATCCGCTCGGCGAAGTGGTACGTAGAGC
CCGCCTCTACCGACCCGGAAGACATCGCCATCGCC
GCCTTCATCCACGCCCAGTTAGGCATAGACGACGC
TTCGGTGGGCAAGTATCCCTTTGGCCGCCTTTTCG
CCATCTACGAAAACGCCTACATATACGGCATGGCC
GCCGGGGAAATCGTACTAACCCTTGGCGCGGACGG
CAAGCTCATCCTTGACAAAATCGTCCCTATCCACC
CTTTCAACATTGACGAGGTGCTTTACGACGAGGAA
GGCGGTCCAAAGGCGCTAAAGCTAAGCGGAGAGGT
GAAGGGCGGAAGCCAGTTTGTGAGCGGGTTGGAGA
TTCCTATATGGAAGACCGTGGTCTTCCTGCACAAC
GACGACGGCTCCTTCACCGGACAGAGCGCCCTCAG
AGCCGCCGTGCCGCATTGGCTAGCCAAACGAGCCC
TCATTCTCCTCATCAACCACGGGTTGGAGCGCTTC
ATGATTGGCGTGCCCACCCTCACCATCCCCAAGAG
CGTGCGTCAGGGAACCAAGCAATGGGAGGCCGCCA
AGGAAATCGTCAAGAACTTTGTTCAAAAACCACGG
```

```
                                        -continued
CATGGTATAATACTGCCTAACGACTGGAAGTTTAA
CACGGTAAACCTGAAGTCGGCCATGCCCAACGCCA
TTCCCTACCTGACCTACCACGACGCGGGCATCGCT
AGGGCGCTTGGCATAGACTTCAACACCGTTCAACT
AAACATGGGGGTACAGGCGATAAACATCGGCGAGT
TCGTAAGCCTGACCCAGCAGACCATCATTTCGCTC
CAGCGGGAGTTCGCTAGCGCGGTCAACCTCTACCT
CATCCCCAAGCTAGTGCTTCCCAACTGGCCGAGCG
CTACTCGCTTTCCTAGGCTCACCTTTGAGATGGAG
GAGCGCAACGACTTCTCCGCCGCGGCCAACCTTAT
GGGCATGCTCATCAACGCGGTTAAGGACTCCGAAG
ACATTCCCACCGAGCTCAAGGCGCTAATAGACGCT
CTGCCTAGCAAGATGCGCCGGGCGCTTGGCGTGGT
GGACGAGGTGAGGGAAGCGGTACGCCAACCCGCCG
AtTAA
```

SEQ ID NO: 33
```
GPASSKKSGSYSGSKGSKLEGASVPVMSTSYDVVV
DREFDECLQGKDGLLVYHKMLSDGTVKNALNYIFG
RIRSAKWYVEPASTDPEDIAIAAFIHAQLGIDDAS
VGKYPFGRLFAIYENAYIYGMAAGEIVLTLGADGK
LILDKIVPIHPFNIDEVLYDEEGGPKALKLSGEVK
GGSQFVSGLEIPIWKTVVFLHNDDGSFTGQSALRA
AVPHWLAKRALILLINHGLERFMIGVPTLTIPKSV
RQGTKQWEAAKEIVKNFVQKPRHGIILPNDWKFNT
VNLKSAMPNAIPYLTYHDAGIARALGIDFNTVQLN
MGVQAINIGEFVSLTQQTIISLQREFASAANLYLI
PKLVLPNWPSATRFPRLTFEMEERNDFSAAANLMG
MLINAVKDSEDIPTELKALIDALPSKMRRALGVVD
EVREAVRQPAD
```

SEQ ID NO: 34
```
ATGGGCAGCAGCCATCATCATCATCATCACAGCAG
CGGCCTGGAAGTTCTGTTCCAGGGACCAGCAAGCA
GTAAGAAAAGTGGAAGCTATAGCGGCAGCAAAGGC
AGCAAGCTCGAGGGCGCCTCCGTGCCGGTGATGTC
CACCAGTTACGACGTGGTGGTGGACCGGGAGTTTG
ACGAGTGTCTGCAGGGCAAGGACGGCTTGCTCGTC
TACCACAAGATGCTCTCGGACGGCACGGTTAAGAA
CGCCCTCAACTACATCTTCGGACGCATCCGCTCGG
CGAAGTGGTACGTAGAGCCCGCCTCTACCGACCCG
GAAGACATCGCCATCGCCGCCTTCATCCACGCCCA
GTTAGGCATAGACGACGCTTCGGTGGGCAAGTATC
```

-continued
CCTTTGGCCGCCTTTTCGCCATCTACGAAAACGCC
TACATATACGGCATGGCCGCCGGGGAAATCGTACT
AACCCTTGGCGCGGACGGCAAGCTCATCCTTGACA
AAATCGTCCCTATCCACCCTTTCAACATTGACGAG
GTGCTTTACGACGAGGAAGGCGGTCCAAAGGCGCT
AAAGCTAAGCGGAGAGGTGAAGGGCGGAAGCCAGT
TTGTGAGCGGGTTGGAGATTCCTATATGGAAGACC
GTGGTCTTCCTGCACAACGACGACGGCTCCTTCAC
CGGACAGAGCGCCCTCAGAGCCGCCGTGCCGCATT
GGCTAGCCAAACGAGCCCTCATTCTCCTCATCAAC
CACGGGTTGGAGCGCTTCATGATTGGCGTGCCCAC
CCTCACCATCCCCAAGAGCGTGCGTCAGGGAACCA
AGCAATGGAGGCCGCCAAGGAAATCGTCAAGAAC
TTTGTTCAAAAACCACGGCATGGTATAATACTGCC
TAACGACTGGAAGTTTAACACGGTAAACCTGAAGT
CGGCCATGCCCAACGCCATTCCCTACCTGACCTAC
CACGACGCGGGCATCGCTAGGGCGCTTGGCATAGA
CTTCAACACCGTTCAACTAAACATGGGGGTACAGG
CGATAAACATCGGCGAGTTCGTAAGCCTGACCCAG
CAGACCATCATTTCGCTCCAGCGGGAGTTCGCTAG
CGCGGCCAACCTCTACCTCATCCCCAAGCTAGTGC
TTCCCAACTGGCCGAGCGCTACTCGCTTTCCTAGG
CTCACCTTTGAGATGGAGGAGCGCAACGACTTCTC
CGCCGCGGCCAACCTTATGGGCATGCTCATCAACG
CGGTTAAGGACTCCGAAGACATTCCCACCGAGCTC
AAGGCGCTAATAGACGCTCTGCCTAGCAAGATGCG
CCGGGCGCTTGGCGTGGTGGACGAGGTGAGGGAAG
CGGTACGCCAACCCGCCGATTAA SEQ ID NO: 35
GPAKLEGASVPVMSTSYDVVVDREFDEGYRPGFYF
RLLQGKDGLLVYHKMLSDGTVKNALNYIFGRIRSA
KWYVEPASTDPEDIAIAAFIHAQLGIDDASVGKYP
FGRLFAIYENAYIYGMAAGEIVLTLGADGKLILDK
IVPIHPFNIDEVLYDEEGGPKALKLSGEVKGSQF
VSGLEIPIWKTVVFLHNDDGSFTGQSALRAAVPHW
LAKRALILLINHGLERFMIGVPTLTIPKSVRQGTK
QWEAAKEIVKNFVQKPRHGIILPNDWKFNTVNLKS
AMPNAIPYLTYHDAGIARALGIDFNTVQLNMGVQA
INIGEFVSLTQQTIISLQREFASAVNLYLIPKLVL -continued
PNWPSATRFPRLTFEMEERNDFSAAANLMGMLINA
VKDSEDIPTELKALIDALPSKMRRALGVVDEVREA
VRQPAD SEQ ID NO: 36
ATGGGCAGCAGCCATCATCATCATCATCACAGCAG
CGGCCTGGAAGTTCTGTTCCAGGGACCAGCAAAGC
TCGAGGGCGCCTCCGTGCCGGTGATGTCCACCAGT
TACGACGTGGTGGTGGACCGGGAGTTTGACGAGGG
ATATCGCCCGGGCTTTTATTTTCGCCTACTGCAGG
GCAAGGACGGCTTGCTCGTCTACCACAAGATGCTC
TCGGACGGCACGGTTAAGAACGCCCTCAACTACAT
CTTCGGACGCATCCGCTCGGCGAAGTGGTACGTAG
AGCCCGCCTCTACCGACCCGGAAGACATCGCCATC
GCCGCCTTCATCCACGCCCAGTTAGGCATAGACGA
CGCTTCGGTGGGCAAGTATCCCTTTGGCCGCCTTT
TCGCCATCTACGAAAACGCCTACATATACGGCATG
GCCGCCGGGGAAATCGTACTAACCCTTGGCGCGGA
CGGCAAGCTCATCCTTGACAAAATCGTCCCTATCC
ACCCTTTCAACATTGACGAGGTGCTTTACGACGAG
GAAGGCGGTCCAAAGGCGCTAAAGCTAAGCGGAGA
GGTGAAGGGCGGAAGCCAGTTTGTGAGCGGGTTGG
AGATTCCTATATGGAAGACCGTGGTCTTCCTGCAC
AACGACGACGGCTCCTTCACCGGACAGAGCGCCCT
CAGAGCCGCCGTGCCGCATTGGCTAGCCAAACGAG
CCCTCATTCTCCTCATCAACCACGGGTTGGAGCGC
TTCATGATTGGCGTGCCCACCCTCACCATCCCCAA
GAGCGTGCGTCAGGGAACCAAGCAATGGGAGGCCG
CCAAGGAAATCGTCAAGAACTTTGTTCAAAAACCA
CGGCATGGTATAATACTGCCTAACGACTGGAAGTT
TAACACGGTAAACCTGAAGTCGGCCATGCCCAACG
CCATTCCCTACCTGACCTACCACGACGCGGGCATC
GCTAGGGCGCTTGGCATAGACTTCAACACCGTTCA
ACTAAACATGGGGGTACAGGCGATAAACATCGGCG
AGTTCGTAAGCCTGACCCAGCAGACCATCATTTCG
CTCCAGCGGGAGTTCGCTAGCGCGGTCAACCTCTA
CCTCATCCCCAAGCTAGTGCTTCCCAACTGGCCGA
GCGCTACTCGCTTTCCTAGGCTCACCTTTGAGATG
GAGGAGCGCAACGACTTCTCCGCCGCGGCCAACCT
TATGGGCATGCTCATCAACGCGGTTAAGGACTCCG
AAGACATTCCCACCGAGCTCAAGGCGCTAATAGAC

```
                              SEQ ID NO: 37
MAKRGRKPKELVPGPGSIDPSDVPKLEGASVPVMS
TSYDVVVDREFDELLQGKDGLLVYHKMLSDGTVKN
ALNYIFGRIRSAKWYVEPASTDPEDIAIAAFIHAQ
LGIDDASVGKYPFGRLFAIYENAYIYGMAAGEIVL
TLGADGKLILDKIVPIHPFNIDEVYDEEGGPKALK
LSGEVKGGSQFVSGLEIPIWKTVVFLHNDDGSFTG
QSALRAAVPHWLAKRALILLINHGLERFMIGVPTL
TIPKSVRQGTKQWEAAKEIVKNFVQKPRHGIILPD
DWKFDTVDLKSAMPDAIPYLTYHDAGIARALGIDF
NTVQLNMGVQAINIGEFVSLTQQTIISLQREFASA
VNLYLIPKLVLPNWPSATRFPRLTFEMEERNDFSA
AANLMGMLINAVKCSEDIPTELKALIDALPSKMRR
ALGVVDEVREAVRQPADLEHHHHHH

SEQ ID NO: 38
ATGGCTAAGCGAGGACGTAAACCCAAAGAGCTGGT
CCCCGGACCTGGCTCCATTGACCCATCTGACGTTC
CCAAGCTCGAGGGCGCCTCCGTGCCGGTGATGTCC
ACCAGTTACGACGTGGTGGTGGACCGGGAGTTTGA
CGAGCTACTGCAGGGCAAGGACGGCTTGCTCGTCT
ACCACAAGATGCTCTCGGACGGCACGGTTAAGAAC
GCCCTCAACTACATCTTCGGACGCATCCGCTCGGC
GAAGTGGTACGTAGAGCCCGCCTCTACCGACCCGG
AAGACATCGCCATCGCCGCCttCATCcacgcCCAG
TTAGGCATAGACGACGCTTCgGtgGGCAAGTATcC
CtttgGCCGcCTTTTcgCCATctACGAAAACGCCT
ACATATACGGCATGGCCGCCggGGAAATCGTACTA
AccCTTGGCGCGGACGGCAAGCTCATCCTTGACAA
AATCGTcCCTATCCACCCTTTCAACATTGACGAGG
TGCnTTACGACGAGGAAGGCGGTCCAAAGGCGCTA
AAGCTAAGCGGAGAGGTGAAGGGCGGAAGCCAGTT
TGTGAGCGGGTTGGAGATTCCTATATGGAAGACCG
TGGTCTTCCTGCACAACGACGACGGCTCCTTCACC
GGACAGAGCGCCCTCAGAGCCGCCGTGCCGCATTG
GCTAGCCAAACGAGCCCTCATTCTCCTCATCAACC
ACGGGTTGGAGCGCTTCATGATTGGCGTGCCCACC
CTCACCATCCCCAAGAGCGTGCGTCAGGGAACCAA
GCAATGGGAGGCCGCCAAGGAAATCGTCAAGAACT TTGTTCAAAAACCACGGCATGGTATAATACTGCCT
GACGACTGGAAGTTTGACACGGTAGACCTGAAGTC
GGCCATGCCCGACGCCATTCCCTACCTGACCTACC
ACGACGCGGGCATCGCTAGGGCGCTTGGCATAGAC
TTCAACACCGTTCAACTAAACATGGGGGTACAGGC
GATAAACATCGGCGAGTTCGTAAGCCTGACCCAGC
AGACCATCATTTCGCTCCAGCGGGAGTTCGCTAGC
GCGGTCAACCTCTACCTCATCCCCAAGCTAGTGCT
TCCCAACTGGCCGAGCGCTACTCGCTTTCCTAGGC
TCACCTTTGAGATGGAGGAGCGCAACGACTTCTCC
GCCGCGGCCAACCTTATGGGCATGCTCATCAACGC
GGTTAAGTGCTCCGAAGACATTCCCACCGAGCTCA
AGGCGCTAATAGACGCTCTGCCTAGCAAGATGCGC
CGGGCGCTTGGCGTGGTGGACGAGGTGAGGGAAGC
GGTACGCCAACCCGCCGATCTCGAGCACCACCACC
ACCACCACTGA SEQ ID NO: 39
MGSSHHHHHHSSGLEVLFQGPAKLEGASVPVMSTS
YDVVVDREFDELLQGKDGLLVYHKMLSDGTVKNAL
NYIFGRIRSAKWYVEPASTDPEDIAIAAFIHAQLG
IDDASVGKYPFGRLFAIYENAYIYGMAAGEIVLTL
GADGKLILDKIVPIHPFNIDEVLYDEEGGPKALKL
SGEVKGGSQFVSGLEIPIWKTVVFLHNDDGSFTGQ
SALRAAVPHWLAKRALILLINHGLERFMIGVPTLT
IPKSVRQGTKQWEAAKEIVKNFVQKPRHGIILPDD
WKFDTVDLKSAMPDAIPYLTYHDAGIARALGIDFN
TVQLNMGVQAINIGEFVSLTQQTIISLQREFASAV
NLYLIPKLVLPNWPSATRFPRLTFEMEERNDFSAA
ANLMGMLINAVKDSEDIPTELKALIDALPSKMRRA
LGVVDEVREAVRQPAD SEQ ID NO: 40
MAKRGRKPKELVPGPGSIDPSDVPKLEGASVPVMS
TSYDVVVDREFDELLQGKDGLLVYHKMLSDGTVKN
ALNYIFGRIRSAKWYVEPASTDPEDIAIAAFIHAQ
LGIDDASVGKYPFGRLFAIYENAYIYGMAAGEIVL
TLGADGKLILDKIVPIHPFNIDEVLYDEEGGPKAL
KLSGEVKGGSQFVNGLEIPIWKTVVFLHNDDGSFT
GQSALRAAVPHWLAKRALILLINHGLERFMIGVPT
LTIPKSVRQGTKQWEAAKEIVKNFVQKPRHGIILP
DDWKFDTVDLKSAMPDAIPYLTYHDAGIARALGID
```

```
GCTCTGCCTAGCAAGATGCGCCGGGCGCTTGGCGT
GGTGGACGAGGTGAGGGAAGCGGTACGCCAACCCG
CCGATTAA
```

-continued

FNTVQLNMGVQAVNIGEFVSLTQQTIISLQREFAS

AVNLYLIPKLVLPNWPGATRFPRLTFEMEERNDFS

AAANLMGMLINAVKDSEDIPTELKALIDALPSKMR

RALGVVDEVREAVRQPADSRYLYTRRRR

SEQ ID NO: 41

ATGGCTAAGCGAGGACGTAAACCCAAGGAGCTGGT

CCCCGGACCTGGCTCCATTGACCCATCCGACGTTC

CCAAGCTCGAGGGCGCCTCCGTGCCGGTGATGTCC

ACCAGCTACGACGTGGTGGTTGACCGGGAGTTTGA

CGAGCTACTGCAGGGCAAGGACGGCCTGCTCGTCT

ACCACAAGATGCTCTCGGACGGCACGGTCAAGAAC

GCCCTCAACTACATCTTCGGGCGCATCCGCTCGGC

GAAGTGGTACGTAGAGCCCGCCTCTACCGACCCGG

AGGACATCGCCATCGCCGCCTTCATCCACGCCCAG

TTAGGCATAGACGATGCTTCGGTAGGCAAGTATCC

TTTTGGCCGTCTTTTCGCCATCTACGAAAACGCCT

ACATATACGGCATGGCCGCCGGGAAATCGTACTG

ACCCTTGGCGCGGACGGCAAGCTCATCCTTGACAA

AATCGTCCCTATCCACCCTTTCAACATTGACGAGG

TGCTTTACGACGAGGAAGGCGGTCCAAAGGCGCTA

AAGCTAAGCGGAGAGGTGAAGGGCGGAAGCCAGTT

CGTGAACGGGCTGGAGATTCCTATCTGGAAGACCG

TGGTCTTCCTGCACAACGACGACGGCTCCTTCACC

GGACAGAGCGCCCTCAGAGCCGCCGTTCCGCATTG

GCTAGCCAAACGCGCCCTTATCCTCCTCATCAACC

ACGGGCTAGAGCGCTTCATGATTGGCGTGCCCACC

CTCACCATCCCCAAGAGCGTGCGTCAGGGGACCAA

GCAATGGGAGGCCGCCAAGGAAATCGTCAAGAACT

TTGTTCAAAAACCACGGCATGGTATAATACTGCCT

GACGACTGGAAGTTTGACACGGTAGACCTGAAGTC

GGCCATGCCCGACGCCATTCCCTACCTGACCTACC

ACGACGCGGGCATCGCTAGGGCGCTTGGCATAGAC

TTCAACACCGTTCAGCTAAACATGGGGGTACAGGC

GGTCAACATCGGCGAGTTCGTAAGCCTGACCCAGC

AGACCATCATTTCGCTCCAGCGGGAGTTCGCTAGC

GCGGTCAACCTCTACCTCATCCCCAAGCTAGTGCT

TCCCAACTGGCCGGGCGCCACCCGCTTTCCCAGGC

TCACCTTTGAGATGGAGGAGCGTAACGACTTCTCC

GCCGCGGCCAACCTTATGGGCATGCTCATCAACGC

GGTTAAGGACTCCGAAGACATTCCCACCGAGCTCA

AGGCGCTAATAGACGCTCTGCCCAGCAAGATGCGC

-continued

CGGGCGCTTGGCGTGGTGGACGAGGTGAGGGAAGC

GGTACGCCAACCCGCCGATTCCCGCTACCTGTACA

CGCGAAGGAGGAGGTAG

REFERENCES

1. Wang, H. et al. Determining the Physical Properties of Molecules with Nanometer-Scale Pores. *ACS Sensors* 3, 251-263 (2018).
2. Derrington, I. M. et al. Nanopore DNA sequencing with MspA. *Proc. Natl. Acad. Sci. U.S.A.* 107, 16060-16065 (2010).
3. Nivala, J., Marks, D. B. & Akeson, M. Unfoldase-mediated protein translocation through an α-hemolysin nanopore. *Nat Biotechnol* 31, 247-250 (2013).
4. Rodriguez-Larrea, D. & Bayley, H. Multistep protein unfolding during nanopore translocation. *Nature Nanotech* 8, 288-295 (2013).
5. Gu, L. Q., Braha, O., Conlan, S., Cheley, S. & Bayley, H. Stochastic sensing of organic analytes by a pore-forming protein containing a molecular adapter. *Nature* 398, 686-690 (1999).
6. Butler, T. Z., Pavlenok, M., Derrington, I. M., Niederweis, M. & Gundlach, J. H. Single-molecule DNA detection with an engineered MspA protein nanopore. *Proc. Natl. Acad. Sci. U.S.A.* 105, 20647-20652 (2008).
7. Kasianowicz, J. J. et al. Analytical applications for pore-forming proteins. *Biochim Biophys Acta* 1858, 593-606 (2016).
8. Zhang, M. et al. Thermophoresis-Controlled Size-Dependent DNA Translocation through an Array of Nanopores. *ACS Nano* acsnano.8b00961 (2018). doi:10.1021/acsnano.8b00961
9. Larkin, J., Henley, R. Y., Jadhav, V., Korlach, J. & Wanunu, M. Length-independent DNA packing into nanopore zero-mode waveguides for low-input DNA sequencing. *Nat Nano* 12, 1169-1175 (2017).
10. McNally, B. et al. Optical Recognition of Converted DNA Nucleotides for Single-Molecule DNA Sequencing Using Nanopore Arrays. *Nano Lett* 10, 2237-2244 (2010).
11. Jain, M. et al. Nanopore sequencing and assembly of a human genome with ultra-long reads. *Nature Biotechnology* 36, 338-345 (2018).
12. Jain, M. et al. Improved data analysis for the MinION nanopore sequencer. *Nature Methods* 12, 351-356 (2015).
13. Loman, N. J., Quick, J. & Simpson, J. T. A complete bacterial genome assembled de novo using only nanopore sequencing data. *Nature Methods* 12, 733-735 (2015).
14. Garalde, D. R. et al. Highly parallel direct RNA sequencing on an array of nanopores. *Nature Methods* 15, 201-206 (2018).
15. Howorka, S. & Siwy, Z. Nanopore analytics: sensing of single molecules. *Chem. Soc. Rev.* 38, 2360 (2009).
16. Kasianowicz, J. J., Brandin, E., Branton, D. & Deamer, D. W. Characterization of individual polynucleotide molecules using a membrane channel. *Proc. Natl. Acad. Sci. U.S.A.* 93, 13770-13773 (1996).
17. Mohammad, M. M. et al. Engineering a rigid protein tunnel for biomolecular detection. *J Am Chem Soc* 134, 9521-9531 (2012).
18. Robertson, J. W. F. et al. Single-molecule mass spectrometry in solution using a solitary nanopore. *Proc. Natl. Acad. Sci. U.S.A.* 104, 8207-8211 (2007).

19. Merstorf, C. et al. Wild type, mutant protein unfolding and phase transition detected by single-nanopore recording. *ACS Chem Biol* 7, 652-658 (2012).
20. Huang, G., Willems, K., Soskine, M., Wloka, C. & Maglia, G. Electro-osmotic capture and ionic discrimination of peptide and protein biomarkers with FraC nanopores. *Nature Communications* 8, 935 (2017).
21. Piguet, F. et al. Identification of single amino acid differences in uniformly charged homopolymeric peptides with aerolysin nanopore. *Nature Communications* 9, (2018).
22. Luchian, T., Shin, S.-H. & Bayley, H. Kinetics of a three-step reaction observed at the single-molecule level. *Angew Chem Int Ed Engl* 42, 1926-1929 (2003).
23. Wescoe, Z. L., Schreiber, J. & Akeson, M. Nanopores discriminate among five C5-cytosine variants in DNA. *J Am Chem Soc* 136, 16582-16587 (2014).
24. Baaken, G. et al. High-Resolution Size-Discrimination of Single Nonionic Synthetic Polymers with a Highly Charged Biological Nanopore. *ACS Nano* 9, 6443-6449 (2015).
25. Fennouri, A. A. et al. Single molecule detection of glycosaminoglycan hyaluronic acid oligosaccharides and depolymerization enzyme activity using a protein nanopore. *ACS Nano* 6, 9672-9678 (2012).
26. Lee, J. et al. Semisynthetic Nanoreactor for Reversible Single-Molecule Covalent Chemistry. *ACS Nano* 10, 8843-8850 (2016).
27. Willems, K., Van Meervelt, V., Wloka, C. & Maglia, G. Single-molecule nanopore enzymology. *Philos. Trans. R. Soc. Lond., B, Biol. Sci.* 372, (2017).
28. Rosen, C. B., Rodriguez-Larrea, D. & Bayley, H. Single-molecule site-specific detection of protein phosphorylation with a nanopore. *Nat Biotechnol* 32, 179-181 (2014).
29. Verschueren, D. V., Jonsson, M. P. & Dekker, C. Temperature dependence of DNA translocations through solid-state nanopores. *Nanotechnology* 26, 234004 (2015).
30. Oukhaled, A. et al. Dynamics of completely unfolded and native proteins through solid-state nanopores as a function of electric driving force. *ACS Nano* 5, 3628-3638 (2011).
31. Yamazaki, H. et al. Label-Free Single-Molecule Thermoscopy Using a Laser-Heated Nanopore. *Nano Lett* 17, 7067-7074 (2017).
32. Song, L. et al. Structure of staphylococcal alpha-hemolysin, a heptameric transmembrane pore. *Science* 274, 1859-1866 (1996).
33. Cressiot, B. et al. Porphyrin-Assisted Docking of a Thermophage Portal Protein into Lipid Bilayers: Nanopore Engineering and Characterization. *ACS Nano* 11, 11931-11945 (2017).
34. Castell, O. K., Berridge, J. & Wallace, M. I. Quantification of membrane protein inhibition by optical ion flux in a droplet interface bilayer array. *Angewandte Chemie International Edition* 51, 3134-3138 (2012).
35. Hall, A. R. et al. Hybrid pore formation by directed insertion of α-haemolysin into solid-state nanopores. *Nature Nanotech* 5, 874-877 (2010).
36. Williams, L. S., Levdikov, V. M., Minakhin, L., Severinov, K. & Antson, A. A. 12-Fold symmetry of the putative portal protein from the *Thermus thermophilus* bacteriophage G20C determined by X-ray analysis. *Acta Crystallogr Sect F Struct Biol Cryst Commun* 69, 1239-1241 (2013).
37. Casjens, S. R. & Gilcrease, E. B. Determining DNA packaging strategy by analysis of the termini of the chromosomes in tailed-bacteriophage virions. *Methods Mol Biol* 502, 91-111 (2009).
38. Lebedev, A. A. et al. Structural framework for DNA translocation via the viral portal protein. *EMBO J* 26, 1984-1994 (2007).
39. Hoogerheide, D. P., Garaj, S. & Golovchenko, J. A. Probing Surface Charge Fluctuations with Solid-State Nanopores. *Physical Review Letters* 102, 256804 (2009).
40. Henrickson, S. E., Misakian, M., Robertson, B. & Kasianowicz, J. J. Driven DNA transport into an asymmetric nanometer-scale pore. *Phys Rev Lett* 85, 3057-3060 (2000).
41. Meller, A. & Branton, D. Single molecule measurements of DNA transport through a nanopore. *Electrophoresis* 23, 2583-2591 (2002).
42. Japrung, D., Henricus, M., Li, Q., Maglia, G. & Bayley, H. Urea Facilitates the Translocation of Single-Stranded DNA and RNA Through the α-Hemolysin Nanopore. *Biophysical Journal* 98, 1856-1863 (2010).
43. Cressiot, B. et al. Dynamics and Energy Contributions for Transport of Unfolded Pertactin through a Protein Nanopore. *ACS Nano* 9, 9050-9061 (2015).
44. Pastoriza-Gallego, M. et al. Dynamics of unfolded protein transport through an aerolysin pore. *J Am Chem Soc* 133, 2923-2931 (2011).
45. Oukhaled, A., Bacri, L., Pastoriza-Gallego, M., Betton, J.-M. & Pelta, J. Sensing proteins through nanopores: fundamental to applications. *ACS Chem Biol* 7, 1935-1949 (2012).
46. Stefureac, R., Long, Y.-T., Kraatz, H.-B., Howard, P. & Lee, J. S. Transport of alpha-helical peptides through alpha-hemolysin and aerolysin pores. *Biochemistry* 45, 9172-9179 (2006).
47. Pastoriza-Gallego, M. et al. Evidence of unfolded protein translocation through a protein nanopore. *ACS Nano* 8, 11350-11360 (2014).
48. Wang, H.-Y., Ying, Y.-L., Li, Y., Kraatz, H.-B. & Long, Y.-T. Nanopore Analysis of β-Amyloid Peptide Aggregation Transition Induced by Small Molecules. *Anal Chem* 83, 1746-1752 (2011).
49. Sutherland, T. C. et al. Structure of peptides investigated by nanopore analysis. *Nano Lett* 4, 1273-1277 (2004).
50. Meng, H. et al. Nanopore analysis of tethered peptides. *J Pept Sci* 16, 701-708 (2010).
51. Mereuta, L. et al. Slowing down single-molecule trafficking through a protein nanopore reveals intermediates for peptide translocation. *Sci Rep* 4, 3885-3885 (2014).
52. Whittingham, J. L., Edwards, D. J., Antson, A. A., Clarkson, J. M. & Dodson, G. G. Interactions of phenol and m-cresol in the insulin hexamer, and their effect on the association properties of B28 pro→Asp insulin analogues. *Biochemistry* 37, 11516-11523 (1998).
53. Kadima, W. et al. The influence of ionic strength and pH on the aggregation properties of zinc-free insulin studied by static and dynamic laser light scattering. *Biopolymers* 33, 1643-1657 (1993).
54. Van Meervelt, V. et al. Real-Time Conformational Changes and Controlled Orientation of Native Proteins Inside a Protein Nanoreactor. *J Am Chem Soc* 139, 18640-18646 (2017).
55. Skinner, G. M., van den Hout, M., Broekmans, O., Dekker, C. & Dekker, N. H. Distinguishing single- and double-stranded nucleic acid molecules using solid-state nanopores. *Nano Lett* 9, 2953-2960 (2009).

56. Lin, J., Fabian, M., Sonenberg, N. & Meller, A. Nanopore detachment kinetics of poly(A) binding proteins from RNA molecules reveals the critical role of C-terminus interactions. *Biophysical Journal* 102, 1427-1434 (2012).
57. Akeson, M., Branton, D., Kasianowicz, J. J., Brandin, E. & Deamer, D. W. Microsecond time-scale discrimination among polycytidylic acid, polyadenylic acid, and polyuridylic acid as homopolymers or as segments within single RNA molecules. *Biophysj* 77, 3227-3233 (1999).
58. Larkin, J. et al. Slow DNA transport through nanopores in hafnium oxide membranes. *ACS Nano* 7, 10121-10128 (2013).
59. Wanunu, M. et al. Rapid electronic detection of probe-specific microRNAs using thin nanopore sensors. *Nature Nanotech* 5, 807-814 (2010).

The teachings of all patents, published applications and references cited herein are incorporated by reference in their entirety.

While example embodiments have been particularly shown and described, it will be understood by those skilled in the art that various changes in form and details may be made therein without departing from the scope of the embodiments encompassed by the appended claims.

What is claimed is:

1. A nucleic acid molecule comprising a modification of a nucleic acid sequence of SEQ ID NO: 2, the modification comprising one or more of:

(i) a modification in a portion of the nucleic acid sequence that encodes an upper internal surface residue or a lower internal surface residue of a protein encoded by the nucleic acid sequence, the modification producing an alteration of an electrostatic surface potential of an upper internal surface or a lower internal surface of the protein encoded by the nucleic acid sequence;

(ii) a modification comprising an insertion of a cysteine residue into a protein encoded by the nucleic acid sequence or a replacement of an amino acid residue of a protein encoded by the nucleic acid sequence with a cysteine residue;

(iii) a modification to produce a modification of a tunnel loop residue of a protein encoded by the nucleic acid sequence, the modification in the tunnel loop residue comprising an expansion of a narrowest constriction of a tunnel loop of the protein encoded by the nucleic acid sequence, a restriction of the narrowest constriction of the tunnel loop of the protein encoded by the nucleic acid sequence, or a removal of the narrowest constriction of the tunnel loop of the protein encoded by the nucleic acid sequence;

(iv) a modification to produce a modification of a tunnel loop residue of a protein encoded by the nucleic acid sequence, the modification resulting in an alteration of an electrostatic charge property of a tunnel loop of the protein encoded by the nucleic acid sequence;

(v) a modification which alters an external charge of a protein encoded by the nucleic acid sequence;

(vi) a modification which promotes binding of a protein encoded by the nucleic acid sequence to a solid-state matrix;

(vii) a modification which extends an N-terminus or a C-terminus of a protein encoded by the nucleic acid sequence or an N-terminus or a C-terminus of a cleaved portion of the protein encoded by the nucleic acid sequence; and (viii) a deletion of an amino acid residue of at least one of a C-terminal region and an N-terminal region of a protein encoded by the nucleic acid sequence.

2. The nucleic acid molecule of claim 1, wherein the modification of SEQ ID NO: 2 comprises a modification in the portion of the nucleic acid sequence that encodes the lower internal surface residue of the protein encoded by the nucleic acid sequence, the modification producing the alteration of the electrostatic surface potential of the lower internal surface of the protein encoded by the nucleic acid sequence, and wherein the nucleic acid molecule comprises SEQ ID NO: 28.

3. The nucleic acid molecule of claim 1, wherein the modification of SEQ ID NO: 2 comprises the modification comprising an insertion of a cysteine residue into a protein encoded by the nucleic acid sequence or a replacement of an amino acid residue of a protein encoded by the nucleic acid sequence with a cysteine residue, and wherein the nucleic acid molecule comprises SEQ ID NO: 12 or SEQ ID NO: 38.

4. The nucleic acid molecule of claim 1, wherein the modification of SEQ ID NO: 2 comprises the modification to produce a modification of a tunnel loop residue of the protein encoded by the nucleic acid sequence, the modification in the tunnel loop residue comprising the expansion of the narrowest constriction of the tunnel loop of the protein encoded by the nucleic acid sequence, the restriction of the narrowest constriction of the tunnel loop of the protein encoded by the nucleic acid sequence, or the removal of the narrowest constriction of the tunnel loop of the protein encoded by the nucleic acid sequence, and wherein the nucleic acid molecule comprises one of: SEQ ID NO: 16, SEQ ID NO: 18, SEQ ID NO: 22, SEQ ID NO: 24 and SEQ ID NO: 26.

5. The nucleic acid molecule of claim 1, wherein the modification of SEQ ID NO: 2 comprises a modification to produce a modification of a tunnel loop residue of the protein encoded by the nucleic acid sequence, the modification resulting in the alteration of the electrostatic charge property of the tunnel loop of the protein encoded by the nucleic acid sequence, and wherein the nucleic acid molecule comprises SEQ ID NO: 20.

6. The nucleic acid molecule of claim 1, wherein the modification of SEQ ID NO: 2 comprises the modification which alters the external charge of the protein encoded by the nucleic acid sequence, and wherein the nucleic acid molecule comprises one of: SEQ ID NO: 10 and SEQ ID NO: 14.

7. The nucleic acid molecule of claim 1, wherein the modification of SEQ ID NO: 2 comprises the modification which promotes binding of the protein encoded by the nucleic acid sequence to the solid-state matrix, and wherein the nucleic acid molecule comprises one of: SEQ ID NO: 30, SEQ ID NO: 32 and SEQ ID NO: 36.

8. The nucleic acid molecule of claim 1, wherein the modification of SEQ ID NO: 2 comprises the modification which extends the N-terminus of the cleaved portion of the protein encoded by the nucleic acid sequence, and wherein the nucleic acid molecule comprises SEQ ID NO: 34.

9. The nucleic acid molecule of claim 1, wherein the modification of SEQ ID NO: 2 comprises a deletion of an amino acid residue of at least one of the C-terminal region and the N-terminal region of the protein encoded by the nucleic acid sequence, and wherein the nucleic acid molecule comprises one of: SEQ ID NO: 4, SEQ ID NO: 6 and SEQ ID NO: 8.

10. The nucleic acid molecule of claim 1, wherein the modification of SEQ ID NO: 2 comprises a modification to produce a modification in one or more of: a wing loop residue, a tunnel loop residue, an upper internal surface residue, a lower internal surface residue, an external surface residue, a C-terminal end residue, and an N-terminal end residue; of a protein encoded by the nucleic acid sequence.

11. A nucleic acid molecule comprising a modification of a nucleic acid sequence of SEQ ID NO: 2, the nucleic acid molecule comprising one of: SEQ ID NO: 28; SEQ ID NO: 12; SEQ ID NO: 38; SEQ ID NO: 16, SEQ ID NO: 18, SEQ ID NO: 22, SEQ ID NO: 24, SEQ ID NO: 26, SEQ ID NO: 20, SEQ ID NO: 10, SEQ ID NO: 14, SEQ ID NO: 30, SEQ ID NO: 32, SEQ ID NO: 36, SEQ ID NO: 34, SEQ ID NO: 4, SEQ ID NO: 6, and SEQ ID NO: 8.

12. A nucleic acid molecule comprising a modification of a nucleic acid sequence of SEQ ID NO: 2, the nucleic acid molecule comprising one of: SEQ ID NO: 28; SEQ ID NO: 38; SEQ ID NO: 16, SEQ ID NO: 18, SEQ ID NO: 24, SEQ ID NO: 26, SEQ ID NO: 20, SEQ ID NO: 10, SEQ ID NO: 14, SEQ ID NO: 30, SEQ ID NO: 32, SEQ ID NO: 36, SEQ ID NO: 34, SEQ ID NO: 4, SEQ ID NO: 6, and SEQ ID NO: 8.

13. A vector comprising a modification of a nucleic acid sequence of SEQ ID NO: 2, the modification comprising one or more of:
  (i) a modification in a portion of the nucleic acid sequence that encodes an upper internal surface residue or a lower internal surface residue of a protein encoded by the nucleic acid sequence, the modification producing an alteration of an electrostatic surface potential of an upper internal surface or a lower internal surface of the protein encoded by the nucleic acid sequence;
  (ii) a modification comprising an insertion of a cysteine residue into a protein encoded by the nucleic acid sequence or a replacement of an amino acid residue of a protein encoded by the nucleic acid sequence with a cysteine residue;
  (iii) a modification to produce a modification of a tunnel loop residue of a protein encoded by the nucleic acid sequence, the modification of the tunnel loop residue comprising an expansion of a narrowest constriction of a tunnel loop of the protein encoded by the nucleic acid sequence, a restriction of the narrowest constriction of the tunnel loop of the protein encoded by the nucleic acid sequence, or a removal of the narrowest constriction of the tunnel loop of the protein encoded by the nucleic acid sequence;
  (iv) a modification to produce a modification of a tunnel loop residue of a protein encoded by the nucleic acid sequence, the modification resulting in an alteration of an electrostatic charge property of a tunnel loop of the protein encoded by the nucleic acid sequence;
  (v) a modification which alters an external charge of a protein encoded by the nucleic acid sequence;
  (vi) a modification which promotes binding of a protein encoded by the nucleic acid sequence to a solid-state matrix;
  (vii) a modification which extends an N-terminus or a C-terminus of a protein encoded by the nucleic acid sequence or an N-terminus or a C-terminus of a cleaved portion of the protein encoded by the nucleic acid sequence; and
  (viii) a deletion of an amino acid residue of at least one of a C-terminal region and an N-terminal region of a protein encoded by the nucleic acid sequence.

14. A cell comprising the vector of claim 13.

15. The cell of claim 14, wherein the vector comprises a modification of a nucleic acid sequence of SEQ ID NO: 2, the modification comprising one or more of: SEQ ID NO: 28: SEQ ID NO: 12; SEQ ID NO: 38; SEQ ID NO: 16, SEQ ID NO: 18, SEQ ID NO: 22, SEQ ID NO: 24, SEQ ID NO: 26, SEQ ID NO: 20, SEQ ID NO: 10, SEQ ID NO: 14, SEQ ID NO: 30, SEQ ID NO: 32, SEQ ID NO: 36, SEQ ID NO: 34, SEQ ID NO: 4, SEQ ID NO: 6, and SEQ ID NO: 8.

16. The cell of claim 14, wherein the vector comprises a modification of a nucleic acid sequence of SEQ ID NO: 2, the modification comprising one or more of: SEQ ID NO: 28; SEQ ID NO: 38; SEQ ID NO: 16, SEQ ID NO: 18, SEQ ID NO: 24, SEQ ID NO: 26, SEQ ID NO: 20, SEQ ID NO: 10, SEQ ID NO: 14, SEQ ID NO: 30, SEQ ID NO: 32, SEQ ID NO: 36, SEQ ID NO: 34, SEQ ID NO: 4, SEQ ID NO: 6, and SEQ ID NO: 8.

17. A vector comprising a modification of a nucleic acid sequence of SEQ ID NO: 2, the modification comprising one or more of: SEQ ID NO: 28; SEQ ID NO: 12; SEQ ID NO: 38; SEQ ID NO: 16, SEQ ID NO: 18, SEQ ID NO: 22, SEQ ID NO: 24, SEQ ID NO: 26, SEQ ID NO: 20, SEQ ID NO: 10, SEQ ID NO: 14, SEQ ID NO: 30, SEQ ID NO: 32, SEQ ID NO: 36, SEQ ID NO: 34, SEQ ID NO: 4, SEQ ID NO: 6, and SEQ ID NO: 8.

18. A vector comprising a modification of a nucleic acid sequence of SEQ ID NO: 2, the modification comprising one or more of: SEQ ID NO: 28; SEQ ID NO: 38; SEQ ID NO: 16, SEQ ID NO: 18, SEQ ID NO: 24, SEQ ID NO: 26, SEQ ID NO: 20, SEQ ID NO: 10, SEQ ID NO: 14, SEQ ID NO: 30, SEQ ID NO: 32, SEQ ID NO: 36, SEQ ID NO: 34, SEQ ID NO: 4, SEQ ID NO: 6, and SEQ ID NO: 8.

* * * * *

SEQUENCE LISTING

```
Sequence total quantity: 41
SEQ ID NO: 1            moltype = AA  length = 448
FEATURE                 Location/Qualifiers
source                  1..448
                        mol_type = protein
                        organism = Thermus phage G20c
SEQUENCE: 1
MAKRGRKPKE LVPGPGSIDP SDVPKLEGAS VPVMSTSYDV VVDREFDELL QGKDGLLVYH  60
KMLSDGTVKN ALNYIFGRIR SAKWYVEPAS TDPEDIAIAA FIHAQLGIDD ASVGKYPFGR 120
LFAIYENAYI YGMAAGEIVL TLGADGKLIL DKIVPIHPFN IDEVLYDEEG GPKALKLSGE 180
VKGGSQFVSG LEIPIWKTVV FLHNDDGSFT GQSALRAAVP HWLAKRALIL LINHGLERFM 240
IGVPTLTIPK SVRQGTKQWE AAKEIVKNFV QKPRHGIILP DDWKFDTVDL KSAMPDAIPY 300
LTYHDAGIAR ALGIDFNTVQ LNMGVQAINI GEFVSLTQQT IISLQREFAS AVNLYLIPKL 360
VLPNWPSATR FPRLTFEMEE RNDFSAAANL MGMLINAVKD SEDIPTELKA LIDALPSKMR 420
RALGVVDEVR EAVRQPADSR YLYTRRRR                                   448

SEQ ID NO: 2            moltype = DNA  length = 1347
FEATURE                 Location/Qualifiers
source                  1..1347
                        mol_type = genomic DNA
                        organism = Thermus phage G20c
SEQUENCE: 2
atggctaagc gaggacgtaa acccaaagag ctggtccccg gacctggctc cattgaccca   60
tctgacgttc ccaagctcga gggcgcctcc gtgccggtga tgtccaccag ttacgacgtg  120
gtggtggacc gggagtttga cgagctactg caggggcaag acggcttgct cgtctaccac  180
aagatgctct cggacggcac ggttaagaac gccctcaact acatcttcgg acgcatccgc  240
tcggcgaagt ggtacgtaga gcccgcctct accgacccgg aagacatcgc catcgccgcc  300
ttcatccacg cccagttagg catagacgac gcttcggtgg gcaagtatcc ctttggccgc  360
cttttcgcca tctacgaaaa cgcctacata tacggcgatg ccgccgggga aatcgtacta  420
acccttggcg cggacggcaa gctcatcctt gacaaaatcg tccctatcca cccttttcaac 480
attgacgagg tgctttacga cgaggaaggc ggtccaaagg cgctaaagct aagcggagag  540
gtgaaggggg gaagccagtt tgtgagcggg ttggagattc ctatatggaa gaccgtggtc  600
ttcctgcaca acgacgacgg ctccttcacc ggacagagcg ccctcagagc cgccgtgccg  660
cattggctag ccaaacgagc cctcattctc ctcatcaacc acgggttgga gcgcttcatg  720
attggcgtgc ccaccctcac catccccaag agcgtgcgtc agggaaccaa gcaatgggag  780
gccgccaagg aaatcgtcaa gaactttgtt caaaaaccac ggcatggtat aatactgcct  840
gacgactgga agtttgacac ggtagacctg aagtcggcca tgcccgacgc cattccctac  900
ctgacctacc acgacgcggg catcgctagg gcgcttggca tagacttcaa caccgttcaa  960
ctaaacatgg gggtacaggc gataaacatc ggcgagttcg taagcctgac ccagcagacc 1020
atcatttcgc tccagcggga gttcgctagc gcggtcaacc tctacctcat cccccaagcta 1080
gtgcttccca actggccgag cgctactcgc tttcctaggc tcacctttga gatggaggag 1140
cgcaacgact tctccgccgc ggccaacctt atgggcatgc tcatcaacgc ggttaaggac 1200
tccgaagaca ttcccaccga gctcaaggcg ctaatagacg ctctgcctag caagatgcgc 1260
cgggcgcttg gcgtggtgga cgaggtgagg gaagcggtac gccaacccgc cgattcccgc 1320
tacctgtaca cgcgaaggag gaggtag                                   1347

SEQ ID NO: 3            moltype = AA  length = 446
FEATURE                 Location/Qualifiers
source                  1..446
                        mol_type = protein
                        organism = Thermus phage G20c
SEQUENCE: 3
MAKRGRKPKE LVPGPGSIDP SDVPKLEGAS VPVMSTSYDV VVDREFDELL QGKDGLLVYH  60
KMLSDGTVKN ALNYIFGRIR SAKWYVEPAS TDPEDIAIAA FIHAQLGIDD ASVGKYPFGR 120
LFAIYENAYI YGMAAGEIVL TLGADGKLIL DKIVPIHPFN IDEVLYDEEG GPKALKLSGE 180
VKGGSQFVSG LEIPIWKTVV FLHNDDGSFT GQSALRAAVP HWLAKRALIL LINHGLERFM 240
IGVPTLTIPK SVRQGTKQWE AAKEIVKNFV QKPRHGIILP DDWKFDTVDL KSAMPDAIPY 300
LTYHDAGIAR ALGIDFNTVQ LNMGVQAINI GEFVSLTQQT IISLQREFAS AVNLYLIPKL 360
VLPNWPSATR FPRLTFEMEE RNDFSAAANL MGMLINAVKD SEDIPTELKA LIDALPSKMR 420
RALGVVDEVR EAVRQPADLE HHHHHH                                     446
```

| SEQ ID NO: 4 | moltype = DNA length = 1341 |
|---|---|
| FEATURE | Location/Qualifiers |
| misc_feature | 1..1341 |
| | note = Thermus Thermophilus Bacteriophage G20C and Affinity Tag; WT 1-438 C-term |
| source | 1..1341 |
| | mol_type = other DNA |
| | organism = synthetic construct |

SEQUENCE: 4

```
atggctaagc gaggacgtaa acccaaagag ctggtccccg acctggctc cattgaccca   60
tctgacgttc ccaagctcga gggcgcctcc gtgccggtga tgtccaccag ttacgacgtg  120
gtggtggacc gggagtttga cgagctactg cagggcaagg acggcttgct cgtctaccac  180
aagatgctct cggacggcac ggttaagaac gcccctcaact acatcttcgg acgcatccgc  240
tcggcgaagt ggtacgtaga gccgccctct accgacccgg aagacatcgc catcgccgcc  300
ttcatccacg cccagttagg catagacgac gcttcggtgg gcaagtatcc ctttggccgc  360
cttttcgcca tctacgaaaa cgcctacata tacggcatgg ccgccgggga aatcgtacta  420
acccttggcg cggacggcaa gctcatcctt gacaaaatcg tccctatcca ccctttcaac  480
attgacgagg tgctttacga cgaggaaggc ggtccaaagc cgctaaagct aagcggagag  540
gtgaagggcg gaagccagtt tgtgagcggg ttggagattc ctatatggaa gaccgtggtc  600
ttcctgcaca acgacgacgg ctccttcacc ggacagagcg ccctcagagc gccgtgccg  660
cattggctag ccaaacgagc cctcattctc ctcatcaacc acggattgga gcgcttcatg  720
attggcgtgc ccaccctcac catcccaag agcgtgcgtc agggaaccaa gcaatggagg  780
gccgccaagg aaatcgtcaa gactttgtt caaaaccac ggcatggtat aatactgcct  840
gacgactgga gtttgacac ggtagacctg aagtcggcca tgcccgacgc cattccctac  900
ctgacctacc acgacgcggg catcgctagg gcgcttggca tagacttcaa caccgttcaa  960
ctaaacatgg gggtacaggc gataaacatc ggcgagttcg taagcctgac ccagcagacc 1020
atcatttcgc tccagcggga gttcgctagc gcggtcaacc tctacctcat ccccaagcta 1080
gtgcttccca actggccgag cgctactcgt tttcctaggc tcacctttga tgaggag    1140
cgcaacgact tctccgccgc ggccaacctt atgggcatgc tcatcaacgc ggttaaggac 1200
tccgaagaca tttcccaccga gctcaaggcg ctaatagacg ctctgcctag caagatgcgc 1260
cgggcgcttg gcgtggtgga cgaggtgagg gaagcggtac gccaacccgc cgatctcgag 1320
caccaccacc accaccacta g                                           1341
```

| SEQ ID NO: 5 | moltype = AA length = 441 |
|---|---|
| FEATURE | Location/Qualifiers |
| source | 1..441 |
| | mol_type = protein |
| | organism = Thermus phage G20c |

SEQUENCE: 5

```
GPAMAKRGRK PKELVPGPGS IDPSDVPKLE GASVPVMSTS YDVVVDREFD ELLQGKDGLL   60
VYHKMLSDGT VKNALNYIFG RIRSAKWYVE PASTDPEDIA IAAFIHAQLG IDDASVGKYP  120
FGRLFAIYEN AYIYGMAAGE IVLTLGADGK LILDKIVPIH PFNIDEVLYD EEGGPKALKL  180
SGEVKGGSQF VSGLEIPIWK TVVFLHNDDG SFTGQSALRA AVPHWLAKRA LILLINHGLE  240
RFMIGVPTLT IPKSVRQGTK QWEAAKEIVK NFVQKPRHGI ILPDDWKFDT VDLKSAMPDA  300
IPYLTYHDAG IARALGIDFN TVQLNMGVQA INIGEFVSLT QQTIISLQRE FASAVNLYLI  360
PKLVLPNWPS ATRFPRLTFE MEERNDFSAA ANLMGMLINA VKDSEDIPTE LKALIDALPS  420
KMRRALGVVD EVREAVRQPA D                                           441
```

| SEQ ID NO: 6 | moltype = DNA length = 1383 |
|---|---|
| FEATURE | Location/Qualifiers |
| misc_feature | 1..1383 |
| | note = Thermus Thermophilus Bacteriophage G20C and Affinity Tag; WT 1-438 3C prot |
| source | 1..1383 |
| | mol_type = other DNA |
| | organism = synthetic construct |

SEQUENCE: 6

```
atgggcagca gccatcatca tcatcatcac agcagcggcc tggaagttct gttccaggga   60
ccagcaatgg ctaagcgagg acgtaaaccc aaagagctgg tccccggacc tggctccatt  120
gacccatctg acgttcccaa gctcgagggc gcctccgtgc cggtgatgtc caccagttac  180
gacgtggtgg tggaccggga gtttgacgag ctactgcagg gcaaggacgg cttgctcgtc  240
taccacaaga tgctctcgga cggcacggtt aagaacgccc tcaactacat cttcggacgc  300
atccgctcgg cgaagtggta cgtagagccc gcctctaccg acccgaaga catcgccatc  360
gcccgccttca tccacgccca gttaggcata gacgacgctt cggtgggcaa gtatcccttt  420
ggccgccttt tcgccatcta cgaaaacgcc tacatatacg gcatggccgc cggggaaatc  480
gtactaaccc ttggcgcgga cggcaagctc atccttgaca aaatcgtccc tatccaccct  540
ttcaacattg acgaggtgct ttacgacgag gaaggcggtc caaaggcgct aaagctaagc  600
ggagaggtga agggcggaag ccagtttgtg agcgggttgg agattcctat atggaagacc  660
gtggtcttcc tgcacaacga cgacggctcc ttcaccggac agagcgccct cagagcgccg  720
gtgccgcatt ggctagccaa acgagccctc attcctcca tcaaccacgg gttggagcgc  780
ttcatgattg gcgtgcccac cctcaccatc cccaagagcg tgcgtcaggg aaccaagcaa  840
tggaggccgc caaggaaat cgtcaagaac tttgttcaaa aaccacggca tggtataata  900
ctgcctgacg actggaagtt tgacacggta gacctgaagt cggccatgcc cgacgccatt  960
ccctacctga ctaccacga cgcgggcatc gctagggcgc ttggcataga cttcaacacc 1020
gttcaactaa acatgggggt acaggcgata aacatcggcg agttcgtaag cctgacccag 1080
cagaccatca tttcgctcca gcgggagttc gctagcgcgg tcaacctcta cctcatcccc 1140
aagctagtgc ttcccaactg gccgagcgct actcgctttc ctaggctcac ctttgagatg 1200
gaggagcgca acgacttctc cgccgcggcc aaccttatgg gcatgctcat caacgcggtt 1260
aaggactccg aagacattcc caccgagctc aaggcgctaa tagacgctct gcctagcaag 1320
```

-continued

```
atgcgccggg cgcttggcgt ggtggacgag gtgagggaag cggtacgcca acccgccgat   1380
taa                                                                 1383

SEQ ID NO: 7              moltype = AA   length = 417
FEATURE                   Location/Qualifiers
source                    1..417
                          mol_type = protein
                          organism = Thermus phage G20c
SEQUENCE: 7
GPAKLEGASV PVMSTSYDVV VDREFDELLQ GKDGLLVYHK MLSDGTVKNA LNYIFGRIRS    60
AKWYVEPAST DPEDIAIAAF IHAQLGIDDA SVGKYPFGRL FAIYENAYIY GMAAGEIVLT   120
LGADGKLILD KIVPIHPFNI DEVLYDEEGG PKALKLSGEV KGGSQFVSGL EIPIWKTVVF   180
LHNDDGSFTG QSALRAAVPH WLAKRALILL INHGLERFMI GVPTLTIPKS VRQGTKQWEA   240
AKEIVKNFVQ KPRHGIILPD DWKFDTVDLK SAMPDAIPYL TYHDAGIARA LGIDFNTVQL   300
NMGVQAINIG EFVSLTQQTI ISLQREFASA VNLYLIPKLV LPNWPSATRF PRLTFEMEER   360
NDFSAAANLM GMLINAVKDS EDIPTELKAL IDALPSKMRR ALGVVDEVRE AVRQPAD     417

SEQ ID NO: 8              moltype = DNA   length = 1311
FEATURE                   Location/Qualifiers
misc_feature              1..1311
                          note = Thermus Thermophilus Bacteriophage G20C and Affinity
                           Tag; WT Nanopore
source                    1..1311
                          mol_type = other DNA
                          organism = synthetic construct
SEQUENCE: 8
atgggcagca gccatcatca tcatcatcac agcagcggcc tggaagttct gttccaggga    60
ccagcaaagc tcgagggcgc ctccgtgccg gtgatgtcca ccagttacga cgtggtggtg   120
gaccgggagt ttgacgagct actgcagggc aaggacggct gctcgtcta ccacaagatg    180
ctctcggacg gcacggttaa gaacgccctc aactacatct tcggacgcat ccgctcggcg   240
aagtggtacg tagagcccgc ctctaccgac ccggaagaca tcgccatcgc cgccttcatc   300
cacgcccagt taggcataga cgacgcttcg gtgggcaagt atcccttttgg ccgccttttc   360
gccatctacg aaaacgccta catatacggc atggccgccg ggaaatcgt actaaccctt    420
ggcgcggacg gcaagctcat ccttgacaaa atcgtcccta tccacccttt caacattgga   480
gaggtgcttt acgacgagga aggcggtcca aagcgctaa agctaagcgg agaggtgaag    540
ggcggaagcc agtttgtgag cgggttggag attcctatat ggaagaccgt ggtcttcctg   600
cacaacgacg acggctcctt caccggacag agcgccctca gagccgccgt gccgcattgg   660
ctagccaaac gagccctcat tctcctcatc aaccacgggt tggagcgctt catgattggc   720
gtgccaaacc tcaccatccc caagagcgtc cgtcagggaa ccaagcaatg ggaggccgcc   780
aaggaaatcg tcaagaactt tgttcaaaaa cccggcatg gtataatact gcctgacgac    840
tggaagtttg acacggtaga cctgaagtcg gccatgcccg acgccattcc ctacctgacc   900
taccacgacg cgggcatcgc tagggcgctt ggcatagact tcaacaccgt tcaactaaac   960
atggggtac aggcgataaa catcgggag ttcgtaagcc tgaccagca gaccatcatt    1020
tcgctccagc gggagttcgc tagcgcggtc aacctctacc tcatccccaa gctagtgctt   1080
cccaactggc cgagcgctac tcgctttcct aggctcacct ttgagatgga ggagcgcaac   1140
gacttctccg ccgcggccaa ccttatgggc atgctcatca cgcggttaa ggactccgaa    1200
gacattccca ccgagctcaa ggcgctaata acgctctgc ctagcaagat cgccggggcg    1260
cttggcgtgg tggacgaggt gagggaagcg gtacgccaac ccgccgatta a           1311

SEQ ID NO: 9              moltype = AA   length = 417
FEATURE                   Location/Qualifiers
REGION                    1..417
                          note = L230E
source                    1..417
                          mol_type = protein
                          organism = synthetic construct
SEQUENCE: 9
GPAKLEGASV PVMSTSYDVV VDREFDELLQ GKDGLLVYHK MLSDGTVKNA LNYIFGRIRS    60
AKWYVEPAST DPEDIAIAAF IHAQLGIDDA SVGKYPFGRL FAIYENAYIY GMAAGEIVLT   120
LGADGKLILD KIVPIHPFNI DEVLYDEEGG PKALKLSGEV KGGSQFVSGL EIPIWKTVVF   180
LHNDDGSFTG QSALRAAVPH WLAKRALIEL INHGLERFMI GVPTLTIPKS VRQGTKQWEA   240
AKEIVKNFVQ KPRHGIILPD DWKFDTVDLK SAMPDAIPYL TYHDAGIARA LGIDFNTVQL   300
NMGVQAINIG EFVSLTQQTI ISLQREFASA VNLYLIPKLV LPNWPSATRF PRLTFEMEER   360
NDFSAAANLM GMLINAVKDS EDIPTELKAL IDALPSKMRR ALGVVDEVRE AVRQPAD     417

SEQ ID NO: 10             moltype = DNA   length = 1311
FEATURE                   Location/Qualifiers
misc_feature              1..1311
                          note = L230E
source                    1..1311
                          mol_type = other DNA
                          organism = synthetic construct
SEQUENCE: 10
atgggcagca gccatcatca tcatcatcac agcagcggcc tggaagttct gttccaggga    60
ccagcaaagc tcgagggcgc ctccgtgccg gtgatgtcca ccagttacga cgtggtggtg   120
gaccgggagt ttgacgagct actgcagggc aaggacggct gctcgtcta ccacaagatg    180
ctctcggacg gcacggttaa gaacgccctc aactacatct tcggacgcat ccgctcggcg   240
aagtggtacg tagagcccgc ctctaccgac ccggaagaca tcgccatcgc cgccttcatc   300
cacgcccagt taggcataga cgacgcttcg gtgggcaagt atcccttttgg ccgccttttc   360
```

```
gccatctacg aaaacgccta catatacggc atggccgccg gggaaatcgt actaaccctt   420
ggcgcggacg gcaagctcat ccttgacaaa atcgtcccta tccacccttt caacattgac   480
gaggtgcttt acgacgagga aggcggtcca aaggcgctaa agctaagcgg agaggtgaag   540
ggcggaagcc agtttgtgag cgggttggag attcctatat ggaagaccgt ggtcttcctg   600
cacaacgacg acggctcctt caccggacag agcgccctca ccgccgccgt gccgcattgg   660
ctagccaaac gagccctcat tgagctcatc aaccacgggt tggagcgctt catgattggc   720
gtgcccaccc tcaccatccc caagagcgtg cgtcagggaa ccaagcaatg ggaggccgcc   780
aaggaaatcg tcaagaactt tgttcaaaaa ccacggcatg gtataatact gcctgacgac   840
tggaagtttg acacggtaga cctgaagtcg gccatgcccg acgccattcc ctacctgacc   900
taccacgacg cgggcatcgc tagggcgctt ggcatagact tcaacaccgt tcaactaaac   960
atggggggtac aggcgataaa catcggcgag ttcgtaagcc tgacccagca gaccatcatt  1020
tcgctccagc gggagttcgc tagcgcgtc aacctctacc tcatcccaa gctagtgctt    1080
cccaactggc cgagcgctac tcgctttcct aggctcacct ttgagatgga ggagcgcaac  1140
gacttctccg ccgcggccaa ccttatgggc atgctcatca cgcggttaa ggactccgaa   1200
gacattccca ccgagctcaa ggcgctaata gacgctctgc ctagcaagat gcgccgggcg  1260
cttggcgtgg tggacgaggt gagggaagcg gtacgccaac cgccgatta  a            1311

SEQ ID NO: 11           moltype = AA   length = 417
FEATURE                 Location/Qualifiers
REGION                  1..417
                        note = 49C
VARIANT                 251
                        note = Xaa = Any Amino Acid
source                  1..417
                        mol_type = protein
                        organism = synthetic construct
SEQUENCE: 11
GPAKLEGASV PVMSTSYDVV VDREFDECLQ GKDGLLVYHK MLSDGTVKNA LNYIFGRIRS    60
AKWYVEPAST DPEDIAIAAF IHAQLGIDDA SVGKYPFGRL FAIYENAYIY GMAAGEIVLT  120
LGADGKLILD KIVPIHPFNI DEVLYDEEGG PKALKLSGEV KGGSQFVSGL EIPIWKTVVF  180
LHNDDGSFTG QSALRAAVPH WLAKRALILL INHGLERFMI GVPTLTIPKS VRQGTKQWEA  240
AKEIVKNFVQ XPRHGIILPD DWKFDTVDLK SAMPDAIPYL TYHDAGIARA LGIDFNTVQL  300
NMGVQAINIG EFVSLTQQTI ISLQREFASA VNLYLIPKLV LPNWPSATRF PRLTFEMEER  360
NDFSAAANLM GMLINAVKDS EDIPTELKAL IDALPSKMRR ALGVVDEVRE AVRQPAD     417

SEQ ID NO: 12           moltype = DNA   length = 1311
FEATURE                 Location/Qualifiers
misc_feature            1..1311
                        note = 49C
variation               810
                        note = n = A,T,C or G
source                  1..1311
                        mol_type = other DNA
                        organism = synthetic construct
SEQUENCE: 12
atgggcagca gccatcatca tcatcatcac agcagcggcc tggaagttct gttccaggga    60
ccagcaaagc tcgagggcgc ctccgtgccg gtgatgtcca cagttacga cgtggtggtg   120
gaccgggagt ttgacgagtg tctgcagggc aaggacggct tgctcgtcta ccacaagatg   180
ctctcggacg gcacggttaa gaacgccctc aactacatct tcggacgcat ccgctcgggcg  240
aagtggtacg tagagcccgc ctctaccgac ccggaagaca tcgccatcgc cgccttcatc   300
cacgcccagt taggcataga cgacgcttcg gtgggcaagt atcccttgg cgcctttca    360
gccatctacg aaaacgccta catatacggc atggccgccg gggaaatcgt actaaccctt   420
ggcgcggacg gcaagctcat ccttgacaaa atcgtcccta tccacccttt caacattgac   480
gaggtgcttt acgacgagga aggcggtcca aaggcgctaa agctaagcgg agaggtgaag   540
ggcggaagcc agtttgtgag cgggttggag attcctatat ggaagaccgt ggtcttcctg   600
cacaacgacg acggctcctt caccggacag agcgccctca gccgccgt gccgcattgg     660
ctagccaaac gagccctcat tctcctcatc aaccacgggt tggagcgctt catgattggc   720
gtgcccaccc tcaccatccc caagagcgtg cgtcagggaa ccaagcaatg ggaggccgcc   780
aaggaaatcg tcaagaactt tgttcaaaan ccacggcatg gtataatact gcctgacgac   840
tggaagtttg acacggtaga cctgaagtcg gccatgcccg acgccattcc ctacctgacc   900
taccacgacg cgggcatcgc tagggcgctt ggcatagact tcaacaccgt tcaactaaac   960
atggggggtac aggcgataaa catcggcgag ttcgtaagcc tgacccagca gaccatcatt  1020
tcgctccagc gggagttcgc tagcgcgtc aacctctacc tcatcccaa gctagtgctt    1080
cccaactggc cgagcgctac tcgctttcct aggctcacct ttgagatgga ggagcgcaac  1140
gacttctccg ccgcggccaa ccttatgggc atgctcatca cgcggttaa ggactccgaa   1200
gacattccca ccgagctcaa ggcgctaata gacgctctgc ctagcaagat gcgccgggcg  1260
cttggcgtgg tggacgaggt gagggaagcg gtacgccaac cgccgatta  a            1311

SEQ ID NO: 13           moltype = AA   length = 417
FEATURE                 Location/Qualifiers
REGION                  1..417
                        note = 40E
VARIANT                 251
                        note = Xaa = Any Amino Acid
source                  1..417
                        mol_type = protein
                        organism = synthetic construct
SEQUENCE: 13
GPAKLEGASV PVMSTSYDEV VDREFDELLQ GKDGLLVYHK MLSDGTVKNA LNYIFGRIRS    60
```

```
AKWYVEPAST DPEDIAIAAF IHAQLGIDDA SVGKYPFGRL FAIYENAYIY GMAAGEIVLT    120
LGADGKLILD KIVPIHPFNI DEVLYDEEGG PKALKLSGEV KGGSQFVSGL EIPIWKTVVF    180
LHNDDGSFTG QSALRAAVPH WLAKRALILL INHGLERFMI GVPTLTIPKS VRQGTKQWEA    240
AKEIVKNFVQ XPRHGIILPD DWKFDTVDLK SAMPDAIPYL TYHDAGIARA LGIDFNTVQL    300
NMGVQAINIG EFVSLTQQTI ISLQREFASA VNLYLIPKLV LPNWPSATRF PRLTFEMEER    360
NDFSAAANLM GMLINAVKDS EDIPTELKAL IDALPSKMRR ALGVVDEVRE AVRQPAD       417

SEQ ID NO: 14           moltype = DNA   length = 1311
FEATURE                 Location/Qualifiers
misc_feature            1..1311
                        note = 40E
variation               810
                        note = n = A,T,C or G
source                  1..1311
                        mol_type = other DNA
                        organism = synthetic construct
SEQUENCE: 14
atgggcagca gccatcatca tcatcatcac agcagcggcc tggaagttct gttccaggga     60
ccagcaaagc tcgagggcgc ctccgtgccg gtgatgtcca ccagttacga cgaggtggtg    120
gaccgggagt ttgacgagct actgcaggdc aaggacggct tgctcgtcta ccacaagatg    180
ctctcggacg gcacggttaa gaacgccctc aactacatct tcggacgcat ccgctcggcg    240
aagtggtacg tagagcccgc ctctaccgac ccggaagaca tcgccatcgc cgccttcatc    300
cacgcccagt taggcataga cgacgcttcg gtgggcaagt atcccttttgg ccgccttttc    360
gccatctacg aaaacgccta catatacggc atggccgccg ggaaaatcgt actaacccttt    420
ggcgcggacg gcaagctcat ccttgacaaa atcgtcccta tccaccctttt caacattgac    480
gaggtgcttt acgacgagga aggcggtcca aaggcgctaa agctaagcgg agaggtgaag    540
ggcggaagcc agtttgtgag cgggttggag attcctatat ggaagaccgt ggtcttcctg    600
cacaacgacg acggctcctt caccggacag agcgccctca gagccgccgt gccgcattgg    660
ctagccaaac gagccctcat tctcctcatc aaccacgggt tggagcgctt catgattggc    720
gtgcccaccc tcaccatccc caagagcgtg cgtcagggaa ccaagcaatg ggaggccgcc    780
aaggaaatcg tcaagaactt tgttcaaaan ccacggcatg gtataatact gcctgacgac    840
tggaagtttg acacggtaga cctgaagtcg gccatgcccg acgccattcc ctacctgacc    900
taccacgacg cgggcatcgc tagggcgctt ggcatagact tcaacaccgt tcaactaaac    960
atggggtac aggcgataaa catcggcgag ttcgtaagcc tgacccagca gaccatcatt    1020
tcgctccagc gggagttcgc tagcgcggtc aacctctacc tcatcccaa gctagtgctt    1080
cccaactggc cgagcgctac tgctttcct aggctcacct ttgagatgga ggagcgcaac    1140
gacttctccg ccgcggccaa ccttatgggc atgctcatca cgcgggttaa ggactccgaa    1200
gacattccca ccgagctcaa ggcgctaata acgcgctctgc ctagcaagat cgccggggcg    1260
cttggcgtgg tggacgaggt gagggaagcg gtacgccaac ccgccgatta a            1311

SEQ ID NO: 15           moltype = AA   length = 417
FEATURE                 Location/Qualifiers
REGION                  1..417
                        note = G
source                  1..417
                        mol_type = protein
                        organism = synthetic construct
SEQUENCE: 15
GPAKLEGASV PVMSTSYDVV VDREFDELLQ GKDGLLVYHK MLSDGTVKNA LNYIFGRIRS     60
AKWYVEPAST DPEDIAIAAF IHAQLGIDDA SVGKYPFGRL FAIYENAYIY GMAAGEIVLT    120
LGADGKLILD KIVPIHPFNI DEVLYDEEGG PKALKLSGEV KGGSQFVSGL EIPIWKTVVF    180
LHNDDGSFTG QSALRAAVPH WLAKRALILL INHGLERFMI GVPTLTIPKS VRQGTKQWEA    240
AKEIVKNFVQ KPRHGIILPD DWKFDTVDLK SAMPDAIPYL TYHDAGIARA LGIDFNTVQL    300
NMGGQAINIG EFVSLTQQTI ISLQREFASA VNLYLIPKLV LPNWPSATRF PRLTFEMEER    360
NDFSAAANLM GMLINAVKDS EDIPTELKAL IDALPSKMRR ALGVVDEVRE AVRQPAD       417

SEQ ID NO: 16           moltype = DNA   length = 1311
FEATURE                 Location/Qualifiers
misc_feature            1..1311
                        note = G
source                  1..1311
                        mol_type = other DNA
                        organism = synthetic construct
SEQUENCE: 16
atgggcagca gccatcatca tcatcatcac agcagcggcc tggaagttct gttccaggga     60
ccagcaaagc tcgagggcgc ctccgtgccg gtgatgtcca ccagttacga cgtggtggtg    120
gaccgggagt ttgacgagct actgcaggdc aaggacggct tgctcgtcta ccacaagatg    180
ctctcggacg gcacggttaa gaacgccctc aactacatct tcggacgcgc ccgctcggcg    240
aagtggtacg tagagcccgc ctctaccgac ccggaagaca tcgccatcgc cgccttcatc    300
cacgcccagt taggcataga cgacgcttcg gtgggcaagt atcccttttgg ccgccttttc    360
gccatctacg aaaacgccta catatacggc atggccgccg ggaaaatcgt actaacccttt    420
ggcgcggacg gcaagctcat ccttgacaaa atcgtcccta tccaccctttt caacattgac    480
gaggtgcttt acgacgagga aggcggtcca aaggcgctaa agctaagcgg agaggtgaag    540
ggcggaagcc agtttgtgag cgggttggag attcctatat ggaagaccgt ggtcttcctg    600
cacaacgacg acggctcctt caccggacag agcgccctca gagccgccgt gccgcattgg    660
ctagccaaac gagccctcat tctcctcatc aaccacgggt tggagcgctt catgattggc    720
gtgcccaccc tcaccatccc caagagcgtg cgtcagggaa ccaagcaatg ggaggccgcc    780
aaggaaatcg tcaagaactt tgttcaaaaa ccacggcatg gtataatact gcctgacgac    840
tggaagtttg acacggtaga cctgaagtcg gccatgcccg acgccattcc ctacctgacc    900
```

```
taccacgacg  cgggcatcgc  tagggcgctt  ggcatagact  tcaacaccgt  tcaactaaac   960
atgggggac   aggcgataaa  catcggcgag  ttcgtaagcc  tgacccagca  gaccatcatt  1020
tcgctccagc  gggagttcgc  tagcgcggtc  aacctctacc  tcatcccaa   gctagtgctt  1080
cccaactggc  cgagcgctac  tcgctttcct  aggctcacct  ttgagatgga  ggagcgcaac  1140
gacttctccg  ccgcggccaa  ccttatgggc  atgctcatca  acgcggttaa  ggactccgaa  1200
gacattccca  ccgagctcaa  ggcgctaata  gacgctctgc  ctagcaagat  gcgccgggcg  1260
cttggcgtgg  tggacgaggt  gagggaagcg  gtacgccaac  ccgccgatta  a           1311
```

```
SEQ ID NO: 17           moltype = AA   length = 417
FEATURE                 Location/Qualifiers
REGION                  1..417
                        note = M
source                  1..417
                        mol_type = protein
                        organism = synthetic construct
SEQUENCE: 17
GPAKLEGASV PVMSTSYDVV VDREFDELLQ GKDGLLVYHK MLSDGTVKNA LNYIFGRIRS       60
AKWYVEPAST DPEDIAIAAF IHAQLGIDDA SVGKYPFGRL FAIYENAYIY GMAAGEIVLT      120
LGADGKLILD KIVPIHPFNI DEVLYDEEGG PKALKLSGEV KGGSQFVSGL EIPIWKTVVF      180
LHNDDGSFTG QSALRAAVPH WLAKRALILL INHGLERFMI GVPTLTIPKS VRQGTKQWEA      240
AKEIVKNFVQ KPRHGIILPD DWKFDTVDLK SAMPDAIPYL TYHDAGIARA LGIDFNTVQL      300
NMGMQAINIG EFVSLTQQTI ISLQREFASA VNLYLIPKLV LPNWPSATRF PRLTFEMEER      360
NDFSAAANLM GMLINAVKDS EDIPTELKAL IDALPSKMRR ALGVVDEVRE AVRQPAD         417
```

```
SEQ ID NO: 18           moltype = DNA   length = 1311
FEATURE                 Location/Qualifiers
misc_feature            1..1311
                        note = M
source                  1..1311
                        mol_type = other DNA
                        organism = synthetic construct
SEQUENCE: 18
atgggcagca gccatcatca tcatcatcac agcagcggcc tggaagttct gttccaggga       60
ccagcaaagc tcgagggcgc ctccgtgccg gtgatgtcca cagttacga  cgtggtggtg      120
gaccgggagt ttgacgagct actgcagggc aaggacggtc tgctcgtcta ccacaagatg      180
ctctcggacg gcacggttaa gaacgccctc aactacatct tcggacgcat ccgctcggcg      240
aagtggtacg tagagcccgc ctctaccgac ccggaagaca tcgccatcgc cgccttcatc      300
cacgcccagt taggcataga cgacgcttcg gtgggcaagt atcccttggg ccgcttttc      360
gccatctacg aaaacgccta catatacggc atggccgcgg gggaaatcgt actaaccctt     420
ggcgcggacg gcaagctcat ccttgacaaa atcgtcccta tccacccttt caacattgac     480
gaggtgcttt acgacgagga aggcggtcca aaggcgctaa agctaagcgg agaggtgaag     540
ggcggaagcc agtttgtgag cgggttggag attcctatat ggaagaccgt ggtcttcctg     600
cacaacgacg acggctcctt caccggacag agcgcgctca gccgcattgg                660
ctagccaaac gagccctcat tctcctcatc aaccacgggt tggagcgctt catgattggc     720
gtgcccaccc tcaccatccc caagagcgtg cgtcagggaa ccaagcaatg ggaggccgcc     780
aaggaaatcg tcaagaactt tgttcaaaaa ccacggcatg gtataatact gcctgacgac     840
tggaagtttg acacggtaga cctgaagtcg gccatgccg  gccattcc  ctacctgacc      900
taccacgacg cgggcatcgc tagggcgctt ggcatagact tcaacaccgt tcaactaaac     960
atggggatgc aggcgataaa catcggcgag ttcgtaagcc tgacccagca gaccatcatt    1020
tcgctccagc gggagttcgc tagcgcggtc aacctctacc tcatcccaa  gctagtgctt    1080
cccaactggc cgagcgctac tcgctttcct aggctcacct ttgagatgga ggagcgcaac    1140
gacttctccg ccgcggccaa ccttatgggc atgctcatca acgcggttaa ggactccgaa    1200
gacattccca ccgagctcaa ggcgctaata gacgctctgc ctagcaagat gcgccgggcg    1260
cttggcgtgg tggacgaggt gagggaagcg gtacgccaac ccgccgatta a             1311
```

```
SEQ ID NO: 19           moltype = AA   length = 417
FEATURE                 Location/Qualifiers
REGION                  1..417
                        note = K
source                  1..417
                        mol_type = protein
                        organism = synthetic construct
SEQUENCE: 19
GPAKLEGASV PVMSTSYDVV VDREFDELLQ GKDGLLVYHK MLSDGTVKNA LNYIFGRIRS       60
AKWYVEPAST DPEDIAIAAF IHAQLGIDDA SVGKYPFGRL FAIYENAYIY GMAAGEIVLT      120
LGADGKLILD KIVPIHPFNI DEVLYDEEGG PKALKLSGEV KGGSQFVSGL EIPIWKTVVF      180
LHNDDGSFTG QSALRAAVPH WLAKRALILL INHGLERFMI GVPTLTIPKS VRQGTKQWEA      240
AKEIVKNFVQ KPRHGIILPD DWKFDTVDLK SAMPDAIPYL TYHDAGIARA LGIDFNTVQL      300
NMGVQAKNIG EFVSLTQQTI ISLQREFASA VNLYLIPKLV LPNWPSATRF PRLTFEMEER      360
NDFSAAANLM GMLINAVKDS EDIPTELKAL IDALPSKMRR ALGVVDEVRE AVRQPAD         417
```

```
SEQ ID NO: 20           moltype = DNA   length = 1311
FEATURE                 Location/Qualifiers
misc_feature            1..1311
                        note = K
source                  1..1311
                        mol_type = other DNA
                        organism = synthetic construct
SEQUENCE: 20
```

```
atgggcagca gccatcatca tcatcatcac agcagcggcc tggaagttct gttccaggga    60
ccagcaaagc tcgagggcgc ctccgtgccg gtgatgtcca ccagttacga cgtggtggtg   120
gaccgggagt ttgacgagct actgcagggc aaggacggct tgctcgtcta ccacaagatg   180
ctctcggacg gcacggttaa gaacgccctc aactacatct tcggacgcat ccgctcggcg   240
aagtggtacg tagagcccgc ctctaccgac ccggaagaca tcgccatcgc cgccttcatc   300
cacgcccagt taggcataga cgacgcttcg gtgggcaagt atccctttgg ccgccttttc   360
gccatctacg aaaacgccta catatacggc atggccgccg gggaaatcgt actaacccct   420
ggcgcggacg gcaagctcat ccttgacaaa atcgtcccta tccacccttt caacattgac   480
gaggtgcttt acgacgagga aggcggtcca aaggcgctaa agctaagcgg agaggtgaag   540
ggcggaagcc agtttgtgag cggggttgag attcctatat ggaagaccgt ggtcttcctg   600
cacaacgacg acggctcctt caccggacag agcgccctca gagccgccgt gccgcattgg   660
ctagccaaac gagccctcat tctcctcatc aaccacgggt tggagcgctt catgattggc   720
gtgcccaccc tcaccatccc caagagcgtg cgtcagggaa ccaagcaatg ggaggccgcc   780
aaggaaatcg tcaagaactt tgttcaaaaa ccacggcatg gtataatact gcctgacgac   840
tggaagtttg acacggtaga cctgaagtcg gccatgcccg acgccattcc ctacctgacc   900
taccacgacg cgggcatcgc cagggcgctt ggcatagact tcaacaccgt tcaactaaac   960
atgggggtac aggcgaagaa catcggcgag ttcgtaagcc tgacccagca gaccatcatt  1020
tcgctccagc gggagttcgc tagcgcggtc aacctctacc tcatcccgaa gctagtgctt  1080
cccaactggc cgagcgctac tcgctttcct aggctcacct ttgagatgga ggagcgcaac  1140
gacttctccg ccgcggccaa cctgatgggc atgctcatca cgcggttaa ggactccgaa  1200
gacattccca ccgagctcaa ggcgctaata gacgctctgc ctagcaagat gcgccggggcg  1260
cttggcgtgg tggacgaggt gagggaagcg gtacgccaac ccgccgatta a           1311
```

SEQ ID NO: 21           moltype = AA   length = 417
FEATURE                 Location/Qualifiers
REGION                  1..417
                        note = CGG
source                  1..417
                        mol_type = protein
                        organism = synthetic construct
SEQUENCE: 21
```
GPAKLEGASV PVMSTSYDVV VDREFDECLQ GKDGLLVYHK MLSDGTVKNA LNYIFGRIRS    60
AKWYVEPAST DPEDIAIAAF IHAQLGIDDA SVGKYPFGRL FAIYENAYIY GMAAGEIVLT   120
LGADGKLILD KIVPIHPFNI DEVLYDEEGG PKALKLSGEV KGGSQFVSGL EIPIWKTVVF   180
LHNDDGSFTG QSALRAAVPH WLAKRALILL INHGLERFMI GVPTLTIPKS VRQGTKQWEA   240
AKEIVKNFVQ KPRHGIILPD DWKFDTVDLK SAMPDAIPYL TYHDAGIARA LGIDFNTVQL   300
NMGGQAGNIG EFVSLTQQTI ISLQREFASA VNLYLIPKLV LPNWPSATRF PRLTFEMEER   360
NDFSAAANLM GMLINAVKDS EDIPTELKAL IDALPSKMRR ALGVVDEVRE AVRQPAD      417
```

SEQ ID NO: 22           moltype = DNA   length = 1311
FEATURE                 Location/Qualifiers
misc_feature            1..1311
                        note = CGG
source                  1..1311
                        mol_type = other DNA
                        organism = synthetic construct
SEQUENCE: 22
```
atgggcagca gccatcatca tcatcatcac agcagcggcc tggaagttct gttccaggga    60
ccagcaaagc tcgagggcgc ctccgtgccg gtgatgtcca ccagttacga cgtggtggtg   120
gaccgggagt ttgacgagtg tctgcagggc aaggacggct tgctcgtcta ccacaagatg   180
ctctcggacg gcacggttaa gaacgccctc aactacatct tcggacgcat ccgctcggcg   240
aagtggtacg tagagcccgc ctctaccgac ccggaagaca tcgccatcgc cgccttcatc   300
cacgcccagt taggcataga cgacgcttcg gtgggcaagt atccctttgg ccgccttttc   360
gccatctacg aaaacgccta catatacggc atggccgccg gggaaatcgt actaacccct   420
ggcgcggacg gcaagctcat ccttgacaaa atcgtcccta tccacccttt caacattgac   480
gaggtgcttt acgacgagga aggcggtcca aaggcgctaa agctaagcgg agaggtgaag   540
ggcggaagcc agtttgtgag cggggttgag attcctatat ggaagaccgt ggtcttcctg   600
cacaacgacg acggctcctt caccggacag agcgccctca gagccgccgt gccgcattgg   660
ctagccaaac gagccctcat tctcctcatc aaccacgggt tggagcgctt catgattggc   720
gtgcccaccc tcaccatccc caagagcgtg cgtcagggaa ccaagcaatg ggaggccgcc   780
aaggaaatcg tcaagaactt tgttcaaaaa ccacggcatg gtataatact gcctgacgac   840
tggaagtttg acacggtaga cctgaagtcg gccatgcccg acgccattcc ctacctgacc   900
taccacgacg cgggcatcgc cagggcgctt ggcatagact tcaacaccgt tcaactaaac   960
atggggggac aggcgggaaa catcggcgag ttcgtaagcc tgacccagca gaccatcatt  1020
tcgctccagc gggagttcgc tagcgcggtc aacctctacc tcatcccgaa gctagtgctt  1080
cccaactggc cgagcgctac tcgctttcct aggctcacct ttgagatgga ggagcgcaac  1140
gacttctccg ccgcggccaa cctgatgggc atgctcatca cgcggttaa ggactccgaa  1200
gacattccca ccgagctcaa ggcgctaata gacgctctgc ctagcaagat gcgccggggcg  1260
cttggcgtgg tggacgaggt gagggaagcg gtacgccaac ccgccgatta a           1311
```

SEQ ID NO: 23           moltype = AA   length = 416
FEATURE                 Location/Qualifiers
REGION                  1..416
                        note = Loop2GG
source                  1..416
                        mol_type = protein
                        organism = synthetic construct
SEQUENCE: 23
```
GPAKLEGASV PVMSTSYDVV VDREFDELLQ GKDGLLVYHK MLSDGTVKNA LNYIFGRIRS    60
```

```
AKWYVEPAST DPEDIAIAAF IHAQLGIDDA SVGKYPFGRL FAIYENAYIY GMAAGEIVLT    120
LGADGKLILD KIVPIHPFNI DEVLYDEEGG PKALKLSGEV KGGSQFVSGL EIPIWKTVVF    180
LHNDDGSFTG QSALRAAVPH WLAKRALILL INHGLERFMI GVPTLTIPKS VRQGTKQWEA    240
AKEIVKNFVQ KPRHGIILPD DWKFDTVDLK SAMPDAIPYL TYHDAGIARA LGIDFNTVQL    300
NMGGGNIGE  FVSLTQQTII SLQREFASAV NLYLIPKLVL PNWPSATRFP RLTFEMEERN    360
DFSAAANLMG MLINAVKDSE DIPTELKALI DALPSKMRRA LGVVDEVREA VRQPAD        416

SEQ ID NO: 24           moltype = DNA   length = 1308
FEATURE                 Location/Qualifiers
misc_feature            1..1308
                        note = Loop2GG
source                  1..1308
                        mol_type = other DNA
                        organism = synthetic construct
SEQUENCE: 24
atgggcagca gccatcatca tcatcatcac agcagcggcc tggaagttct gttccaggga     60
ccagcaaagc tcgagggcgc ctccgtgccg gtgatgtcca cagttacga cgtggtggtg    120
gaccgggagt ttgacgagct actgcagggc aaggacggct tgctcgtcta ccacaagatg    180
ctctcggacg gcacggttaa gaacgccctc aactacatct tcggacgcat ccgctcggcg    240
aagtggtacg tagagcccgc ctctaccgac ccggaagaca tcgccatcgc cgccttcatc    300
cacgcccagt taggcataga cgacgcttcg gtgggcaagt atcccttggg ccgccttttc    360
gccatctacg aaaacgccta catatacggc atggccgccg gggaaatcgt actaaccctt    420
ggcgcggacg gcaagctcat ccttgacaaa atcgtcccta tccacccttt caacattgac    480
gaggtgcttt acgacgagga aggcggtcca aaggcgctaa agctaagcgg agaggtgaag    540
ggcggaagcc agtttgtgag cgggttggag attcctatat ggaagaccgt ggtcttcctg    600
cacaacgacg acggctcctt caccggacag agccgcctca agccgccgt gccgcattgg    660
ctagccaaac gagccctcat tctcctcatc aaccacgggt tggagcgctt catgattggc    720
gtgcccaccc tcaccatccc caagagcgtg cgtcagggaa ccaagcaatg gaggccgcc    780
aaggaaatc  tcaagaactt tgttcaaaaa ccacggcatg gtataatact gcctgacgac    840
tggaagtttg acacggtaga cctgaagtcg gccatgcccga cgccattcc ctacctgacc    900
taccacgacg cgggcatcgc taggcgcgtt ggcatagact tcaacaccgt tcaactaaac    960
atgggggag  cgtaacat  cggcgagttc gtaagcctga cccagcagac catcatttcg   1020
ctccagcggg agttcgctag cgcggtcaac ctctacctca tccccaagct agtgcttcc  1080
aactggccga gcgctactcg ctttcctagg ctcacctttg agatggagga gcgcaacgac  1140
ttctccgccg cggccaacct tatgggcatg ctcatcaacg cggttaagga ctccgaagac  1200
attcccaccg agctcaaggc gctaatagac gctctgccta gcaagatgcg ccgggcgctt  1260
ggcgtggtgg acgaggtgag ggaagcggta cgccaacccg ccgattaa              1308

SEQ ID NO: 25           moltype = AA   length = 410
FEATURE                 Location/Qualifiers
REGION                  1..410
                        note = 49CLoop3G
source                  1..410
                        mol_type = protein
                        organism = synthetic construct
SEQUENCE: 25
GPAKLEGASV PVMSTSYDVV VDREFDECLQ GKDGLLVYHK MLSDGTVKNA LNYIFGRIRS     60
AKWYVEPAST DPEDIAIAAF IHAQLGIDDA SVGKYPFGRL FAIYENAYIY GMAAGEIVLT    120
LGADGKLILD KIVPIHPFNI DEVLYDEEGG PKALKLSGEV KGGSQFVSGL EIPIWKTVVF    180
LHNDDGSFTG QSALRAAVPH WLAKRALILL INHGLERFMI GVPTLTIPKS VRQGTKQWEA    240
AKEIVKNFVQ KPRHGIILPD DWKFDTVDLK SAMPDAIPYL TYHDAGIARA LGIDFNTVQL    300
GIGEFVSLTQ QTIISLQREF ASAVNLYLIP KLVLPNWPSA TRFPRLTFEM EERNDFSAAA    360
NLMGMLINAV KDSEDIPTEL KALIDALPSK MRRALGVVDE VREAVRQPAD              410

SEQ ID NO: 26           moltype = DNA   length = 1269
FEATURE                 Location/Qualifiers
misc_feature            1..1269
                        note = 49CLoop3G
variation               1266
                        note = n = A,T,C or G
source                  1..1269
                        mol_type = other DNA
                        organism = synthetic construct
SEQUENCE: 26
catcatcaca gcagcggcct ggaagttctg ttccagggac cagcaaagct cgagggcgcc     60
tccgtgccgg tgatgtccac cagttacgac gtggtggtgg accgggagtt tgacgagtgt    120
ctgcaggca  aggacggctt gctcgtctac cacaagatgc tctcggacgg cacggttaag    180
aacgccctca actacatctt cggacgcatc cgctcggcga agtggtacgt agagcccgcc    240
tctaccgacc cggaagacat cgccatcgcc gccttcatcc acgcccagtt aggcatagac    300
gacgcttcgg tgggcaagta tcccttgggc cgccttttcg ccatctacga aaacgcctac    360
atatacggca tggccgccgg ggaaatcgta ctaaccctttg gcgcggacgg caagctcatc    420
cttgacaaaa tcgtccctat ccaccctttc aacattgacg aggtgcttta cgacgaggaa    480
ggcggtccaa aggcgctaaa gctaagcgga gaggtgaagg gcggaagcca gtttgtgagc    540
gggttggaga ttcctatatg gaagaccgtg gtcttcctgc acaacgacga cggctccttc    600
accggacaga gcgccctcag agccgccgtg ccgcattggc tagccaaacg agccctcatt    660
ctcctcatca accacgggtt ggagcgcttc atgattggcg tgcccaccct caccatcccc    720
aagagcgtgc gtcagggaac caagcaatgg aggccgcca aggaaatcgt caagaacttt    780
gttcaaaaac cacggcatgg tataatactg cctgacgact ggaagtttga cacggtagac    840
ctgaagtcgg ccatgcccga cgccattccc tacctgacct accacgacgc gggcatcgct    900
```

```
agggcgcttg gcatagactt caacaccgtt caactaggta tcggcgagtt cgtaagcctg    960
acccagcaga ccatcatttc gctccagcgg gagttcgcta gcgcggtcaa cctctacctc   1020
atccccaagc tagtgcttcc caactggccg agcgctactc gctttcctag gctcaccttt   1080
gagatggagg agcgcaacga cttctccgcc gcggccaacc ttatgggcat gctcatcaac   1140
gcggttaagg actccgaaga cattcccacc gagctcaagg cgctaataga cgctctgcct   1200
agcaagatgc gccgggcgct tggcgtggtg gacgaggtga gggaagcggt acgccaaccc   1260
gccgantaa                                                           1269

SEQ ID NO: 27          moltype = AA  length = 417
FEATURE                Location/Qualifiers
REGION                 1..417
                       note = CD/N
source                 1..417
                       mol_type = protein
                       organism = synthetic construct
SEQUENCE: 27
GPAKLEGASV PVMSTSYDVV VDREFDECLQ GKDGLLVYHK MLSDGTVKNA LNYIFGRIRS    60
AKWYVEPAST DPEDIAIAAF IHAQLGIDDA SVGKYPFGRL FAIYENAYIY GMAAGEIVLT   120
LGADGKLILD KIVPIHPFNI DEVLYDEEGG PKALKLSGEV KGGSQFVSGL EIPIWKTVVF   180
LHNDDGSFTG QSALRAAVPH WLAKRALILL INHGLERFMI GVPTLTIPKS VRQGTKQWEA   240
AKEIVKNFVQ KPRHGIILPN DWKFNTVNLK SAMPNAIPYL TYHDAGIARA LGIDFNTVQL   300
NMGVQAINIG EFVSLTQQTI ISLQREFASA ANLYLIPKLV LPNWPSATRF PRLTFEMEER   360
NDFSAAANLM GMLINAVKDS EDIPTELKAL IDALPSKMRR ALGVVDEVRE AVRQPAD     417

SEQ ID NO: 28          moltype = DNA  length = 1311
FEATURE                Location/Qualifiers
misc_feature           1..1311
                       note = CD/N
source                 1..1311
                       mol_type = other DNA
                       organism = synthetic construct
SEQUENCE: 28
atgggcagca gccatcatca tcatcatcac agcagcggcc tggaagttct gttccaggga    60
ccagcaaagc tcgagggcgc ctccgtgccg gtgatgtcca cagttacga cgtcgtcgta   120
gaccgggagt ttgacgagtg tctgcagggc aaggacggct tgctcgtcta ccacaagtta   180
ctctcggacg gcacggttaa gaacgccctc aactacatct tcggacgcat ccgctcggcg   240
aagtggtacg tagagcccgc ctctaccgac ccggaagaca tcgccatcgc cgccttcatc   300
cacgcccagt taggcataga cgacgcttcg gtgggcaagt atcccttcgg ccgcttttc    360
gccatctaca aaaacgccta catatacggc atggccgacc gggaaatgt actaaccctct   420
ggcgcggacg gcaagctcat ccttgacaaa atcgtcccta tccacccttt caacattgac   480
gaggtgcttt acgacgagga aggcggtcca aaggcgctaa agctaagcgg agaggtgaag   540
ggcggaagcc agtttgtgag cgggttggag attcctatat ggaagaccgt ggtcttcctg   600
cacaacgacg acggcttcct cacggaacag agcgccgcgt gccgcattgg                 660
ctagccaaac gagccctcat tctcctcatc aaccacgggt tggagcgctt catgattggc   720
gtgcccaccc tcaccatccc caagagcgtg cgtcagggaa ccaagcaatg ggaggccgcc   780
aaggaaatcg tcaagaactt tgttcaaaaa ccacggcatg gtataatact gcctaacgac   840
tggaagttta acacggtaaa cctgaagtcg gccatgccca acgccattcc ctacctgacc   900
taccacgacg cgggcatcgc tagggcgctt ggcatagact tcaacaccgt tcaactaaac   960
atggggtac aggcgataaa catccggcgag ttcgtaagcc tgacccagca gaccatcatt  1020
tcgctccagc gggagttcgc tagcgcggcc aacctctacc tcatcccaa gctagtgctt  1080
cccaactggc cgagcgctac tcgctttcct aggctcacct ttgagatgga ggagcgcaac  1140
gacttctccg ccgcggccaa ccttatgggc atgctcatca cgcggttaa ggactccgaa  1200
gacattccca ccgagctcaa ggcgctaata gacgctctgc ctagcaagat gcgccgggcg  1260
cttggcgtgg tggacgaggt gagggaagcg gtacgccaac cgccgatta a           1311

SEQ ID NO: 29          moltype = AA  length = 424
FEATURE                Location/Qualifiers
REGION                 1..424
                       note = SIN1
source                 1..424
                       mol_type = protein
                       organism = synthetic construct
SEQUENCE: 29
GPAKLEGASV PVMSTSYDVV VDREFDEGTP GSRGLLQGKD GLLVYHKMLS DGTVKNALNY    60
IFGRIRSAKW YVEPASTDPE DIAIAAFIHA QLGIDDASVG KYPFGRLFAI YENAYIYGMA   120
AGEIVLTLGA DGKLILDKIV PIHPFNIDEV LYDEEGGPKA LKLSGEVKGG SQFVSGLEIP   180
IWKTVVFLHN DDGSFTGQSA LRAAVPHWLA KRALILLINH GLERFMIGVP TLTIPKSVRQ   240
GTKQWEAAKE IVKNFVQKPR HGIILPNDWK FNTVNLKSAM PNAIPYLTYH DAGIARALGI   300
DFNTVQLNMG VQAINIGEFV SLTQQTIISL QREFASAVNL YLIPKLVLPN WPSATRFPRL   360
TFEMEERNDF SAAANLMGML INAVKDSEDI PTELKALIDA LPSKMRRALG VVDEVREAVR   420
QPAD                                                               424

SEQ ID NO: 30          moltype = DNA  length = 1332
FEATURE                Location/Qualifiers
misc_feature           1..1332
                       note = SIN1
source                 1..1332
                       mol_type = other DNA
                       organism = synthetic construct
```

```
SEQUENCE: 30
atgggcagca gccatcatca tcatcatcac agcagcggcc tggaagttct gttccaggga    60
ccagcaaagc tcgagggcgc ctccgtgccg gtgatgtcca ccagttacga cgtggtggtg   120
gaccgggagt ttgacgaggg tacgccaggt tctcgcggcc tactgcaggg caaggacggc   180
ttgctcgtct accacaagat gctctcggac ggcacggtta agaacgcctc caactacatc   240
ttcggacgca tccgctcggc gaagtggtac gtagagcccg cctctaccga cccggaagac   300
atcgccatcg ccgccttcat ccacgcccag ttaggcatag acgacgcttc ggtgggcaag   360
tatccctttg gccgccttttt cgccatctac gaaaacgcct acatatacgg catggccgcc   420
ggggaaatcg tactaaccct tggcgcggan ggcaagctca tccttgacaa aatcgtcccct   480
atccacccttt tcaacattga cgaggtgctt tacgacgagg aaggcggtcc aaaggcgcta   540
aagctaagcg gagaggtgaa gggcggaagc cagtttgtga gcgggttgga gattcctata   600
tggaagaccg tggtcttcct gcacaacgac gacggctcct tcaccggaca gagcgccctc   660
agagccgccg tgccgcattg gctagccaaa cgagccctca ttctcctcat caaccacggg   720
ttggagcgct tcatgattgg cgtgcccacc ctcaccatcc ccaagagcgt gcgtcaggga   780
accaagcaat gggaggccgc caaggaaatc gtcaagaact tgttcaaaa accacggcat   840
ggtataatac tgcctaacga ctggaagttt aacacggtaa acctgaagtc ggccatgccc   900
aacgccattc cctacctgac ctaccacgac gcgggcatcg ctagggcgct tggcatagac   960
ttcaacaccg ttcaactaaa catgggggta caggcgataa acatcggcga gttcgtaagc  1020
ctgacccagc agaccatcat ttcgctccaa cgggagttcg ctagcgcggt caacctctac  1080
ctcatcccca agctagtgct tcccaactgg ccgagcgcta tcgctttccc taggctcacc  1140
tttgagatgg aggagcgcaa cgacttctcc gccgcggcca accttatggg catgctcatc  1200
aacgcggtta aggactccga agacattccc accgagctca aggcgctaat agacgctctg  1260
cctagcaaga tgcgcccggc gcttggcgtg gtggacgagg tgagggaagc ggtacgccaa  1320
cccgccgatt aa                                                     1332

SEQ ID NO: 31           moltype = AA   length = 425
FEATURE                 Location/Qualifiers
REGION                  1..425
                        note = SIN2
source                  1..425
                        mol_type = protein
                        organism = synthetic construct
SEQUENCE: 31
GPAKLEGASV PVMSTSYDVV VDREFDEGRK LPDAGLLQGK DGLLVYHKML SDGTVKNALN    60
YIFGRIRSAK WYVEPASTDP EDIAIAAFIH AQLGIDDASV GKYPFGRLFA IYENAYIYGM   120
AAGEIVLTLG ADGKLILDKI VPIHPFNIDE VLYDEEGGPK ALKLSGEVKG GSQFVSGLEI   180
PIWKTVVFLH NDDGSFTGQS ALRAAVPHWL AKRALILLIN HGLERFMIGV PTLTIPKSVR   240
QGTKQWEAAK EIVKNFVQKP RHGIILPNDW KFNTVNLKSA MPNAIPYLTY HDAGIARALG   300
IDFNTVQLNM GVQAINIGEF VSLTQQTIIS LQREFASAVN LYLIPKLVLP NWPSATRFPR   360
LTFEMEERND FSAAANLMGM LINAVKDSED IPTELKALID ALPSKMRRAL GVVDEVREAV   420
RQPAD                                                              425

SEQ ID NO: 32           moltype = DNA   length = 1335
FEATURE                 Location/Qualifiers
misc_feature            1..1335
                        note = SIN2
source                  1..1335
                        mol_type = other DNA
                        organism = synthetic construct
SEQUENCE: 32
atgggcagca gccatcatca tcatcatcac agcagcggcc tggaagttct gttccaggga    60
ccagcaaagc tcgagggcgc ctccgtgccg gtgatgtcca ccagttacga cgtggtggtg   120
gaccgggagt ttgacgaggg tcgtaaactg ccggatgcag gcctactgca gggcaaggac   180
ggcttgctcg tctaccacaa gatgctctcg gacggcacgg ttaagaacgc cctcaactac   240
atcttcggac gcatccgctc ggcgaagtgg tacgtagagc ccgcctctac cgacccggaa   300
gacatcgcca tcgccgcctt catccacgcc cagttaggca tagacgacgc ttcggtgggc   360
aagtatccct ttggccgcct ttttgccatc tacgaaaacg cctacatata cggcatggcc   420
gccggggaaa tcgtactaac ccttggcgcg gacggcaagc tcatccttga caaaatcgtc   480
cctatccacc ctttcaacat tgacgaggtg ctttacgacg aggaaggcgg tccaaaggcg   540
ctaaagctaa gcggagaggt gaagggcgga agccagtttg tgagcgggtt ggagattcct   600
atatggaaga ccgtggtctt cctgcacaac gacgacggcc ttcaccggac agagcgccct   660
cagagccgcc gtgccgcatt ggctagccaa acgagccctc attctcctca tcaaccacgg   720
gttggagcgc ttcatgattg gcgtgcccac cctcaccatc cccaagagcg tgcgtcaggg   780
aaccaagcaa tgggaggccg ccaaggaaat cgtcaagaac ttgttcaaaa accacggcat   840
ggtataatac tgcctaacga ctggaagttt aacacggtaa acctgaagtc ggccatgccc   900
aacgccattc cctacctgac ctaccacgac gcgggcatcg ctagggcgct tggcatagac   960
ttcaacaccg ttcaactaaa catgggggta caggcgataa acatcggcga gttcgtaagc  1020
ctgacccagc agaccatcat ttcgctccag cgggagttcg ctagcgcggt caacctctac  1080
ctcatcatcc ccaagctagt gcttcccaac tggccgagcg ctactcgctt cctaggctca  1140
cctttgagat ggaggagcgc aacgacttct ccgccgcggc caaccttatg ggcatgctc   1200
atcaacgcgg ttaaggactc cgaagacatt cccaccgagc tcaaggcgct aatagacgct  1260
ctgcctagca gagatgcgcc gggcgcttgg cgtggtggac gaggtgaggg agcggtacgc  1320
caacccgccg attaa                                                  1335

SEQ ID NO: 33           moltype = AA   length = 431
FEATURE                 Location/Qualifiers
REGION                  1..431
                        note = SIN3
source                  1..431
```

```
                        mol_type = protein
                        organism = synthetic construct
SEQUENCE: 33
GPASSKKSGS YSGSKGSKLE GASVPVMSTS YDVVVDREFD ECLQGKDGLL VYHKMLSDGT    60
VKNALNYIFG RIRSAKWYVE PASTDPEDIA IAAFIHAQLG IDDASVGKYP FGRLFAIYEN   120
AYIYGMAAGE IVLTLGADGK LILDKIVPIH PFNIDEVLYD EEGGPKALKL SGEVKGGSQF   180
VSGLEIPIWK TVVFLHNDDG SFTGQSALRA AVPHWLAKRA LILLINHGLE RFMIGVPTLT   240
IPKSVRQGTK QWEAAKEIVK NFVQKPRHGI ILPNDWKFNT VNLKSAMPNA IPYLTYHDAG   300
IARALGIDFN TVQLNMGVQA INIGEFVSLT QQTIISLQRE FASAANLYLI PKLVLPNWPS   360
ATRFPRLTFE MEERNDFSAA ANLMGMLINA VKDSEDIPTE LKALIDALPS KMRRALGVVD   420
EVREAVRQPA D                                                       431

SEQ ID NO: 34           moltype = DNA  length = 1353
FEATURE                 Location/Qualifiers
misc_feature            1..1353
                        note = SIN3
source                  1..1353
                        mol_type = other DNA
                        organism = synthetic construct
SEQUENCE: 34
atgggcagca gccatcatca tcatcatcac agcagcggcc tggaagttct gttccaggga    60
ccagcaagca gtaagaaaag tggaagctat agcggcagca aaggcagcaa gctcgagggc   120
gcctccgtgc cggtgatgtc caccagttac gacgtggtgg tggaccggga gtttgacgag   180
tgtctgcagg gcaaggacgg cttgctcgtc taccacaaga tgctctcgga cggcacggtt   240
aagaacgccc tcaactacat cttcggacgc atccgctcgg cgaagtggta cgtagagccc   300
gcctctaccg acccggaaga catcgccatc gccgccttca tccacgccca gttaggcata   360
gacgacgctt cggtgggcaa gtatcccttt ggccgccttt tcgccatcta cgaaaacgcg   420
tacatatacg gcatggccgc cggggaaatc gtactaaccc ttggcgcgga cggcaagctc   480
atccttgaca aaatcgtccc tatccacccc ttcaacattg acgaggtgct ttacgacgag   540
gaaggcggtc caaaggcgct aaagctaagc ggagaggtga agggcggaag ccagtttgtg   600
agcgggttgg agattcctat atggaagacc gtggtcttcc tgcacaacga cgacggctcc   660
ttcaccggac agagcgccct cagagccgcc gtgccgcatt ggctagccaa acgagccctc   720
attctcctca tcaaccacgg gttggagcgc ttcatgattg gcgtgcccac cctcaccatc   780
cccaagagcg tgcgtcaggg aaccaagcaa tgggaggccg ccaaggaaat cgtcaagaac   840
tttgttcaaa aaccacggca tggtataata ctgcctaacg actggaagtt taacacggta   900
aacctgaagt cggccatgcc caacgccatt cctacctga cctaccacga cgcgggcatc    960
gctagggcgc ttggcataga cttcaacacc gttcaactaa acatgggggt acaggcgata   1020
aacatcggcg agttcgtaag cctgacccag cagaccatca tttcgctcca gcgggagttc   1080
gctagcgcgg ccaacctcta cctcatcccc aagctagtgc ttcccaactg cgcgagcgct   1140
actcgctttc ctaggctcac ctttgagatg gaggagcgca acgacttctc cgccgcggcc   1200
aaccttatgg gcatgctcat caacgcggtt aaggactccg aagacattcc caccgagctc   1260
aaggcgctaa tagacgctct gcctagcaag atgcgccggg cgcttggcgt ggtggacgag   1320
gtgagggaag cggtacgcca acccgccgat taa                                1353

SEQ ID NO: 35           moltype = AA  length = 426
FEATURE                 Location/Qualifiers
REGION                  1..426
                        note = SIN4
source                  1..426
                        mol_type = protein
                        organism = synthetic construct
SEQUENCE: 35
GPAKLEGASV PVMSTSYDVV VDREFDEGYR PGFYFRLLQG KDGLLVYHKM LSDGTVKNAL    60
NYIFGRIRSA KWYVEPASTD PEDIAIAAFI HAQLGIDDAS VGKYPFGRLF AIYENAYIYG   120
MAAGEIVLTL GADGKLILDK IVPIHPFNID EVLYDEEGGP KALKLSGEVK GGSQFVSGLE   180
IPIWKTVVFL HNDDGSFTGQ SALRAAVPHW LAKRALILLI NHGLERFMIG VPTLTIPKSV   240
RQGTKQWEAA KEIVKNFVQK PRHGIILPND WKFNTVNLKS AMPNAIPYLT YHDAGIARAL   300
GIDFNTVQLN MGVQAINIGE FVSLTQQTII SLQREFASAV NLYLIPKLVL PNWPSATRFP   360
RLTFEMEERN DFSAAANLMG MLINAVKDSE DIPTELKALI DALPSKMRRA LGVVDEVREA   420
VRQPAD                                                             426

SEQ ID NO: 36           moltype = DNA  length = 1338
FEATURE                 Location/Qualifiers
misc_feature            1..1338
                        note = SIN4
source                  1..1338
                        mol_type = other DNA
                        organism = synthetic construct
SEQUENCE: 36
atgggcagca gccatcatca tcatcatcac agcagcggcc tggaagttct gttccaggga    60
ccagcaaagc tcgagggcgc ctccgtgccg gtgatgtcca ccagttacga cgtggtggtg   120
gaccgggagt ttgacgaggg atatcgcccg ggctttatt tcgcctact gcagggcaag    180
gacggcttgc tcgtctacca caagatgctc tcggacggca cggttaagaa cgccctcaac   240
tacatcttcg gacgcatccg ctcggcgaag tggtacgtag agcccgcctc taccgacccg   300
gaagacatcg ccatcgccgc cttcatccac gcccagttag gcatagacga cgcttcggtg   360
ggcaagtatc cctttggccg cctttttcgcc atctacgaaa acgcctacat atacggcatg   420
gccgccgggg aaatcgtact aacccttggc ggacggca gctcatcct tgacaaaatc     480
gtccctatcc acccttttcaa cattgacgag gtgctttacg acgaggaagg cggtccaaag   540
gcgctaaagc taagcggaga ggtgaagggc ggaagccagt ttgtgagcgg gttggagatt   600
```

-continued

```
cctatatgga agaccgtggt cttcctgcac aacgacgacg gctccttcac cggacagagc 660
gccctcagag ccgccgtgcc gcattggcta gccaaacgag ccctcattct cctcatcaac 720
cacgggttgg agcgcttcat gattggcgtg cccaccctca ccatcccaa gagcgtgcgt 780
cagggaacca agcaatggga ggccgccaag gaaatcgtca agaactttgt tcaaaaacca 840
cggcatggta taatactgcc taacgactgg aagtttaaca cggtaaacct gaagtcggcc 900
atgcccaacg ccattcccta cctgacctac cacgacgcgg gcatcgctag ggcgcttggc 960
atagacttca acaccgttca actaaacatg ggggtacagg cgataaacat cggcgagttc 1020
gtaagcctga cccagcagac catcatttcg ctccagcggg agttcgctag cgcggtcaac 1080
ctctacctca tccccaagct agtgcttccc aactggccga gcgctactcg ctttcctagg 1140
ctcaccttg agatggagga gcgcaacgac ttctccgccg cggccaacct tatgggcatg 1200
ctcatcaacg cggttaagga ctccgaagac attccaccg agctcaaggc gctaatagac 1260
gctctgccta gcaagatgcg ccgggcgctt ggcgtggtgg acgaggtgag ggaagcggta 1320
cgccaacccg ccgattaa                                             1338
```

```
SEQ ID NO: 37           moltype = AA  length = 445
FEATURE                 Location/Qualifiers
REGION                  1..445
                        note = 400C
source                  1..445
                        mol_type = protein
                        organism = synthetic construct
SEQUENCE: 37
MAKRGRKPKE LVPGPGSIDP SDVPKLEGAS VPVMSTSYDV VVDREFDELL QGKDGLLVYH  60
KMLSDGTVKN ALNYIFGRIR SAKWYVEPAS TDPEDIAIAA FIHAQLGIDD ASVGKYPFGR 120
LFAIYENAYI YGMAAGEIVL TLGADGKLIL DKIVPIHPFN IDEVYDEEGG PKALKLSGEV 180
KGGSQFVSGL EIPIWKTVVF LHNDDGSFTG QSALRAAVPH WLAKRALILL INHGLERFMI 240
GVPTLTIPKS VRQGTKQWEA AKEIVKNFVQ KPRHGIILPD DWKFDTVDLK SAMPDAIPYL 300
TYHDAGIARA LGIDFNTVQL NMGVQAINIG EFVSLTQQTI ISLQREFASA VNLYLIPKLV 360
LPNWPSATRF PRLTFEMEER NDFSAAANLM GMLINAVKCS EDIPTELKAL IDALPSKMRR 420
ALGVVDEVRE AVRQPADLEH HHHHH                                      445
```

```
SEQ ID NO: 38           moltype = DNA  length = 1341
FEATURE                 Location/Qualifiers
misc_feature            1..1341
                        note = 400C
variation               494
                        note = n = A,T,C or G
source                  1..1341
                        mol_type = other DNA
                        organism = synthetic construct
SEQUENCE: 38
atggctaagc gaggacgtaa acccaaagag ctggtccccg gacctggctc cattgaccca  60
tctgacgttc ccaagctcga gggcgcctcc gtgccggtga tgtccaccag ttacgacgtg 120
gtggtggacc gggagtttga cgagctactg cagggcaagg acggcttgct cgtctaccac 180
aagatgctct cggacggcac ggttaagaac gccctcaact acatcttcgg acgcatccgc 240
tcggcgaagt ggtacgtaga gccgcctct accgacccgg aagacatcgc catcgccgcc 300
ttcatccacg cccagttagg catagacgac gcttcggtgg gcaagtatcc ctttggccgc 360
cttttcgcca tctacgaaaa cgcctacata tacggcatgg ccgccgggga aatcgtacta 420
acccttggcg cggacggcaa gctcatcctt gacaaaatcg tccctatcca cccttttcaac 480
attgacgagg tgcnttacga cgaggaaggc ggtccaaagg cgctaaagct aagcggagag 540
gtgaaggcg gaagccagtt tgtgaacggg ttggagattc ctatatggaa gaccgtggtc 600
ttcctgcaca acgacgacgg ctccttcacc ggacagagcc cctcagagc cgccgtgccg 660
cattggctag ccaaacgagc cctcattctc ctcatcaacc acgggttgga gcgcttcatg 720
attggcgtgc ccaccctcac catcccaag agcgtgcgtc agggaaccaa gcaatgggag 780
gccgccaagg aaatcgtcaa gaactttgtt caaaaaccac ggcatggtat aatactgcct 840
aacgactgga gtttgacac ggtagacctg aagtcggcca tgcccgacgc cattccctac 900
ctgacctacc acgacgcggg catcgctagg gcgcttggca tagacttcaa caccgttcaa 960
ctaaacatgg gggtacaggc gataaacatc ggcgagttcg taagcctgac ccagcagacc 1020
atcatttcgc tccagcggga gttcgctagc gcggtcaacc tctacctcat ccccaagcta 1080
gtgcttccca actggccgag cgctactcgc tttcctaggc tcaccttga gatggaggag 1140
cgcaacgact tctccgccgc ggccaacctt atgggcatgc tcatcaacgc ggttaagtgc 1200
tccgaagaca ttcccaccga gctcaaggcg ctaatagacg ctctgcctag caagatgcgc 1260
cgggcgcttg gcgtggtgga cgaggtgagg gaagcggtac gccaacccgc cgatctcgag 1320
caccaccacc accaccactg a                                         1341
```

```
SEQ ID NO: 39           moltype = AA  length = 436
FEATURE                 Location/Qualifiers
REGION                  1..436
                        note = Thermus Thermophilus Bacteriophage G20C and Affinity
                        Tag; WT Nanopore
source                  1..436
                        mol_type = protein
                        organism = synthetic construct
SEQUENCE: 39
MGSSHHHHHH SSGLEVLFQG PAKLEGASVP VMSTSYDVVV DREFDELLQG KDGLLVYHKM  60
LSDGTVKNAL NYIFGRIRSA KWYVEPASTD PEDIAIAAFI HAQLGIDDAS VGKYPFGRLF 120
AIYENAYIYG MAAGEIVLTL GADGKLILDK IVPIHPFNID EVYDEEGGP KALKLSGEVK 180
GGSQFVSGLE IPIWKTVVFL HNDDGSFTGQ SALRAAVPHW LAKRALILLI NHGLERFMIG 240
VPTLTIPKSV RQGTKQWEAA KEIVKNFVQK PRHGIILPDD WKFDTVDLKS AMPDAIPYLT 300
```

```
YHDAGIARAL GIDFNTVQLN MGVQAINIGE FVSLTQQTII SLQREFASAV NLYLIPKLVL  360
PNWPSATRFP RLTFEMEERN DFSAAANLMG MLINAVKDSE DIPTELKALI DALPSKMRRA  420
LGVVDEVREA VRQPAD                                                 436

SEQ ID NO: 40          moltype = AA  length = 448
FEATURE                Location/Qualifiers
source                 1..448
                       mol_type = protein
                       organism = Thermus phage P23-45
SEQUENCE: 40
MAKRGRKPKE LVPGPGSIDP SDVPKLEGAS VPVMSTSYDV VVDREFDELL QGKDGLLVYH   60
KMLSDGTVKN ALNYIFGRIR SAKWYVEPAS TDPEDIAIAA FIHAQLGIDD ASVGKYPFGR  120
LFAIYENAYI YGMAAGEIVL TLGADGKLIL DKIVPIHPFN IDEVLYDEEG GPKALKLSGE  180
VKGGSQFVNG LEIPIWKTVV FLHNDDGSFT GQSALRAAVP HWLAKRALIL LINHGLERFM  240
IGVPTLTIPK SVRQGTKQWE AAKEIVKNFV QKPRHGIILP DDWKFDTVDL KSAMPDAIPY  300
LTYHDAGIAR ALGIDFNTVQ LNMGVQAVNI GEFVSLTQQT IISLQREFAS AVNLYLIPKL  360
VLPNWPGATR FPRLTFEMEE RNDFSAAANL MGMLINAVKD SEDIPTELKA LIDALPSKMR  420
RALGVVDEVR EAVRQPADSR YLYTRRRR                                    448

SEQ ID NO: 41          moltype = DNA  length = 1347
FEATURE                Location/Qualifiers
source                 1..1347
                       mol_type = genomic DNA
                       organism = Thermus phage P23-45
SEQUENCE: 41
atggctaagc gaggacgtaa acccaaggag ctggtccccg gacctggctc cattgaccca   60
tccgacgttc ccaagctcga gggcgcctcc gtgccggtga tgtccaccag ctacgacgtg  120
gtggttgacc gggagtttga cgagctactg cagggcaagg acggcctgct cgtctaccac  180
aagatgctct cggacggcac ggtcaagaac gccctcaact acatcttcgg cgcgatccgc  240
tcggcgaagt ggtacgtaga gcccgcctct accgacccgg aggacatcgc catcgccgcc  300
ttcatccacg cccagttagg catagacgat gcttcggtag gcaagtatcc ttttggccgt  360
cttttcgcca tctacgaaaa cgcctacata tacggcatgg ccgccgggga aatcgtactg  420
acccttggcg cggacggcaa gctcatcctt gacaaaatcg tccctatcca cccttttcaac  480
attgacgagg tgctttacga cgaggaaggc ggtccaaagg cgctaaagct aagcggagag  540
gtgaagggcg gaagccagtt cgtgaacggg ctggagattc ctatctggaa gaccgtggtc  600
ttcctgcaca acgacgacgg ctccttcacc ggacagagcg ccctcagagc cgccgttccg  660
cattggctag ccaaacgcgc ccttatcctc ctcatcaacc acgggctaga gcgcttcatg  720
attggcgtgc ccacctcac catccccaag agcgtgcgtc aggggaccaa gcaatgggag  780
gccgccaagg aaatcgtcaa gaactttgtt caaaaaccac ggcatggtat aatactgcct  840
gacgactgga agtttgacac ggtagacctg aagtcggcca tgcccgacgc cattccctac  900
ctgacctacc acgacgcggg catcgctagg gcgcttggca tagacttcaa caccgttcag  960
ctaaacatgg gggtacaggc ggtcaacatc ggcgagttcg taagcctgac ccagcagacc 1020
atcatttcgc tccagcggga gttcgctagc gcggtcaacc tctacctcat ccccaagcta 1080
gtgcttccca actggccggg cgccacccgc tttcccaggc tcacctttga gatggaggag 1140
cgtaacgact tctccgccgc ggccaacctt atgggcatgc tcatcaacgc ggttaaggac 1200
tccgaagaca ttcccaccga gctcaaggcg ctaatagacg ctctgcccag caagatgcgc 1260
cgggcgcttg gcgtggtgga cgaggtgagg gaagcggtac gccaacccgc cgattcccgc 1320
tacctgtaca cgcgaaggag gaggtag                                    1347
```